United States Patent
Zhou et al.

(10) Patent No.: US 6,919,451 B2
(45) Date of Patent: Jul. 19, 2005

(54) SYNTHESIS OF 4,5-DIHYDRO-PYRAZOLO [3,4-C] PYRID-2-ONES

(75) Inventors: Jiacheng Zhou, Hackessin, DE (US); Lynette M. Oh, West Chester, PA (US); Philip Ma, West Chester, PA (US); Hui-Yin Li, Hockessin, DE (US); Pasquale Confalone, Greenville, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/308,741

(22) Filed: Dec. 3, 2002

(65) Prior Publication Data

US 2003/0181466 A1 Sep. 25, 2003

Related U.S. Application Data

(60) Provisional application No. 60/339,085, filed on Dec. 10, 2001.

(51) Int. Cl.$^7$ ............................................. C07D 471/04
(52) U.S. Cl. ..................... 544/127; 544/333; 544/405; 546/119; 546/120
(58) Field of Search ................................ 546/120, 119; 544/127, 333, 405

(56) References Cited

U.S. PATENT DOCUMENTS 4,409,228 A  10/1983  Nisato et al. ............... 424/267
6,329,527 B1  12/2001  Zhou et al. .................. 548/241
6,413,980 B1  7/2002  Fevig et al. ................ 514/300
6,465,656 B2  10/2002  Zhou et al. .............. 514/724.2
2003/0191115 A1  10/2003  Pinto et al. ................. 548/241

FOREIGN PATENT DOCUMENTS

| WO | WO0039131 | 7/2000 |
| WO | WO01/29006 | 4/2001 |
| WO | WO2003026652 | 4/2003 |

*Primary Examiner*—Richard L. Raymond
(74) *Attorney, Agent, or Firm*—Jing G. Sun; David H. Vance

(57) ABSTRACT

A novel process and intermediates thereof for making 4,5-dihydro-pyrazolo[3,4-c]pyrid-2-ones of the type shown below from appropriate phenyl hydrazines is described.

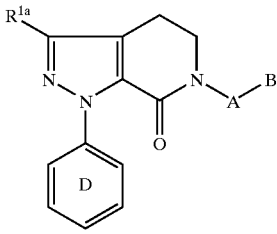

IV

These compounds are useful as factor Xa inhibitors.

9 Claims, No Drawings

SYNTHESIS OF 4,5-DIHYDRO-PYRAZOLO[3,4-C] PYRID-2-ONES

CROSS-REFERENCE TO RELATED APPLICATIONS

The present application claims the priority benefit of U.S. Provisional Application No. 60/339,085, filed Dec. 10, 2001, the disclosure of which is incorporated herein by reference in its entirety.

FIELD OF THE INVENTION

The present invention relates generally to processes for the preparation of 4,5-dihydro-pyrazolo[3,4-c]pyrid-2-ones and intermediates for the synthesis of the same, such pyrazolo-pyridinones being useful as factor Xa inhibitors.

BACKGROUND OF THE INVENTION 4,5-Dihydro-pyrazolo[3,4-c]pyrid-2-one compounds of the type shown below are currently being studied as factor Xa inhibitors in clinical settings.

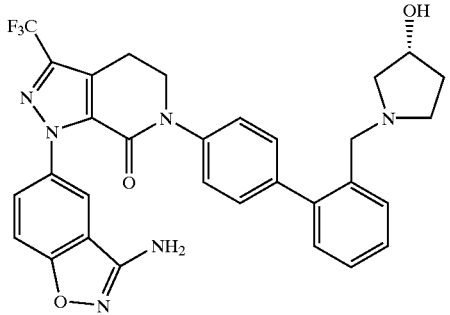

As one of ordinary skill in the art understands, clinical trials and NDA submissions require practical, large-scale synthesis of the active drug. Consequently, it is desirable to find new synthetic procedures for making 4,5-dihydro-pyrazolo[3,4-c]pyrid-2-ones.

SUMMARY OF THE INVENTION

Accordingly, the present invention provides a novel process for making 4,5-dihydro-pyrazolo[3,4-c]pyrid-2-ones.

The present invention provides novel intermediates for the syntheses of 4,5-dihydro-pyrazolo[3,4-c]pyrid-2-ones.

These and other objects, which will become apparent during the following detailed description, have been achieved by the inventors' discovery that compounds of formula IV can be formed from aryl hydrazines.

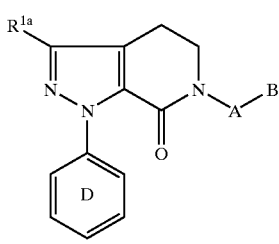

DETAILED DESCRIPTION OF THE INVENTION

[1] Thus, in an embodiment, the present invention provides a novel process for preparing a compound of formula III:

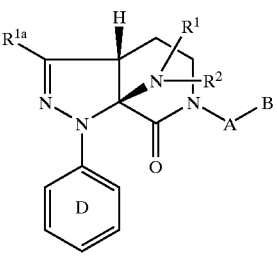

comprising:
(a) contacting a compound of formula I with a compound of formula II in the presence of a base;

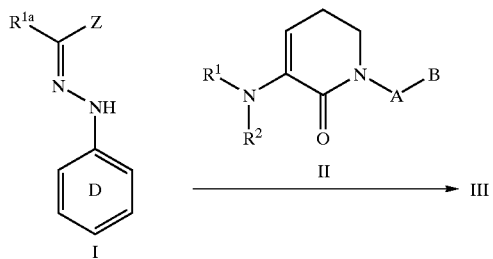

wherein, Z is selected from Cl, Br, I, $OSO_2Me$, $OSO_2Ph$, and $OSO_2Ph$-p-Me;

ring D is selected from 4-chlorophenyl, 4-methoxyphenyl, 2-cyanophenyl, 2-(aminomethyl)phenyl, 2-($PgNHCH_2$)phenyl, 3-cyanophenyl, 3-(aminomethyl)phenyl, 3-($PgNHCH_2$)phenyl, 3-cyano-4-fluorophenyl, (3-amino)benz[d]isoxazol-6-yl, and (3-PgNH)benz[d]isoxazol-6-yl;

Pg is an amine protecting group;

$R^1$ and $R^2$ are selected from $C_{1-6}$ alkyl, cyclopropyl, cyclobutyl, cyclopentyl, cyclohexyl, phenyl, and benzyl; alternatively, $NR^1R^2$ is a 3–8 membered ring consisting of: carbon atoms, N, and 0–1 O atoms;

$R^{1a}$ is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $CH_2OCH_3$, $CO_2CH_3$, $CH_2CO_2CH_3$, $CO_2CH_2CH_3$, $CH_2CO_2CH_2CH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—N, N—S, N—O, or N—CN bond;

A is selected from phenyl substituted with 0–1 $R^4$, pyridyl substituted with 0–1 $R^4$, and pyrimidyl substituted with 0–1 $R^4$;

B is selected from $B^1$, Cl, Br, I, OMs, OTs, $OSO_2Ph$, $CH_2Br$, $CH_2OH$, and CHO;

alternatively, A-B is hydrogen;

$B^1$ is Y or X—Y;

X is selected from $C_{1-4}$ alkylene, —$CR^2(CHR^2R^{2b})(CH_2)_t$—, —C(O)—, —$CR^2(OR^2)$—, —$CR^2(SR^2)$—, —$C(O)CR^2R^{2a}$—, —$CR^2R^{2a}C(O)$, —$S(O)_g$—, —$S(O)_p$$CR^2R^{2a}$—, —$CR^2R^{2a}S(O)_p$—, —$S(O)_2NR^2$—, —$NR^2S(O)_2$—, —$NR^2S(O)_2CR^2R^{2a}$—, —$CR^2R^{2a}S(O)_2NR^2$—, —$NR^2S(O)_2NR^2$—, —$C(O)NR^2$—, —$NR^2C(O)$—, —$C(O)NR^2CR^2R^{2a}$—, —$NR^2C(O)CR^2R^{2a}$—, —CR²R²ᵃC(O)NR²—, —CR²R²ᵃNR²C(O)—, —NR²C(O)O—, —OC(O)NR²—, —NR²C(O)NR²—, —NR²—, —NR²CR²R²ᵃ—, —CR²R²ᵃNR²—, O, —CR²R²ᵃO—, and —OCR²R²ᵃ—;

Y is selected from:
C$_{3-10}$ carbocycle substituted with 0–2 R⁴ᵃ, and
5–10 membered heterocycle containing from 1–4 heteroatoms selected from the group consisting of N, O, and S, substituted with 0–2 R⁴ᵃ;

R⁴, at each occurrence, is selected from H, (CH₂)$_r$OR², F, Cl, Br, I, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, —CN, NO₂, (CH₂)$_r$NR²R²ᵃ, (CH₂)$_r$C(O)R²ᶜ, NR²C(O)R²ᵇ, C(O)NR²R²ᵃ, NR²C(O)NR²R²ᵃ, C(=NR²)NR²R²ᵃ, C(=NS(O)₂R⁵)NR²R²ᵃ, NHC(=NR²)NR²R²ᵃ, C(O)NHC(=NR²)NR²R²ᵃ, SO₂NR²R²ᵃ, NR²SO₂NR²R²ᵃ, NR²SO₂—C$_{1-4}$ alkyl, NR²SO₂R⁵, S(O)$_p$R⁵, and (CF₂)$_r$CF₃;

R⁴ᵃ, at each occurrence, is selected from H, =O, CHO, (CH₂)$_r$OR², (CH₂)$_r$—F, (CH₂)$_r$—Br, (CH₂)$_r$—Cl, Cl, Br, F, I, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, —CN, NO₂, (CH₂)$_r$NR²R²ᵃ, (CH₂)$_r$C(O)R²ᶜ, NR²C(O)R²ᵇ, C(O)NR²R²ᵃ, (CH₂)$_r$N=CHOR³, C(O)NH(CH₂)₂NR²R²ᵃ, NR²C(O)NR²R²ᵃ, C(=NR²)NR²R²ᵃ, NHC(=NR²)NR²R²ᵃ, SO₂NR²R²ᵃ, NR²SO₂NR²R²ᵃ, NR²SO₂—C$_{1-4}$ alkyl, C(O)NHSO₂—C$_{1-4}$ alkyl, NR²SO₂R⁵, S(O)$_p$R⁵, and (CF₂)$_r$CF₃;

R², at each occurrence, is selected from H, CF₃, C$_{1-6}$ alkyl, benzyl, C$_{3-6}$ carbocycle substituted with 0–2 R⁴ᵇ, a C$_{3-6}$ carbocycle-CH₂— substituted with 0–2 R⁴ᵇ, and 5–6 membered heterocycle containing from 1–4 heteroatoms selected from the group consisting of N, O, and S, substituted with 0–2 R⁴ᵇ;

alternatively, when R² is attached to an amino nitrogen, then R² is an amine protecting group;

R²ᵃ, at each occurrence, is selected from H, CF₃, C$_{1-6}$ alkyl, benzyl, C$_{3-6}$ carbocycle substituted with 0–2 R⁴ᵇ, and 5–6 membered heterocycle containing from 1–4 heteroatoms selected from the group consisting of N, O, and S, substituted with 0–2 R⁴ᵇ;

R²ᵇ, at each occurrence, is selected from CF₃, C$_{1-4}$ alkoxy, C$_{1-6}$ alkyl, benzyl, C$_{3-6}$ carbocycle substituted with 0–2 R⁴ᵇ, and 5–6 membered heterocycle containing from 1–4 heteroatoms selected from the group consisting of N, O, and S, substituted with 0–2 R⁴ᵇ;

R²ᶜ, at each occurrence, is selected from CF₃, OH, C$_{1-4}$ alkoxy, C$_{1-6}$ alkyl, benzyl, C$_{3-6}$ carbocycle substituted with 0–2 R⁴ᵇ, and 5–6 membered heterocycle containing from 1–4 heteroatoms selected from the group consisting of N, O, and S, substituted with 0–2 R⁴ᵇ;

alternatively, R² and R²ᵃ, together with the atom to which they are attached, combine to form a 5 or 6 membered saturated, partially saturated or unsaturated ring substituted with 0–2 R⁴ᵇ and containing from 0–1 additional heteroatoms selected from the group consisting of N, O, and S;

R³, at each occurrence, is selected from H, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, and phenyl;

R³ᵃ, at each occurrence, is selected from H, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, and phenyl;

R³ᵇ, at each occurrence, is selected from H, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, and phenyl;

R³ᶜ, at each occurrence, is selected from CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, and phenyl;

R⁴ᵇ, at each occurrence, is selected from H, =O, (CH₂)$_r$OR³, F, Cl, Br, I, CH₃, CH₂CH₃, CH₂CH₂CH₃, CH(CH₃)₂, CH₂CH₂CH₂CH₃, CH₂CH(CH₃)₂, CH(CH₃) CH₂CH₃, CH(CH₃)₃, —CN, NO₂, (CH₂)$_r$NR³R³ᵃ, (CH₂)$_r$C(O)R³, (CH₂)$_r$C(O)OR³ᶜ, NR³C(O)R³ᵃ, C(O)NR³R³ᵃ, NR³C(O)NR³R³ᵃ, C(=NR³)NR³R³ᵃ, NR³C(=NR³)NR³R³ᵃ, SO₂NR³R³ᵃ, NR³SO₂NR³R³ᵃ, NR³SO₂—C$_{1-4}$ alkyl, NR³SO₂CF₃, NR³SO₂-phenyl, S(O)$_p$CF₃, S(O)$_p$—C$_{1-4}$ alkyl, S(O)$_p$-phenyl, and (CF₂)$_r$CF₃;

R⁵, at each occurrence, is selected from CF₃, C$_{1-6}$ alkyl, phenyl substituted with 0–2 R⁶, and benzyl substituted with 0–2 R⁶;

R⁶, at each occurrence, is selected from H, OH, (CH₂)$_r$OR², halo, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, CN, NO₂, (CH₂)$_r$NR²R²ᵃ, (CH₂)$_r$C(O)R²ᵇ, NR²C(O)R²ᵇ, NR²C(O)NR²R²ᵃ, C(=NH)NH₂, NHC(=NH)NH₂, SO₂NR²R²ᵃ, NR²SO₂NR²R²ᵃ, and NR²SO₂C$_{1-4}$ alkyl;

p, at each occurrence, is selected from 0, 1, and 2;
r, at each occurrence, is selected from 0, 1, 2, and 3; and,
t, at each occurrence, is selected from 0, 1, 2, and 3.

[2] In a preferred embodiment, the present invention provides a novel process wherein:

R¹ᵃ is selected from CF₃, CO₂CH₃, CH₂CO₂CH₃, CO₂CH₂CH₃, S(O)₂CH₃, CH₂S(O)₂CH₃, C(O)NH₂, CH₂C(O)NH₂, SO₂NH₂, CH₂SO₂NH₂, pyridin-2-yl, pyridin-3-yl, pyridin-4-yl, pyridin-2-yl-N-oxide, pyridin-3-yl-N-oxide, pyridin-4-yl-N-oxide, imidazol-1-yl, CH₂-imidazol-1-yl, 1,2,3,4-tetrazol-1-yl, 1,2,3,4-tetrazol-5-yl, CH₂-1,2,3,4-tetrazol-1-yl, and CH₂-1,2,3,4-tetrazol-5-yl, provided that R¹ᵃ forms other than an N-halo, N—N, N—S, N—O, or N—CN bond;

X is selected from C$_{1-4}$ alkylene, —C(O)—, —C(O)CR²R²ᵃ—, —CR²R²ᵃC(O), —C(O)NR²—, —NR²C(O)—, —NR²—, —NR²CR²R²ᵃ—, —CR²R²ᵃNR²—, O, —CR²R²ᵃO—, and —OCR²R²ᵃ—;

Y is selected from one of the following carbocyclic and heterocycles that are substituted with 0–2 R⁴ᵃ;

cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

R⁴, at each occurrence, is selected from H, OR², CH₂OR², F, Cl, Br, I, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, —CN, NO₂, NR²R²ᵃ, CH₂NR²R²ᵃ, C(O)R²ᶜ, CH₂C(O)R²ᶜ, NR²C(O)R²ᵇ, C(O)NR²R²ᵃ, SO₂NR²R²ᵃ, S(O)$_p$R⁵, and CF₃;

R⁴ᵃ, at each occurrence, is selected from H, =O, CHO, OR², CH₂OR², Cl, Br, F, I, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, —CN, NO₂, NR²R²ᵃ, CH₂NR²R²ᵃ, C(O)R²ᶜ, CH₂C(O)R²ᶜ, NR²C(O)R²ᵇ, C(O)NR²R²ᵃ, SO₂NR²R²ᵃ, S(O)$_p$R⁵, and CF₃;

R², at each occurrence, is selected from H, CF₃, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, benzyl, $C_{3-6}$ carbocycle substituted with 0–2 $R^{4b}$, a $C_{3-6}$ carbocycle-$CH_2$— substituted with 0–2 $R^{4b}$, and 5–6 membered heterocycle containing from 1–4 heteroatoms selected from the group consisting of N, O, and S, substituted with 0–2 $R^{4b}$;

alternatively, when $R^2$ is attached to an amino nitrogen, then $R^2$ is an amine protecting group;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, benzyl, $C_{3-6}$ carbocycle substituted with 0–2 $R^{4b}$, and 5–6 membered heterocycle containing from 1–4 heteroatoms selected from the group consisting of N, O, and S, substituted with 0–2 $R^{4b}$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, benzyl, $C_{3-6}$ carbocycle substituted with 0–2 $R^{4b}$, and 5–6 membered heterocycle containing from 1–4 heteroatoms selected from the group consisting of N, O, and S, substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, benzyl, $C_{3-6}$ carbocycle substituted with 0–2 $R^{4b}$, and 5–6 membered heterocycle containing from 1–4 heteroatoms selected from the group consisting of N, O, and S, substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^{4b}$, at each occurrence, is selected from H, =O, $OR^3$, $CH_2OR^3$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $S(O)_p$—$C_{1-4}$ alkyl, $S(O)_p$-phenyl, and $CF_3$;

$R^5$, at each occurrence, is selected from $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, phenyl substituted with 0–2 $R^6$, and benzyl substituted with 0–2 $R^6$;

$R^6$, at each occurrence, is selected from H, OH, $OR^2$, $CH_2OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $SO_2NR^2R^{2a}$, $NR^2SO_2NR^2R^{2a}$, and $NR^2SO_2C_{1-4}$ alkyl; and, p, at each occurrence, is selected from 0, 1, and 2.

[3] In another preferred embodiment, the present invention provides a novel process wherein:

$NR^1R^2$ is selected from morpholino, pyrrolidino, and piperidino;

$R^{1a}$ is selected from $CF_3$, $S(O)_2CH_3$, and $C(O)NH_2$;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

$B^1$ is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N-methylaminomethyl)phenyl, 2-(N-ethyl-N-methylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(methylaminomethyl)-1-imidazolyl, 2-(N-(cyclopropylmethyl)aminomethyl)phenyl, 2-(N-(cyclobutyl)aminomethyl)phenyl, 2-(N-(cyclopentyl)aminomethyl)phenyl, 2-(N-(4-hydroxypiperidinyl)methyl)phenyl, and 2-(N-(3-hydroxypyrrolidinyl)methyl)phenyl; and, alternatively, $B^1$ is selected from the group: 2-(N-Pg-N-methylaminomethyl)phenyl, 2-(N-Pg-N-methylaminomethyl)-1-imidazolyl, 2-(N-Pg-N-(cyclopropylmethyl)aminomethyl)phenyl, 2-(N-Pg-N-(cyclobutyl)aminomethyl)phenyl, and 2-(N-Pg-N-(cyclopentyl)aminomethyl)phenyl.

[4] In another preferred embodiment, in reaction (a), the compound of formula I is contacted with the compound of formula II followed by the addition of the base.

[5] In another preferred embodiment, in reaction (a), the compound of formula I is contacted with a base, followed by the addition of the compound of formula II.

[6] In another preferred embodiment, the base in reaction (a) is selected from: triethylamine, diisopropylethylamine, and N-methylmorpholine.

[7] In another embodiment, the present invention provides a novel process for preparing a compound of formula IV:

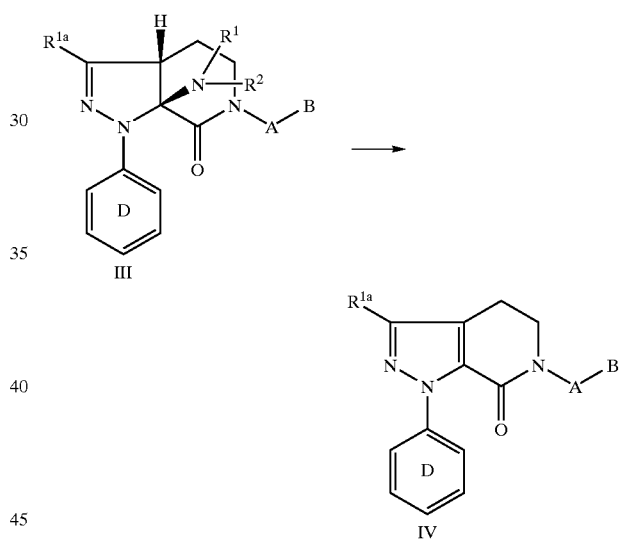

the process comprising:

(b) contacting a compound of formula III with an acid to form a compound of formula IV;

wherein ring D is selected from 4-chlorophenyl, 4-methoxyphenyl, 2-cyanophenyl, 2-(aminomethyl)phenyl, 2-(PgNHCH$_2$)phenyl, 3-cyanophenyl, 3-(aminomethyl)phenyl, 3-(PgNHCH$_2$)phenyl, 3-cyano-4-fluorophenyl, (3-amino)benz[d]isoxazol-6-yl, and (3-PgNH)benz[d]isoxazol-6-yl;

Pg is an amine protecting group;

$R^1$ and $R^2$ are selected from $C_{1-6}$ alkyl, cyclopropyl, cyclobutyl, cyclopentyl, cyclohexyl, phenyl, and benzyl;

alternatively, $NR^1R^2$ is a 3–8 membered ring consisting of: carbon atoms, N, and 0–1 O atoms;

$R^{1a}$ is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $CH_2OCH_3$, $CO_2CH_3$, $CH_2CO_2CH_3$, $CO_2CH_2CH_3$, $CH_2CO_2CH_2CH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, SO$_2$NH$_2$, CH$_2$SO$_2$NH$_2$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, CH$_2$-imidazol-1-yl, 1,2,3,4-tetrazol-1-yl, 1,2,3,4-tetrazol-5-yl, CH$_2$-1,2,3,4-tetrazol-1-yl, and CH$_2$-1,2,3,4-tetrazol-5-yl, provided that R$^{1a}$ forms other than an N-halo, N—N, N—S, N—O, or N—CN bond;

A is selected from phenyl substituted with 0–1 R$^4$, pyridyl substituted with 0–1 R$^4$, and pyrimidyl substituted with 0–1 R$^4$;

B is selected from B$^1$, Cl, Br, I, OMs, OTs, OSO$_2$Ph, CH$_2$Br, CH$_2$OH, and CHO;

alternatively, A-B is hydrogen;

B$^1$ is Y or X—Y;

X is selected from C$_{1-4}$ alkylene, —CR$^2$(CHR$^2$R$^{2b}$) (CH$_2$)$_r$—, —C(O)—, —CR$^2$(OR$^2$)—, —CR$^2$(SR$^2$)—, —C(O)CR$^2$R$^{2a}$—, —CR$^2$R$^{2a}$C(O), —S(O)$_p$—, —S(O)$_p$CR$^2$R$^{2a}$—, —CR$^2$R$^{2a}$S(O)$_p$—, —S(O)$_2$NR$^2$—, —NR$^2$S(O)$_2$—, —NR$^2$S(O)$_2$CR$^2$R$^{2a}$—, —CR$^2$R$^{2a}$S(O)$_2$NR$^2$—, —NR$^2$S(O)$_2$NR$^2$—, —C(O)NR$^2$—, —NR$^2$C(O)—, —C(O)NR$^2$CR$^2$R$^{2a}$—, —NR$^2$C(O)CR$^2$R$^{2a}$—, —CR$^2$R$^{2a}$C(O)NR$^2$—, —CR$^2$R$^{2a}$NR$^2$C(O)—, —NR$^2$C(O)O—, —OC(O)NR$^2$—, —NR$^2$C(O)NR$^2$—, —NR$^2$—, —NR$^2$CR$^2$R$^{2a}$—, —CR$^2$R$^{2a}$NR$^2$—, O, —CR$^2$R$^{2a}$O—, and —OCR$^2$R$^{2a}$—;

Y is selected from:
C$_{3-10}$ carbocycle substituted with 0–2 R$^{4a}$, and
5–10 membered heterocycle containing from 1–4 heteroatoms selected from the group consisting of N, O, and S, substituted with 0–2 R$^{4a}$;

R$^4$, at each occurrence, is selected from H, (CH$_2$)$_r$OR$^2$, F, Cl, Br, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, CH(CH$_3$)$_3$, —CN, NO$_2$, (CH$_2$)$_r$NR$^2$R$^{2a}$, (CH$_2$)$_r$C(O)R$^{2c}$, NR$^2$C(O)R$^{2b}$, C(O)NR$^2$R$^{2a}$, NR$^2$C(O)NR$^2$R$^{2a}$, C(=NR$^2$)NR$^2$R$^{2a}$, C(=NS(O)$_2$R$^5$)NR$^2$R$^{2a}$, NHC(=NR$^2$)NR$^2$R$^{2a}$, C(O)NHC(=NR$^2$)NR$^2$R$^{2a}$, SO$_2$NR$^2$R$^{2a}$, NR$^2$SO$_2$NR$^2$R$^{2a}$, NR$^2$SO$_2$—C$_{1-4}$ alkyl, NR$^2$SO$_2$R$^5$, S(O)$_p$R$^5$, and (CF$_2$)$_r$CF$_3$;

R$^{4a}$, at each occurrence, is selected from H, =O, CHO, (CH$_2$)$_r$OR$^2$, (CH$_2$)$_r$—F, (CH$_2$)$_r$—Br, (CH$_2$)$_r$—Cl, Cl, Br, F, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, CH(CH$_3$)$_3$, —CN, NO$_2$, (CH$_2$)$_r$NR$^2$R$^{2a}$, (CH$_2$)$_r$C(O)R$^{2c}$, NR$^2$C(O)R$^{2b}$, C(O)NR$^2$R$^{2a}$, (CH$_2$)$_r$N=CHOR$^3$, C(O) NH(CH$_2$)$_2$NR$^2$R$^{2a}$, NR$^2$C(O)NR$^2$R$^{2a}$, C(=NR$^2$) NR$^2$R$^{2a}$, NHC(=NR$^2$)NR$^2$R$^{2a}$, SO$_2$NR$^2$R$^{2a}$, NR$^2$SO$_2$NR$^2$R$^{2a}$, NR$^2$SO$_2$—C$_{1-4}$ alkyl, C(O)NHSO$_2$—C$_{1-4}$ alkyl, NR$^2$SO$_2$R$^5$, S(O)$_p$R$^5$, and (CF$_2$)$_r$CF$_3$;

R$^2$, at each occurrence, is selected from H, CF$_3$, C$_{1-6}$ alkyl, benzyl, C$_{3-6}$ carbocycle substituted with 0–2 R$^{4b}$, a C$_{3-6}$ carbocycle-CH$_2$— substituted with 0–2 R$^{4b}$, and 5–6 membered heterocycle containing from 1–4 heteroatoms selected from the group consisting of N, O, and S, substituted with 0–2 R$^{4b}$;

alternatively, when R$^2$ is attached to an amino nitrogen, then R$^2$ is an amine protecting group;

R$^{2a}$, at each occurrence, is selected from H, CF$_3$, C$_{1-6}$ alkyl, benzyl, C$_{3-6}$ carbocycle substituted with 0–2 R$^{4b}$, and 5–6 membered heterocycle containing from 1–4 heteroatoms selected from the group consisting of N, O, and S, substituted with 0–2 R$^{4b}$;

R$^{2b}$, at each occurrence, is selected from CF$_3$, C$_{1-4}$ alkoxy, C$_{1-6}$ alkyl, benzyl, C$_{3-6}$ carbocycle substituted with 0–2 R$^{4b}$, and 5–6 membered heterocycle containing from 1–4 heteroatoms selected from the group consisting of N, O, and S, substituted with 0–2 R$^{4b}$;

R$^{2c}$, at each occurrence, is selected from CF$_3$, OH, C$_{1-4}$ alkoxy, C$_{1-6}$ alkyl, benzyl, C$_{3-6}$ carbocycle substituted with 0–2 R$^{4b}$, and 5–6 membered heterocycle containing from 1–4 heteroatoms selected from the group consisting of N, O, and S, substituted with 0–2 R$^{4b}$;

alternatively, R$^2$ and R$^{2a}$, together with the atom to which they are attached, combine to form a 5 or 6 membered saturated, partially saturated or unsaturated ring substituted with 0–2 R$^{4b}$ and containing from 0–1 additional heteroatoms selected from the group consisting of N, O, and S;

R$^3$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, CH(CH$_3$)$_3$, and phenyl;

R$^{3a}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, CH(CH$_3$)$_3$, and phenyl;

R$^{3b}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, CH(CH$_3$)$_3$, and phenyl;

R$^{3c}$, at each occurrence, is selected from CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, CH(CH$_3$)$_3$, and phenyl;

R$^{4b}$, at each occurrence, is selected from H, =O, (CH$_2$)$_r$OR$^3$, F, Cl, Br, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$) CH$_2$CH$_3$, CH(CH$_3$)$_3$, —CN, NO$_2$, (CH$_2$)$_r$NR$^3$R$^{3a}$, (CH$_2$)$_r$C(O)R$^3$, (CH$_2$)$_r$C(O)OR$^{3c}$, NR$^3$C(O)R$^{3a}$, C(O)NR$^3$R$^{3a}$, NR$^3$C(O)NR$^3$R$^{3a}$, C(=NR$^3$)NR$^3$R$^{3a}$, NR$^3$C(=NR$^3$) NR$^3$R$^{3a}$, SO$_2$NR$^3$R$^{3a}$, NR$^3$SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, and (CF$_2$)$_r$CF$_3$;

R$^5$, at each occurrence, is selected from CF$_3$, C$_{1-6}$ alkyl, phenyl substituted with 0–2 R$^6$, and benzyl substituted with 0–2 R$^6$;

R$^6$, at each occurrence, is selected from H, OH, (CH$_2$)$_r$OR$^2$, halo, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, CH(CH$_3$)$_3$, CN, NO$_2$, (CH$_2$)$_r$NR$^2$R$^{2a}$, (CH$_2$)$_r$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

p, at each occurrence, is selected from 0, 1, and 2;

r, at each occurrence, is selected from 0, 1, 2, and 3; and t, at each occurrence, is selected from 0, 1, 2, and 3.

[8] In a preferred embodiment, the present invention provides a novel process wherein:

R$^{1a}$ is selected from CF$_3$, CO$_2$CH$_3$, CH$_2$CO$_2$CH$_3$, CO$_2$CH$_2$CH$_3$, S(O)$_2$CH$_3$, CH$_2$S(O)$_2$CH$_3$, C(O)NH$_2$, CH$_2$C(O)NH$_2$, SO$_2$NH$_2$, CH$_2$SO$_2$NH$_2$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, CH$_2$-imidazol-1-yl, 1,2,3,4-tetrazol-1-yl, 1,2,3,4-tetrazol-5-yl, CH$_2$-1,2,3,4-tetrazol-1-yl, and CH$_2$-1,2,3,4-tetrazol-5-yl, provided that R$^{1a}$ forms other than an N-halo, N—N, N—S, N—O, or N—CN bond;

X is selected from C$_{1-4}$ alkylene, —C(O)—, —C(O) CR$^2$R$^{2a}$—, —CR$^2$R$^{2a}$C(O), —C(O)NR$^2$—, —NR$^2$C (O)—, —NR$^2$—, —NR$^2$CR$^2$R$^{2a}$—, —CR$^2$R$^{2a}$NR$^2$—, O, —CR$^2$R$^{2a}$O—, and —OCR$^2$R$^{2a}$—;

Y is selected from one of the following carbocyclic and heterocycles that are substituted with 0–2 R$^{4a}$;
cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3- oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

$R^4$, at each occurrence, is selected from H, $OR^2$, $CH_2OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, $NO_2$, $NR^2R^{2a}$, $CH_2NR^2R^{2a}$, $C(O)R^{2c}$, $CH_2C(O)R^{2c}$, $NR^2C(O)R^{2b}$, $C(O)NR^2R^{2a}$, $SO_2NR^2R^{2a}$, $S(O)_pR^5$, and $CF_3$;

$R^{4a}$, at each occurrence, is selected from H, =O, CHO, $OR^2$, $CH_2OR^2$, Cl, Br, F, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, $NO_2$, $NR^2R^{2a}$, $CH_2NR^2R^{2a}$, $C(O)R^{2c}$, $CH_2C(O)R^{2c}$, $NR^2C(O)R^{2b}$, $C(O)NR^2R^{2a}$, $SO_2NR^2R^{2a}$, $S(O)_pR^5$, and $CF_3$;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, benzyl, $C_{3-6}$ carbocycle substituted with 0–2 $R^{4b}$, a $C_{3-6}$ carbocycle-$CH_2$— substituted with 0–2 $R^{4b}$, and 5–6 membered heterocycle containing from 1–4 heteroatoms selected from the group consisting of N, O, and S, substituted with 0–2 $R^{4b}$;

alternatively, when $R^2$ is attached to an amino nitrogen, then $R^2$ is an amine protecting group;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, benzyl, $C_{3-6}$ carbocycle substituted with 0–2 $R^{4b}$, and 5–6 membered heterocycle containing from 1–4 heteroatoms selected from the group consisting of N, O, and S, substituted with 0–2 $R^{4b}$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, benzyl, $C_{3-6}$ carbocycle substituted with 0–2 $R^{4b}$, and 5–6 membered heterocycle containing from 1–4 heteroatoms selected from the group consisting of N, O, and S, substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, benzyl, $C_{3-6}$ carbocycle substituted with 0–2 $R^{4b}$, and 5–6 membered heterocycle containing from 1–4 heteroatoms selected from the group consisting of N, O, and S, substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^{4b}$, at each occurrence, is selected from H, =O, $OR^3$, $CH_2OR^3$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $S(O)_p$—$C_{1-4}$ alkyl, $S(O)_p$-phenyl, and $CF_3$;

$R^5$, at each occurrence, is selected from $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, phenyl substituted with 0–2 $R^6$, and benzyl substituted with 0–2 $R^6$;

$R^6$, at each occurrence, is selected from H, OH, $OR^2$, $CH_2OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $SO_2NR^2R^{2a}$, $NR^2SO_2NR^2R^{2a}$, and $NR^2SO_2C_{1-4}$ alkyl; and, p, at each occurrence, is selected from 0, 1, and 2.

[9] In a preferred embodiment, the present invention provides a novel process wherein:

$NR^1R^2$ selected from morpholino, pyrrolidino, and piperidino;

$R^{1a}$ is selected from $CF_3$, $S(O)_2CH_3$, and $C(O)NH_2$;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

$B^1$ is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N-methylaminomethyl)phenyl, 2-(N-ethyl-N-methylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(methylaminomethyl)-1-imidazolyl, 2-(N-(cyclopropylmethyl)aminomethyl)phenyl, 2-(N-(cyclobutyl)aminomethyl)phenyl, 2-(N-(cyclopentyl)aminomethyl)phenyl, 2-(N-(4-hydroxypiperidinyl)methyl)phenyl, and 2-(N-(3-hydroxypyrrolidinyl)methyl)phenyl; and, alternatively, $B^1$ is selected from the group: 2-(N-Pg-N-methylaminomethyl)phenyl, 2-(N-Pg-N-methylaminomethyl)-1-imidazolyl, 2-(N-Pg-N-(cyclopropylmethyl)aminomethyl)phenyl, 2-(N-Pg-N-(cyclobutyl)aminomethyl)phenyl, and 2-(N-Pg-N-(cyclopentyl)aminomethyl)phenyl.

[10] In another preferred embodiment, the acid in reaction (b) is selected from: trifluoroacetic acid, sulfuric acid nitric acid, and hydrochloric acid.

[11] In another embodiment, the present invention provides a novel process, comprising subjecting a compound of formula IV to the following reactions that are performed, when applicable, in any order:

(c1) when ring D is a 3-cyano-4-fluorophenyl group, converting ring D to 3-PgNH-benz[d]isoxazol-6-yl or 3-amino-benz[d]isoxazol-6-yl;

(c2) when ring D is substituted by a 2-cyano or 3-cyano group, converting the cyano group to PgNH or $NH_2$;

(c3) when B is other than $B^1$, converting it to $B^1$;

(c4) when Pg is present, removing the Pg group;

(c5) when A-B is hydrogen, attaching a non-hydrogen A-B group to the 4,5-dihydro-pyrazolo[3,4-c]pyrid-2-one ring;

(c6) when $R^{4a}$ is CHO, converting it to an aminomethyl group; and, (c7) when $R^{1a}$ is $CO_2H$ or $CO_2$-alkyl, converting it to $C(O)NH_2$.

[12] In another embodiment, the present invention provides a novel process, comprising subjecting a compound of formula IV to the following reactions that are performed, when applicable, in any order:

(c3) when B is other than $B^1$, converting it to $B^1$;

(c4) when Pg is present, removing the Pg group;

(c6) when $R^{4a}$ is CHO, converting it to an aminomethyl group.

[13] In another embodiment, the present invention provides a novel process, comprising subjecting a compound of formula IV to the following reactions that are performed, when applicable, in any order:
(c3) when B is other than $B^1$, converting it to $B^1$;
(c4) when Pg is present, removing the Pg group; and,
(c7) when $R^{1a}$ is $CO_2H$ or $CO_2$-alkyl, converting it to $C(O)NH_2$.

[14] In another embodiment, the present invention provides a novel process, comprising subjecting a compound of formula IV to the following reactions that are performed, when applicable, in any order:
(c6) when $R^{4a}$ is CHO, converting it to an aminomethyl group.

[15] In another embodiment, the present invention provides a novel process, comprising subjecting a compound of formula IV to the following reactions that are performed, when applicable, in any order:
(c7) when $R^{1a}$ is $CO_2H$ or $CO_2$-alkyl, converting it to $C(O)NH_2$.

[16] In another embodiment, the present invention provides a novel compound of formula III:

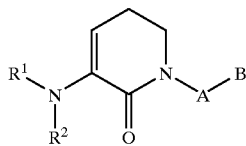

III wherein:
ring D is selected from 4-chlorophenyl, 4-methoxyphenyl, 2-cyanophenyl, 2-(aminomethyl)phenyl, 2-(PgNHCH$_2$) phenyl, 3-cyanophenyl, 3-(aminomethyl)phenyl, 3-(PgNHCH$_2$)phenyl, 3-cyano-4-fluorophenyl, (3-amino) benz[d]isoxazol-6-yl, and (3-PgNH)benz[d]isoxazol-6-yl;
Pg is an amine protecting group;
$R^1$ and $R^2$ are selected from $C_{1-6}$ alkyl, cyclopropyl, cyclobutyl, cyclopentyl, cyclohexyl, phenyl, and benzyl;
alternatively, $NR^1R^2$ is a 3–8 membered ring consisting of: carbon atoms, N, and 0–1 O atoms;
$R^{1a}$ is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $CH_2OCH_3$, $CO_2CH_3$, $CH_2CO_2CH_3$, $CO_2CH_2CH_3$, $CH_2CO_2CH_2CH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—N, N—S, N—O, or N—CN bond;
A is selected from phenyl substituted with 0–1 $R^4$, pyridyl substituted with 0–1 $R^4$, and pyrimidyl substituted with 0–1 $R^4$;
B is selected from $B^1$, Cl, Br, I, OMs, OTs, OSO$_2$Ph, CH$_2$Br, CH$_2$OH, and CHO;
alternatively, A-B is hydrogen;
$B^1$ is Y or X—Y;
X is selected from $C_{1-4}$ alkylene, —CR$^2$(CHR$^2$R$^{2b}$) (CH$_2$)$_r$—, —C(O)—, —CR$^2$(OR$^2$)—, —CR$^2$(SR$^2$)—, —C(O)CR$^2$R$^{2a}$—, —CR$^2$R$^{2a}$C(O), —S(O)$_p$—, —S(O)$_p$CR$^2$R$^{2a}$—, —CR$^2$R$^{2a}$S(O)$_p$—, —S(O)$_2$NR$^2$—, —NR$^2$S (O)$_2$—, —NR$^2$S(O)$_2$CR$^2$R$^{2a}$—, —CR$^2$R$^{2a}$S(O)$_2$NR$^2$—, —NR$^2$S(O)$_2$NR$^2$—, —C(O)NR$^2$—, —NR$^2$C(O)—, —C(O)NR$^2$CR$^2$R$^{2a}$—, —NR$^2$C(O)CR$^2$R$^{2a}$—, —CR$^2$R$^{2a}$C(O)NR$^2$—, —CR$^2$R$^{2a}$NR$^2$C(O)—, —NR$^2$C (O)O—, —OC(O)NR$^2$—, —NR$^2$C(O)NR$^2$—, —NR$^2$—, —NR$^2$CR$^2$R$^{2a}$—, —CR$^2$R$^{2a}$NR$^2$—, O, —CR$^2$R$^{2a}$O—, and —OCR$^2$R$^{2a}$—;
Y is selected from:
$C_{3-10}$ carbocycle substituted with 0–2 $R^{4a}$, and
5–10 membered heterocycle containing from 1–4 heteroatoms selected from the group consisting of N, O, and S, substituted with 0–2 $R^{4a}$;
$R^4$, at each occurrence, is selected from H, (CH$_2$)$_r$OR$^2$, F, Cl, Br, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, CH(CH$_3$)$_3$, —CN, NO$_2$, (CH$_2$)$_r$NR$^2$R$^{2a}$, (CH$_2$)$_r$C(O)R$^{2c}$, NR$^2$C(O)R$^{2b}$, C(O)NR$^2$R$^{2a}$, NR$^2$C(O)NR$^2$R$^{2a}$, C(=NR$^2$)NR$^2$R$^{2a}$, C(=NS(O)$_2$R$^5$)NR$^2$R$^{2a}$, NHC (=NR$^2$)NR$^2$R$^{2a}$, C(O)NHC(=NR$^2$)NR$^2$R$^{2a}$, SO$_2$NR$^2$R$^{2a}$, NR$^2$SO$_2$NR$^2$R$^{2a}$, NR$^2$SO$_2$—C$_{1-4}$ alkyl, NR$^2$SO$_2$R$^5$, S(O)$_p$R$^5$, and (CF$_2$)$_r$CF$_3$;
$R^{4a}$, at each occurrence, is selected from H, =O, CHO, (CH$_2$)$_r$OR$^2$, (CH$_2$)$_r$—F, (CH$_2$)$_r$—Br, (CH$_2$)$_r$—Cl, Cl, Br, F, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, CH(CH$_3$)$_3$, —CN, NO$_2$, (CH$_2$)$_r$NR$^2$R$^{2a}$, (CH$_2$)$_r$C(O)R$^{2c}$, NR$^2$C(O)R$^{2b}$, C(O)NR$^2$R$^{2a}$, (CH$_2$)$_r$N=CHOR$^3$, C(O) NH(CH$_2$)$_2$NR$^2$R$^{2a}$—NR$^2$C(O)NR$^2$R$^{2a}$, C(=NR$^2$) NR$^2$R$^{2a}$, NHC(=NR$^2$)NR$^2$R$^{2a}$, SO$_2$NR$^2$R$^{2a}$, NR$^2$SO$_2$NR$^2$R$^{2a}$, NR$^2$SO$_2$—C$_{1-4}$ alkyl, C(O)NHSO$_2$—C$_{1-4}$ alkyl, NR$^2$SO$_2$R$^5$, S(O)$_p$R$^5$, and (CF$_2$)$_r$CF$_3$;
$R^2$, at each occurrence, is selected from H, CF$_3$, C$_{1-6}$ alkyl, benzyl, C$_{3-6}$ carbocycle substituted with 0–2 $R^{4b}$, a C$_{3-6}$ carbocycle-CH$_2$— substituted with 0–2 $R^{4b}$, and 5–6 membered heterocycle containing from 1–4 heteroatoms selected from the group consisting of N, O, and S, substituted with 0–2 $R^{4b}$;
alternatively, when $R^2$ is attached to an amino nitrogen, then $R^2$ is an amine protecting group;
$R^{2a}$, at each occurrence, is selected from H, CF$_3$, C$_{1-6}$ alkyl, benzyl, C$_{3-6}$ carbocycle substituted with 0–2 $R^{4b}$, and 5–6 membered heterocycle containing from 1–4 heteroatoms selected from the group consisting of N, O, and S, substituted with 0–2 $R^{4b}$;
$R^{2b}$, at each occurrence, is selected from CF$_3$, C$_{1-4}$ alkoxy, C$_{1-6}$ alkyl, benzyl, C$_{3-6}$ carbocycle substituted with 0–2 $R^{4b}$, and 5–6 membered heterocycle containing from 1–4 heteroatoms selected from the group consisting of N, O, and S, substituted with 0–2 $R^{4b}$;
$R^{2c}$, at each occurrence, is selected from CF$_3$, OH, C$_{1-4}$ alkoxy, C$_{1-6}$ alkyl, benzyl, C$_{3-6}$ carbocycle substituted with 0–2 $R^{4b}$, and 5–6 membered heterocycle containing from 1–4 heteroatoms selected from the group consisting of N, O, and S, substituted with 0–2 $R^{4b}$;
alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;
$R^3$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH (CH$_3$)$_2$, CH(CH$_3$)CH$_2$CH$_3$, CH(CH$_3$)$_3$, and phenyl;
$R^{3a}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH (CH$_3$)$_2$, CH(CH$_3$)CH$_2$CH$_3$, CH(CH$_3$)$_3$, and phenyl;
$R^{3b}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH (CH$_3$)$_2$, CH(CH$_3$)CH$_2$CH$_3$, CH(CH$_3$)$_3$, and phenyl;
$R^{3c}$, at each occurrence, is selected from CH$_3$, CH$_2$CH$_3$, CH$_2$CH$_2$CH$_3$, CH(CH$_3$)$_2$, CH$_2$CH$_2$CH$_2$CH$_3$, CH$_2$CH (CH$_3$)$_2$, CH(CH$_3$)CH$_2$CH$_3$, CH(CH$_3$)$_3$, and phenyl;

$R^{4b}$, at each occurrence, is selected from H, =O, $(CH_2)_r$ $OR^3$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)$ $CH_2CH_3$, $CH(CH_3)_3$, —CN, $NO_2$, $(CH_2)_rNR^3R^{3a}$, $(CH_2)_r$ $C(O)R^3$, $(CH_2)_rC(O)OR^{3c}$, $NR^3C(O)R^{3a}$, $C(O)NR^3R^{3a}$, $NR^3C(O)NR^3R^{3a}$, $C(=NR^3)NR^3R^{3a}$, $NR^3C(=NR^3)$ $NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, and $(CF_2)_rCF_3$;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $(CH_2)_rOR^2$, halo, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $C(=NH)NH_2$, NHC$(=NH)NH_2$, $SO_2NR^2R^{2a}$, $NR^2SO_2NR^2R^{2a}$, and $NR^2SO_2C_{1-4}$ alkyl;

p, at each occurrence, is selected from 0, 1, and 2;
r, at each occurrence, is selected from 0, 1, 2, and 3; and,
t, at each occurrence, is selected from 0, 1, 2, and 3.

[17] In another preferred embodiment, the present invention provides a novel compound wherein:

$R^{1a}$ is selected from $CF_3$, $CO_2CH_3$, $CH_2CO_2CH_3$, $CO_2CH_2CH_3$, $S(O)_2CH_3$, $CH_2S(O)_2CH_3$, $C(O)NH_2$, $CH_2C(O)NH_2$, $SO_2NH_2$, $CH_2SO_2NH_2$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—N, N—S, N—O, or N—CN bond;

X is selected from $C_{1-4}$ alkylene, —C(O)—, —C(O) $CR^2R^{2a}$—, —$CR^2R^{2a}C(O)$, —C(O)$NR^2$—, —$NR^2C$ (O)—, —$NR^2$—, —$NR^2CR^2R^{2a}$—, —$CR^2R^{2a}NR^2$—, O, —$CR^2R^{2a}O$—, and —$OCR^2R^{2a}$—;

Y is selected from one of the following carbocyclic and heterocycles that are substituted with 0–2 $R^{4a}$;

cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

$R^4$, at each occurrence, is selected from H, $OR^2$, $CH_2OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, $NO_2$, $NR^2R^{2a}$, $CH_2NR^2R^{2a}$, $C(O)R^{2c}$, $CH_2C(O)R^{2c}$, $NR^2C(O)R^{2b}$, $C(O)NR^2R^{2a}$, $SO_2NR^2R^{2a}$, $S(O)_pR^5$, and $CF_3$;

$R^{4a}$, at each occurrence, is selected from H, =O, CHO, $OR^2$, $CH_2OR^2$, Cl, Br, F, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)$ $CH_2CH_3$, $CH(CH_3)_3$, —CN, $NO_2$, $NR^2R^{2a}$, $CH_2NR^2R^{2a}$, $C(O)R^{2c}$, $CH_2C(O)R^{2c}$, $NR^2C(O)R^{2b}$, $C(O)NR^2R^{2a}$, $SO_2NR^2R^{2a}$, $S(O)_pR^5$, and $CF_3$;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, benzyl, $C_{3-6}$ carbocycle substituted with 0–2 $R^{4b}$, a $C_{3-6}$ carbocycle-$CH_2$— substituted with 0–2 $R^{4b}$, and 5–6 membered heterocycle containing from 1–4 heteroatoms selected from the group consisting of N, O, and S, substituted with 0–2 $R^{4b}$;

alternatively, when $R^2$ is attached to an amino nitrogen, then $R^2$ is an amine protecting group;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, benzyl, $C_{3-6}$ carbocycle substituted with 0–2 $R^{4b}$, and 5–6 membered heterocycle containing from 1–4 heteroatoms selected from the group consisting of N, O, and S, substituted with 0–2 $R^{4b}$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, benzyl, $C_{3-6}$ carbocycle substituted with 0–2 $R^{4b}$, and 5–6 membered heterocycle containing from 1–4 heteroatoms selected from the group consisting of N, O, and S, substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, benzyl, $C_{3-6}$ carbocycle substituted with 0–2 $R^{4b}$, and 5–6 membered heterocycle containing from 1–4 heteroatoms selected from the group consisting of N, O, and S, substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^{4b}$, at each occurrence, is selected from H, =O, $OR^3$, $CH_2OR^3$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)$ $CH_2CH_3$, $CH(CH_3)_3$, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C$ $(O)R^{3a}$, $C(O)NR^3R^{3a}$, $SO_2NR^3R^{3a}$, $S(O)_p$—$C_{1-4}$ alkyl, $S(O)_p$-phenyl, and $CF_3$;

$R^5$, at each occurrence, is selected from $CF_3$, $CH_3$, $CH_2CH_3$, $CH_2CH_2CH_3$, $CH(CH_3)_2$, $CH_2CH_2CH_2CH_3$, $CH_2CH$ $(CH_3)_2$, $CH(CH_3)CH_2CH_3$, $CH(CH_3)_3$, phenyl substituted with 0–2 $R^6$, and benzyl substituted with 0–2 $R^6$;

$R^6$, at each occurrence, is selected from H, OH, $OR^2$, $CH_2OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)$ $CH_2CH_3$, $CH(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $SO_2NR^2R^{2a}$, $NR^2SO_2NR^2R^{2a}$, and $NR^2SO_2C_{1-4}$ alkyl; and, p, at each occurrence, is selected from 0, 1, and 2.

[18] In another preferred embodiment, the present invention provides a novel compound wherein:

$NR^1R^2$ is selected from morpholino, pyrrolidino, and piperidino;

$R^{1a}$ is selected from $CF_3$, $S(O)_2CH_3$, and $C(O)NH_2$;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

$B^1$ is selected from the group: 2-(aminosulfonyl)phenyl, 2-(methylsulfonyl)phenyl, 1-pyrrolidinocarbonyl, 2-(methylsulfonyl)phenyl, 2-(N,N-dimethylaminomethyl)phenyl, 2-(N-methylaminomethyl)phenyl, 2-(N-ethyl-N-methylaminomethyl)phenyl, 2-(N- pyrrolidinylmethyl)phenyl, 1-methyl-2-imidazolyl, 2-methyl-1-imidazolyl, 2-(dimethylaminomethyl)-1-imidazolyl, 2-(methylaminomethyl)-1-imidazolyl, 2-(N-(cyclopropylmethyl)aminomethyl)phenyl, 2-(N-(cyclobutyl)aminomethyl)phenyl, 2-(N-(cyclopentyl) aminomethyl)phenyl, 2-(N-(4-hydroxypiperidinyl) methyl)phenyl, and 2-(N-(3-hydroxypyrrolidinyl)methyl) phenyl; and, alternatively, $B^1$ is selected from the group: 2-(N-Pg-N-methylaminomethyl)phenyl, 2-(N-Pg-N-methylaminomethyl)-1-imidazolyl, 2-(N-Pg-N-(cyclopropylmethyl)aminomethyl)phenyl, 2-(N-Pg-N-(cyclobutyl)aminomethyl)phenyl, and 2-(N-Pg-N-(cyclopentyl)aminomethyl)phenyl.

[19] In another preferred embodiment, the present invention provides a novel compound of formula IIIa:

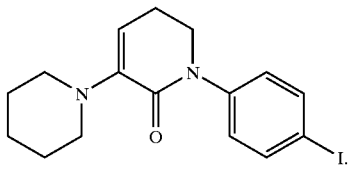

IIIa

[20] In another preferred embodiment, the present invention provides a novel compound of formula IIIb:

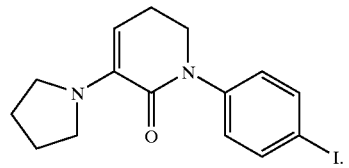

IIIb

Definitions

The present invention can be practiced on multigram scale, kilogram scale, multikilogram scale, or industrial scale. Multigram scale, as used herein, is preferable in the sale wherein at least one starting material is present in 10 grams or more, more preferable at least 05 grams or more, even more preferably at least 100 grams or more. Multikilogram scale, as used herein, is intended to mean the scale wherein more than one kilo of at least one starting material is used. Industrial scale as used herein is intended to mean a scale which is other than a laboratory sale and which is sufficient to supply product sufficient for either clinical tests or distribution to consumers.

As used herein, equivalents are intended to mean molar equivalents unless otherwise specified.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. Tautomers of compounds shown or described herein are considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present invention is also intended to include all stable oxides of thiol and amino groups, even when not specifically written. When an amino group is listed as a substituent, the N-oxide derivative of the amino group is also included as a substituent. When a thiol group is present, the S-oxide and S,S-dioxide derivatives are also included.

When any variable (e.g., $R^6$) occurs more than one time in any constituent or formula for a compound, its definition at each occurrence is independent of its definition at every other occurrence. Thus, for example, if a group is substituted with 0–2 $R^6$, then the group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, the term "amino protecting group" (or "N-protected") refers to any group known in the art of organic synthesis for the protection of amine groups. As used herein, the term "amino protecting group reagent" refers to any reagent known in the art of organic synthesis for the protection of amine groups that may be reacted with an amine to provide an amine protected with an amine-protecting group. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York, (1981), the disclosure of which is hereby incorporated by reference. Examples of amine protecting groups include, but are not limited to, the following: 1) acyl types such as formyl, trifluoroacetyl (TFA), phthalyl, and p-toluenesulfonyl; 2) aromatic carbamate types such as benzyloxycarbonyl (cbz) and substituted benzyloxycarbonyls, 2-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

Amine protecting groups may include, but are not limited to the following: 2,7-di-t-butyl-[9-(10,10-dioxo-10,10,10, 10-tetrahydrothio-xanthyl)]methyloxycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl)ethyloxycarbonyl; benzyloxycarbonyl; p-nitrobenzyloxy- carbonyl; 2-(p-toluenesulfonyl) ethyloxycarbonyl; m-chloro-p-acyloxybenzyloxycarbonyl; 5-benzyisoxazolylmethyl- oxycrbonyl; p-(dihydroxyboryl) benzyloxycarbonyl; m-nitrophenyloxycarbonyl; o-nitrobenzyloxycarbonyl; 3,5-dimethoxybenzyloxycrbonyl; 3,4-dimethoxy-6-nitrobenzyloxycarbonyl; N'-p-toluenesulfonylaminocarbo- nyl; t-amyloxycarbonyl; p-decyloxybenzyloxycarbonyl; diisopropylmethyloxycarbonyl; 2,2-dimethoxycarbonyl- vinyloxycarbonyl; di(2-pyridyl)methyloxycarbonyl; 2-furanylmethyloxycarbonyl; phthalimide; dithiasuccinimide; 2,5-dimethylpyrrole; benzyl; 5-dibenzylsuberyl; triphenylmethyl; benzylidene; diphenylmethylene; and, methanesulfonamide.

As used herein, "alkyl" is intended to include both branched and straight-chain saturated aliphatic hydrocarbon groups having the specified number of carbon atoms. $C_{1-10}$ alkyl, is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-10}$ alkenyl is intended to include $C_2$, $C_3$, $C_4$, $C_5$, $C_6$, $C_7$, $C_8$, $C_9$, and $C_{10}$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-10}$ Alkynyl is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "heterocycle" is intended to mean a stable 5, 6, or 7-membered monocyclic or bicyclic or 7, 8, 9, 10, 11, or 12-membered bicyclic or tricyclic heterocyclic ring which is saturated, partially unsaturated or unsaturated (aromatic), and which consists of carbon atoms and 1, 2, 3, or 4 heteroatoms independently selected from the group consisting of N, O, and S and including any bicyclic group in which any of the above-defined heterocyclic rings is fused to a benzene ring. The nitrogen and sulfur heteroatoms may optionally be oxidized. The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O, and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p 1445, the disclosure of which is hereby incorporated by reference.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

Synthesis

By way of example and without limitation, the present invention may be further understood by the following schemes and descriptions.

Preparation of dipolarophiles

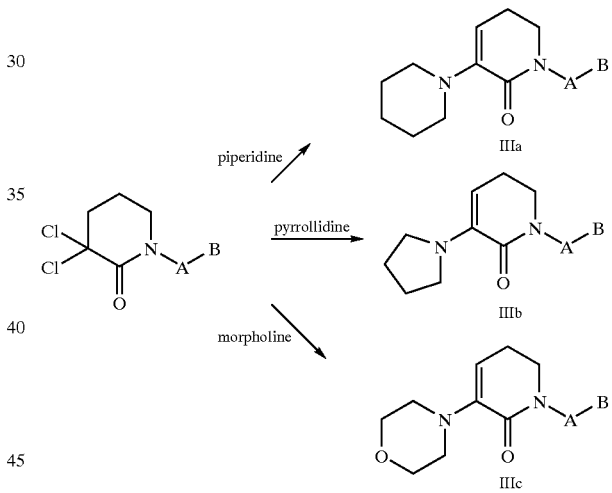

Dipoloarphiles IIIa–IIIc can be formed by reacting their corresponding cyclic amine precursors (e.g., piperidine, pyrrolidine, or morpholine) with an appropriate α,α-dichlorolactam (e.g., N-4-iodophenyl-3,3-dichloropiperidin-2-one). Preferably, the reaction is conducted in the presence of an excess of the desired cyclic amine. The excess cyclic amine can be solvent, reactant, and base. Preferably, this condensation is conducted at the reflux temperature of the cyclic amine. When B is a group other than $B^1$ (i.e., B is selected from Cl, Br, I, OMs, OTs, $OSO_2Ph$, $CH_2Br$, $CH_2OH$, and CHO), then the dipolarophile can be modified to contain $B^1$. For example, Suzuki coupling can be used to replace a leaving group (e.g., Br or I) with an aromatic $B^1$ (e.g., benzaldehyde). If the $B^1$ has a sensitive functionality (e.g., an amino group), then it can be protected prior to the cycloaddition reaction.

Reaction (a): 1,3-Dipolar cycloaddition

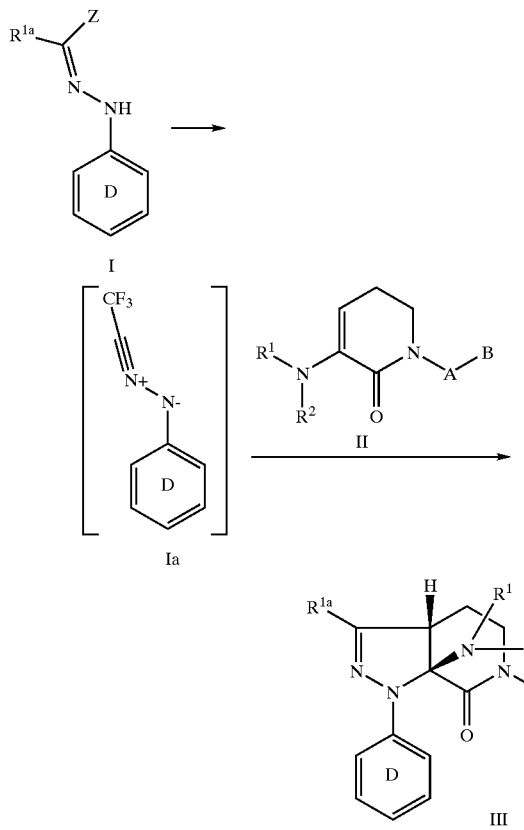

The 1,3-dipolar cycloaddition reaction of the present invention involves reaction between an in situ generated nitrileimine (Ia, 1,3-dipole) and a dipolarophile (II). This cycloaddition reaction regiospecifically generates the corresponding fused pyrazoline (III). Aprotic solvents (e.g., toluene, THF, and DME) can be used. The preferred solvent for the cycloaddition reaction is toluene.

Hydrazone (I) can first be contacted with the base or dipolarophile (II), followed by addition of the second component. For example, dipolarophile (II) can be contacted with hydrazone (I) and addition of the base can then follow. When this order is used, it is expected that the 1,3-dipole is generated in the presence of the dipolarophile. Alternatively, the hydrazone (I) can be contacted with a base and addition of dipolarophile (II) can then follow.

Generation of nitrileimine 1,3-dipole (Ia) can be achieved by reacting a base with its hydrazone precursor (I). Bases such as trialkyamines (e.g., triethylamine and diisopropylethylamine) or cyclic tertiary amines (e.g., N-methylmorpholine) can be used. The preferred base is a trialkylamine, such as triethylamine, or a cyclic tertiary amine, such as N-methylmorpholine (NMM). Preferably, about 1 to 3 equivalents of base are used. Even more preferably, about 1.5 to 2.5 equivalents of base are used.

Factors like the reactivities of 1,3-dipole precursors (I) and dipolarophiles (II) can affect the cycloaddition reaction rate. Therefore, the reaction temperature and time may be varied. Qualitatively, the order of the reactivity of the 1,3-dipole precursors (I) is: hydrazonoyl mesylate>hydrazonoyl bromide, tosylate, benzenesulfonate>>hydrazonoyl chloride. When a hydrzonoyl chloride is used, then the reaction is preferably run at an elevated temperature (e.g., refluxing THF). However, when a more reactive hydrazone is used (e.g., mesylate), then the reaction can be performed near room temperature (e.g., 5–25° C.).

The presence of the amino group (i.e., $NR^1R^2$) on the dipolarophile (II) has been found to be advantageous. Compared to cycloadditions with dipolarophiles not having the amino group, the above cycloaddition can be conducted at lower temperatures and provides higher yields. Preferably, the amino group is morpholino.

When the amine is morpholine, the base is preferably NMM, preferably about 2 equivalents of based are present, the solvent is preferably toluene, and the reaction is preferably run at from 5–25° C. When the amine is pyrrolidine, the base is preferably NMM, preferably about 2 equivalents of base are present, the solvent is preferably toluene, and the reaction is preferably run at from 5–25° C. When the amine is piperidine, the base is preferably NMM, preferably about 2 equivalents of base are present, the solvent is preferably toluene, and the reaction is preferably run at from 5–25° C.

Reaction (b): Pyrazolo-pyridinone formation

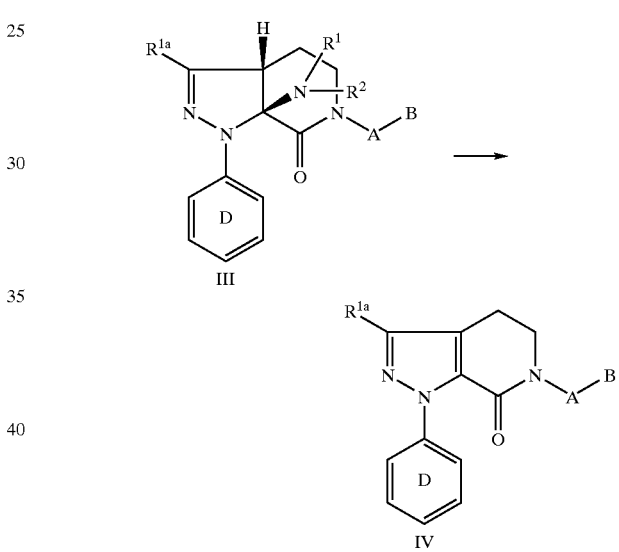

Fused pyrazoline (III) can be converted to its corresponding pyrazole-pyridinone (IV) by treatment with an acid. This deamination reaction is preferably performed in the presence of a strong acid (e.g., trifluoroacetic acid (TFA), sulfuric acid nitric acid, and hydrochloric acid (HCl)). An aprotic solvent may be used (e.g., $CH_2Cl_2$ or THF). As one of ordinary skill in the art recognizes, some acids are usually available in the presence of a second solvent. For example, 6N HCl can be available in isopropyl alcohol (IPA). 2N HCl can be available as an aqueous solution. Thus, the second solvent, if present, will depend on the acid used. Preferably, the second solvent is isopropyl alcohol or water. The reaction can be conducted from about 5° C. to reflux of the solvent. Preferably, when TFA, either neat or in $CH_2Cl_2$, is used, the reaction is conducted at a temperature of from 5° C. to room temperature (approximately 25° C.). Preferably, when HCl (e.g., 2N or 6N) is used, the reaction solvent is THF and the reaction is conducted at about the reflux temperature of THF. Preferred acids or acid solvent combinations are: TFA (neat), TFA/$CH_2Cl_2$, 6N HCl/isopropyl alcohol/THF, and 2N HCl/water/THF.

Reaction (c1): Converting Ring D to an Aminobenzisoxazole Ring

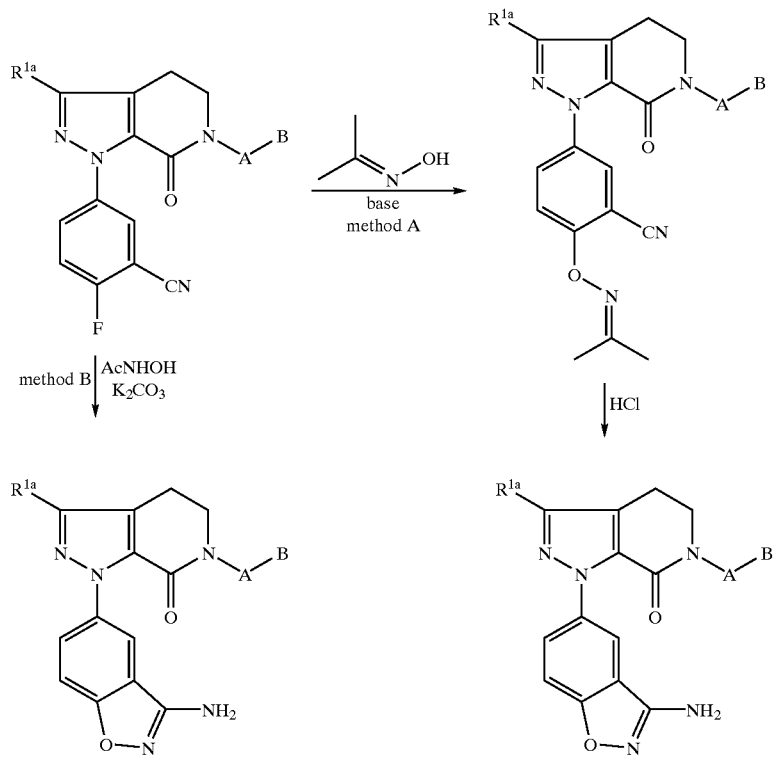

Converting of the ortho fluoro/cyano substituents to the corresponding aminobenzisoxazole functionality in ring D can be achieved in two preferred ways. The first preferred method involves a two-step sequential reaction. Substitution of the fluoro functionality ortho to the cyano group with an acetone oxime in the existence of a base, such as potassium tert-butoxide or NaH, in anhydrous solvent, such as THF or DMF, generates the corresponding acetone oxime substituted intermediate. This intermediate is subsequently converted into the desired aminobenzisoxazole ring by treating with an acid. About 2–4 equivalents of acetone oxime are used for this substituted reaction. The preferred base is sodium hydride. Anhydrous DMF is the preferred solvent. At 0–25° C., the substitution reaction is complete in 1–2 h.

The second preferred method involves a one-step reaction between fluoro/cyano-substituted substrate and an acetohydroxamic acid. Potassium carbonate is preferably used as the base to promote the reaction. Normally, 5–10 equivalents of potassium carbonate are used for the reaction. The preferred solvent system is a mixture of DMF and water in a volume ratio 10–15 to 1. The reaction is preferably conducted at 20–30° C. At such a temperature range, the reaction is usually complete in 10–15 h.

Reaction (c2): Converting Ring D to a benzyl amine or amino-benzisoxazole

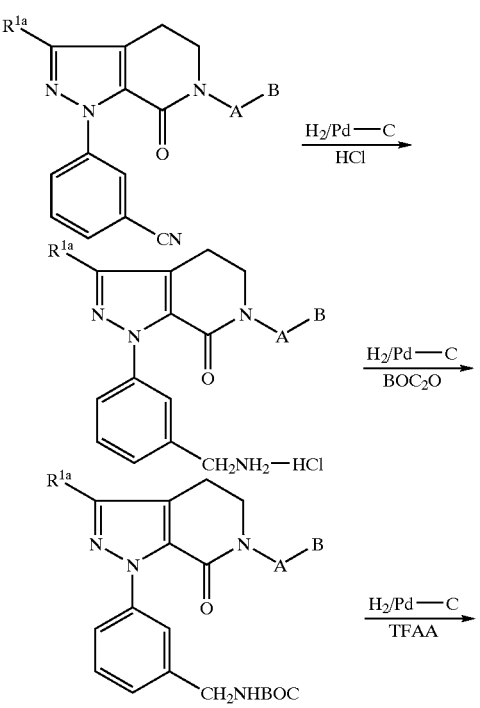

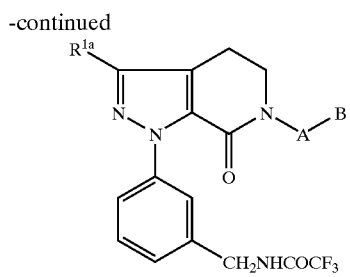

Reduction of the cyano group to a benzylamine can be achieved with a chemical reducing reagent, such as $NaBH_4$, or via Pd(0) catalyzed hydrogenation. The preferred reduction procedure is palladium-catalyzed hydrogenation. About 1–2% (weight) of the palladium on charcoal (5% or 10%) can be used. The preferred solvent for the hydrogenation reaction is ethanol. The reaction is normally run at 20–25° C. Usually, the reaction is complete in 4–6 h at 20–25° C. under 50–55 psig hydrogen pressure. When the reaction is conducted in the existence of an acid, such as hydrochloric acid (HCl), the corresponding salt, such as benzylamine hydrochloride salt, is obtained. When the reduction reaction is conducted in the existence of an electrophile that is used for the in situ protection of the generated benzylamine, such as di-tert-butyl dicarbonate ($Boc_2O$) or trifluoroacetic acid anhydride (TFAA), the corresponding protected benzylamine (Boc or TFA) is obtained.

Preferably, a Suzuki coupling is used to attach a $B^1$ group to A, when is a leaving group. The Pd(0) catalyst used in the above Suzuki coupling is preferably $Pd(PPh_3)_4$. About 1–5% equivalents of the catalyst are used to catalyze this coupling reaction with 2% being preferred. About 1.0–1.5 equivalents of an arylboronic acid are used, with 1–2 equivalents being preferred. A base is used to promote the Suzuki coupling reaction. The preferred base is an inorganic salt, such as potassium carbonate or sodium carbonate. The most preferred base is sodium carbonate. A mixed solvent system is used for this Suzuki coupling reaction. The preferred solvent system is toluene/ethanol/water (2–4:1:1 v/v/v). Preferably the reaction is run at elevated temperature, the preferred temperature range being 70–80° C. Usually, the reaction is complete in 4–20 h at 70–80° C. Preferably, the aryl group is benzaldehyde.

If it is desired to couple a non-aryl $B^1$ (e.g., piperidin-2-one) or attach a heterocycle to A via a nitrogen (e.g., 1-imidazolyl), then a nucleophilic substitution reaction is preferably used. This type of reaction is preferably run in the presence of a tertiary amine base (e.g., triethylamine) or an inorganic base (e.g., potassium carbonate or cesium carbonate). In addition, a phase transfer catalyst can also be used. Preferably, when a lactam is being attached, an Ullmann-type coupling is performed using a copper catalyst (e.g., $Cu(PPh_3)_3Br$).

Reaction (c3): Conversion of B to $B^1$

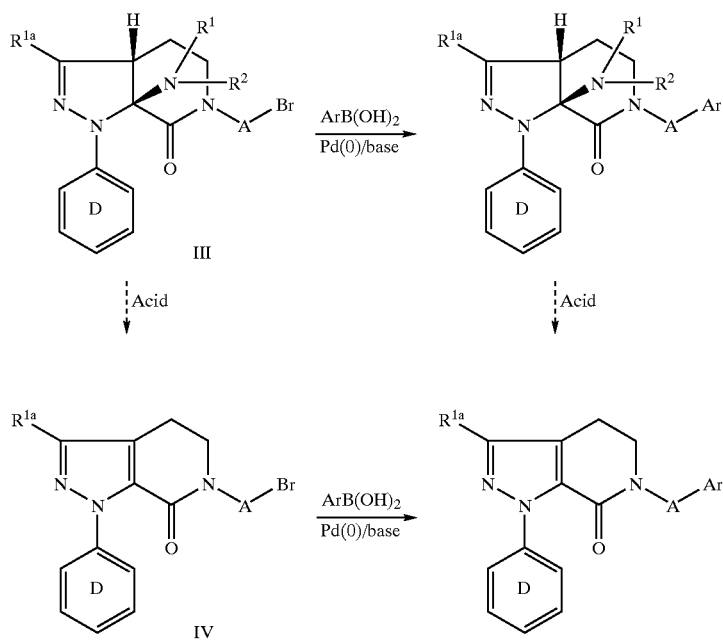

Reaction (c3a): Oxidation of Thiomethyl (—SMe) functionality to Sulfone (—SO₂Me)

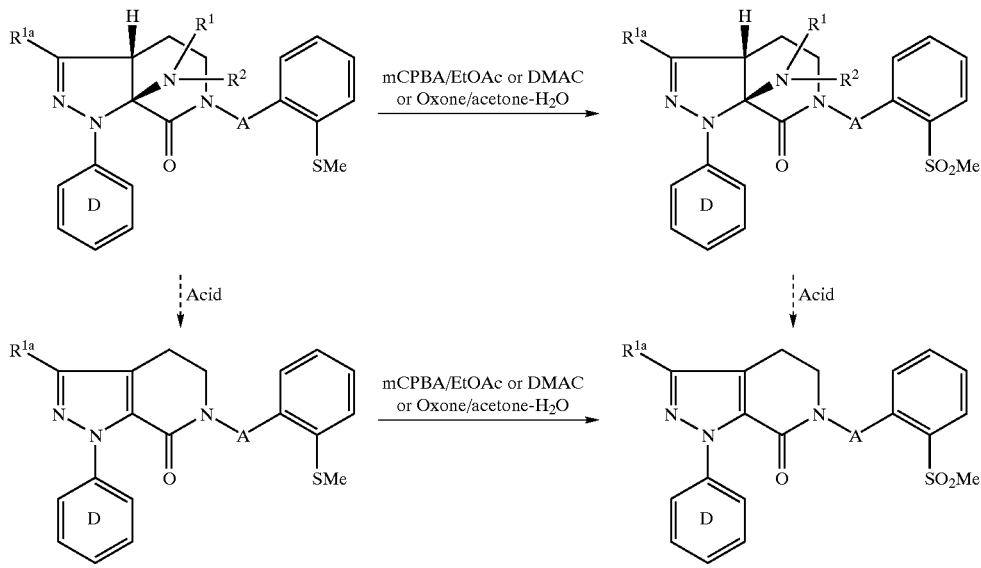

A selected class of oxidation reagents can be used to oxidize the thiomethyl (—SMe) functionality to the corresponding sulfone (—SO₂Me). The preferred oxidants are mCPBA and Oxone®. About 2–10 equivalents of mCPBA or Oxone® are used to do this oxidation reaction, with 2–5 eqivalents being preferred. Several different solvents or solvent systems are used for this oxidation reaction. The choice for the solvent or solvent system is dependent on the oxidant used for the reaction. With mCPBA as an oxidant, ethyl acetate (EtOAc) is preferred. With Oxone® as an oxidant, the preferred solvent system is a mixture of acetone and water in a volume ratio of one to one. The oxidation reaction can be run at 25–50° C., depending on the oxidant used for the reaction. With mCPBA as an oxidant, the oxidation reaction can be run at room temperature (20–25° C.). But, when Oxone® is used as an oxidant, the reaction is run at elevated temperature, the preferred temperature range being 40–50° C. Generally, the reaction is complete in 5–20 h at 20–50° C.

Reaction (c4): Protection Group Removal: Removing Boc protection group to the corresponding benzylamine

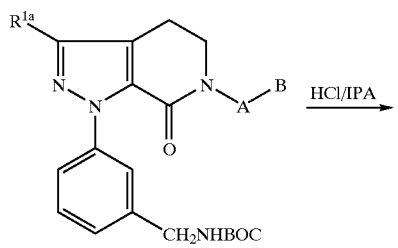 HCl/IPA

-continued

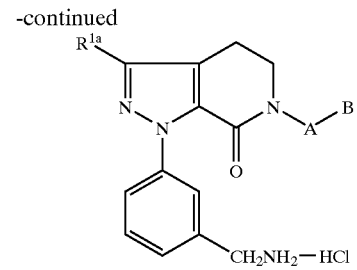

The Boc protection group is removed to release the corresponding benzylamine by treating the N-Boc benzylamine with an acid. The typical acid used for this deprotection reaction is hydrochloric acid (HCl). The preferred HCl form is 5 to 6 N HCl solution in isopropyl alcohol. By treatment the corresponding Boc protected benzylamine with excess amount of HCl solution in isopropyl alcohol at 20–25° C. for several hours, the corresponding benzylamine hydrochloride salt is generated. Normally, 1–5 equivalents of HCl solution in isopropyl alcohol are used.

Trifluoroacetic acid (TFA) is also useful to remove the Boc group. The resulting deprotection product is the corresponding benzylamine trifluoroacetic acid salt. Normally, the excess amount of trifluoroacetic acid is used. The deprotection reaction is also run at 20–25° C. The reaction is usually complete in 2–10 h.

One of ordinary skill in the art would recognize that the acid used in reaction (b) could not only deaminate, but also deprotect. Therefore, (c4) may be unnecessary in view of (b).

Reaction (c4): Protection Group Removal: Removing TFA Protection Group from a Benzylamine

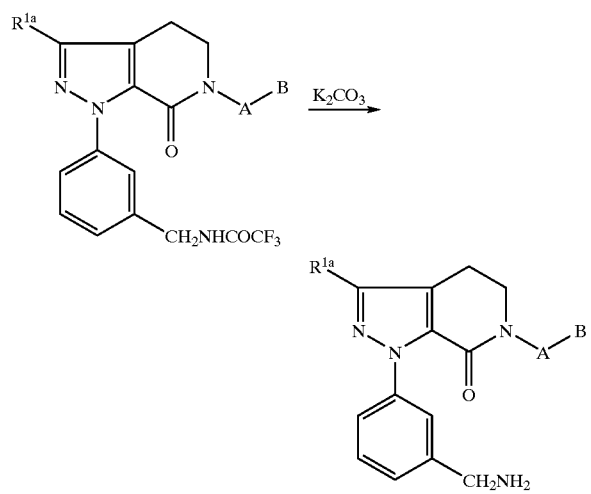

Trifluoroacetyl protection group of benzylamine is removed by treating the corresponding TFA protected benzylamine with an inorganic base, such as sodium hydroxide or potassium hydroxide, or an inorganic salt, such as potassium carbonate. The preferred base is potassium carbonate. Normally, 1 to 4 equivalents of potassium carbonate are used for the reaction. Alkyl alcohol, such as methanol or ethanol, is used as solvent. The reaction is run at 20–60° C. The preferred temperature range is 50–60° C. Normally, the reaction is complete in 2 to 10 h at 50–60° C. The deprotection reaction under such a condition generates the corresponding benzylamine as a free base.

Reaction (c4): Protection Group Removal: Removing tert-Butyl Protection Group from a Sulfonamide

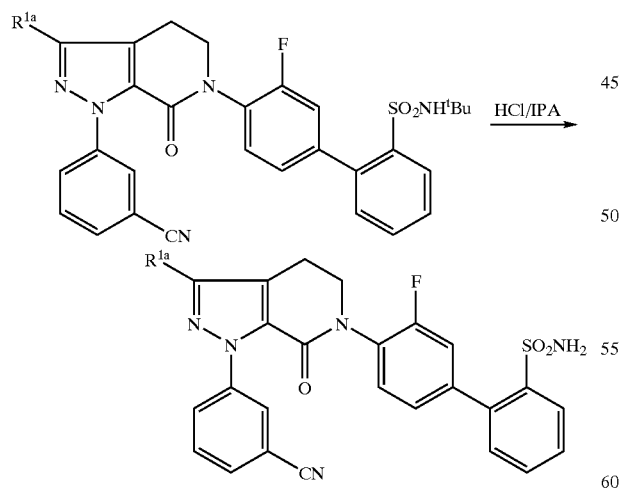

Removal of the tert-butyl group to release the corresponding sulfamide is also conducted in an acidic condition. The preferred acid used for this reaction is a 5 to 6 N hydrochloric acid solution in isopropyl alcohol. Normally, an excess of hydrogen chloride is employed. The isopropyl alcohol, which makes hydrogen chloride solution, is also a reaction solvent. The reaction is usually run at an elevated temperature. The preferred temperature range is 70–80° C. The reaction is usually complete in 30 to 50 hours at 70–80° C.

Reaction (c5): Addition of A—B

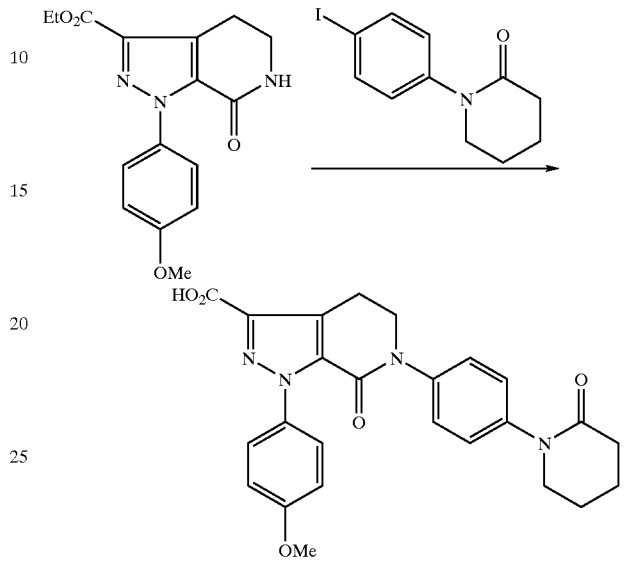

Addition of the A-B unit can be accomplished in a number of ways. Preferably, the A-B unit is attached via copper(I) mediated addition (e.g., CuI and 8-hydroxyquinoline). Preferably, a base is used (e.g., $K_2CO_3$). This reaction is preferably run in an aprotic solvent (e.g., DMSO) and is preferably heated to over 100° C.

It is to be noted that the A subunit could be attached followed attachment of the B subunit as described herein. It is preferred that the A-B unit is added as a whole piece.

Reaction (c6): Converting $R^{4a}$=CHO to $R^{4a}$ = aminomethyl

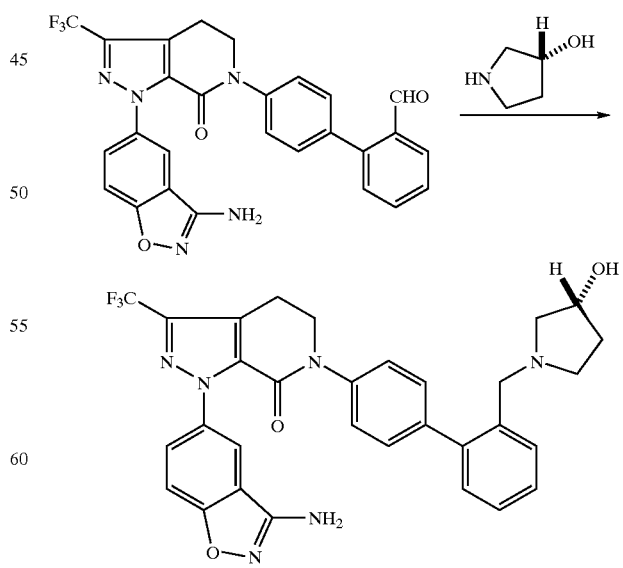

In reaction (c6), aminomethyl is intended to represent groups such as N,N-dimethylaminomethyl, N-methylaminomethyl, N-ethyl-N-methylaminomethyl, (N-pyrrolidinylmethyl), N-(cyclopropylmethyl) aminomethyl, N-(cyclobutyl)aminomethyl, N-(cyclopentyl) aminomethyl, N-(4-hydroxypiperidinyl)methyl, and N-(3-hydroxypyrrolidinyl)methyl. One of ordinary skill in the art would recognize that the aldehyde group could be manipulated into aminomethyl groups by a number of methods, including, for example, reductive amination to form a 3-hydroxypyrrolidinyl-methyl or methylamino-methyl group.

As shown above, a preferred pathway is to use reductive amination. This reaction is preferably run in a dipolar aprotic solvent (e.g., DMSO). Preferably, the aldehyde-containing compound is contacted with an amine (e.g., (3R)-3-hydroxypyrrolidine or N,N-dimethylamine). Usually, slightly more than one equivalent of amine is used (e.g., 1–1.5 equivalents, or 1.2 equivalents). Also, the amine is preferably used in a salt form (e.g., hydrochloride salt). After addition of the amine, a reducing agent is then added (e.g., NaB(OAc)$_3$H). Usually, slightly more than one equivalent of the reducing agent is used (e.g., 1–1.5 equivalents, or 1.2 equivalents). This reaction is preferably run at about room temperature. The reducing agent can be added in the presence of a second solvent, if desired.

When $R^{1a}$ is an ester, it can be converted to C(O)NH$_2$ by a number of ways known to those of skill in the art. A preferred pathway is to first treat the ester with an amine delivering agent (e.g., formamide, preferably in excess) and then contact this mixture with a strong base (e.g., sodium methoxide, preferably about 2 equivalents). This reaction is preferably run in a dipolar aprotic solvent (e.g., dimethylformamide). Preferably, the reaction is cool to about 0–5° C. prior to addition of the base. After addition of the base, the reaction is preferably warmed to room temperature. As one of ordinary skill in the art recognizes, some bases are usually available in the presence of a second solvent. For example, sodium methoxide can be in the presence of methanol. Thus, this reaction can be run in the presence of two solvents (e.g., dimethylformamide and methanol).

Other features of the invention will become apparent in the course of the following descriptions of examplary embodiments which are given for illustration of the invention and are not intended to be limiting thereof.

Reaction (c7): Converting $R^{1a}$ = CO$_2$H or CO$_2$-alkyl to $R^{1a}$ = amido group

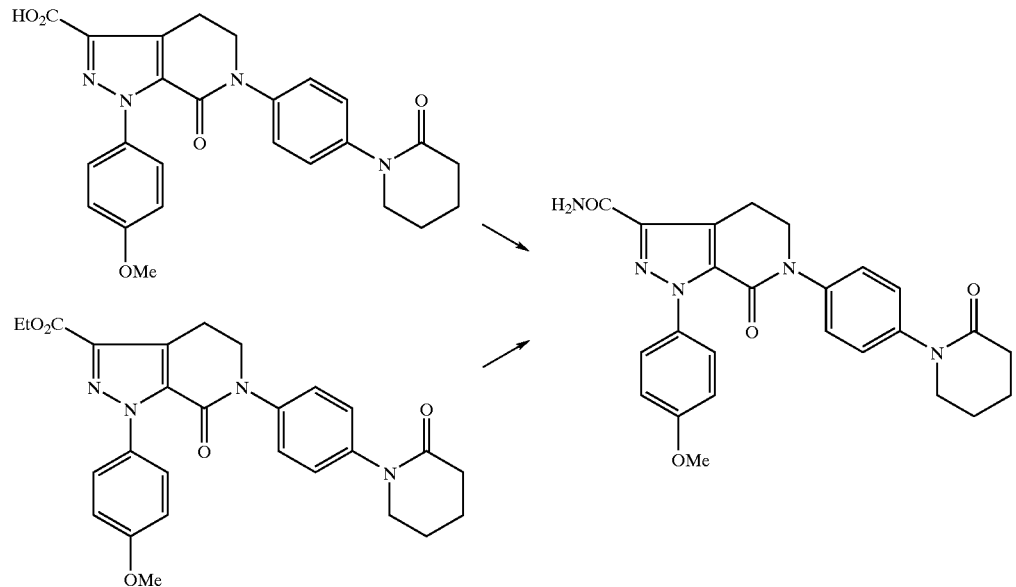

When $R^{1a}$=CO$_2$H, it can be converted to C(O)NH$_2$ by a number of ways known to those of skill in the art. A preferred pathway is to activate the acid and then contact it with an amine-delivering compound. For example, the acid group can be treated with a base (e.g., triethylamine, preferably more than 1 equivalent) and then with an activating agent (e.g., iso-butyl chloroformate, preferably more than 1 equivalent). The now activated acid can be treated with an amine delivering agent (e.g., ammonium hydroxide, preferably in excess) to form the amide. This reaction is preferably run at room temperature and in an aprotic solvent (e.g., ethyl acetate).

EXAMPLES

Example 1

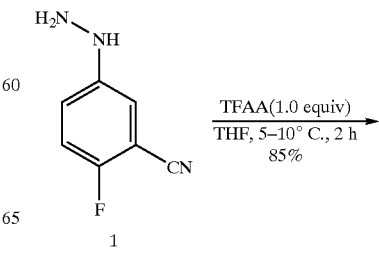

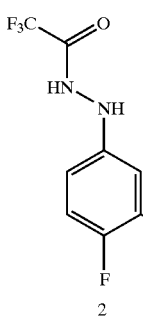

2

1-(3-Cyano-4-fluoro)phenyl-2-(trifluoroacetyl)hydrazine (2) A suspension of 4-fluoro-3-cyanophenylhydrazine (36.2 g, 0.24 mol) in anhydrous THF (200 mL) was treated dropwise with a solution of trifluoroacetic acid anhydride (TFAA, 50.4 g, 33.9 mL, 0.24 mol, 1.0 equiv) in anhydrous THF (35 mL) at 5–7° C. under $N_2$. The reaction mixture was then stirred at 5–15° C. for an additional 1 h. When HPLC showed the reaction was deemed complete, 150 mL of THF was removed in vacuo. The residual slurry was then treated with heptane (250 mL) with good stirring. The resulting solids were aged at room temperature for 1 h and then cooled down to 0–5° C. in an ice-bath for an additional 1 h. The off-white solids were collected by filtration, washed with heptane (2×50 mL), and dried at 40–45° C. in vacuo for 12 h to afford the crude, desired 1-(3-cyano-4-fluoro)phenyl-2-(trifluroacetyl)hydrazine (2, 50.4 g, 59.3 g theoretical, 85%), which was found to be pure enough to do the following reaction without further purification. For 2: CIMS m/z 246 ($M^+$–H, $C_9H_5F_4N_3O$).

Example 2

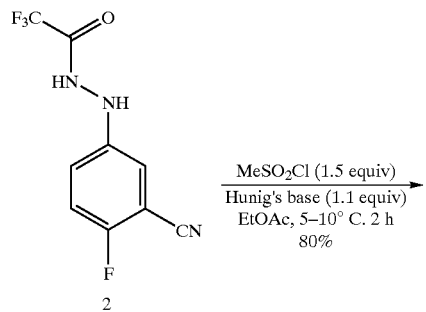

2,2,2-Trifluoro-N-(3-cyano-4-fluoro)phenylethanehydrazonoyl mesylate (3). A solution of 1-(3-cyano-4-fluoro)phenyl-2-(trifluoroacetyl)hydrazine (2, 12.4 g, 50 mmol) in ethyl acetate (100 mL) was treated with methanesulfonyl chloride (8.6 g, 5.8 mL, 75 mmol, 1.5 equiv) at 0–5° C. under $N_2$, and the resulting mixture was treated dropwise with N,N-diisopropylethylamine (Hunig's base, 7.1 g, 9.6 mL, 55 mmol, 1.1 equiv) at 0–5° C. under $N_2$. The reaction mixture was then stirred at 5–10° C. for an additional 1 h. When HPLC and TLC showed the reaction was deemed complete, the reaction mixture was treated with water (100 mL) and EtOAc (100 mL). The two layers were separated, and the aqueous layer was extracted with EtOAc (50 mL). The combined organic extracts were washed with water (2×50 mL) and saturated NaCl aqueous solution (50 mL), dried over $MgSO_4$, and concentrated in vacuo. The crude desired product was directly recrystallized out by direct titration of the residual ethyl acetate slurry (about 40 mL) with heptane (150 mL). The off-white solids were then collected by filtration to afford the crude, desired 2,2,2-trifluoro-N-(3-cyano-4-fluoro)phenylethanehydrazonyl mesylate (3, 12.96 g, 16.25 g theoretical, 80%), which was found to be essentially pure to do the following cycloaddition reaction without further purification. For 3, CIMS m/z 324 ($M^+$–H, $C_{10}H_7F_4N_3O_3S$).

Example 3

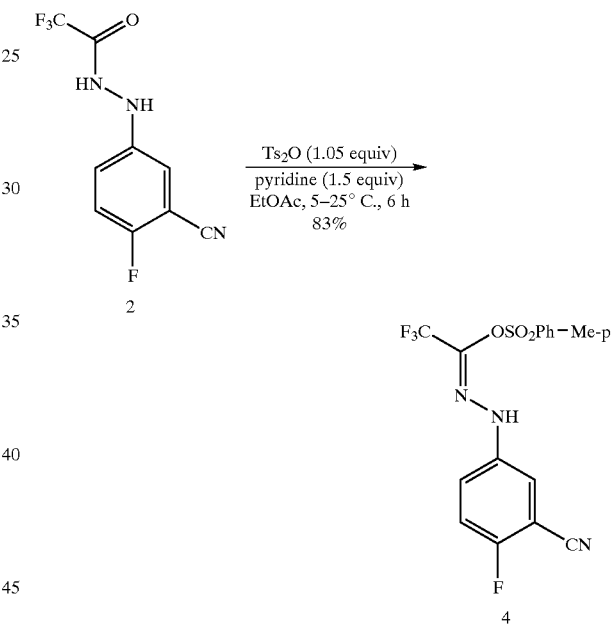

2,2,2-Trifluoro-N-(3-cyano-4-fluoro)phenylethanehydrazonoyl tosylate (4). A solution of 1-(3-cyano-4-fluoro)phenyl-2-(trifluoroacetyl)hydrazine (2, 12.34 g, 50 mmol) in ethyl acetate (100 mL) was treated with p-toluenesulfonyl anhydride (97% pure, 17.67 g, 52.5 mmol, 1.05 equiv) at 0° C. under $N_2$, and the resulting mixture was treated dropwise with pyridine (5.93 g, 6.1 mL, 75 mmol, 1.5 equiv) at 0° C. under $N_2$. The reaction mixture was then gradually warmed up to room temperature for 6 h. When HPLC and TLC showed the reaction was deemed complete, the reaction mixture was treated with water (100 mL) and EtOAc (100 mL). The two layers were separated, and the aqueous layer was extracted with EtOAc (50 mL). The combined organic extracts were washed with water (2×50 mL) and saturated NaCl aqueous solution (50 mL), dried over $MgSO_4$, and concentrated in vacuo. The crude desired product was directly recrystallized from 25% tert-butyl methyl ether (TBME)/heptanes (1:4 v/v) to afford the desired 2,2,2-trifluoro-N-(4-fluoro-3-cyano)

phenylethanehydrazonyl tosylate (4, 16.64 g, 20.05 g theoretical, 83%) as pale-yellow solids, which was found to be essentially pure to do the following cycloaddition reaction without further purification. For 4, CIMS m/z 400 (M$^+$–H, C$_{16}$H$_{11}$F$_4$N$_3$O$_3$S).

Example 4

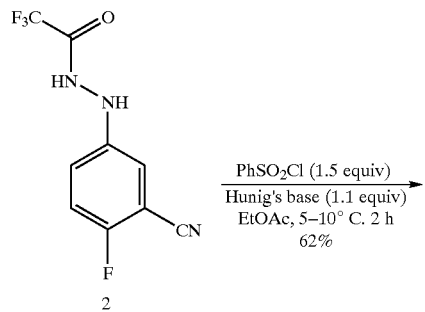

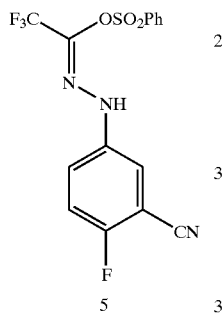

Example 5

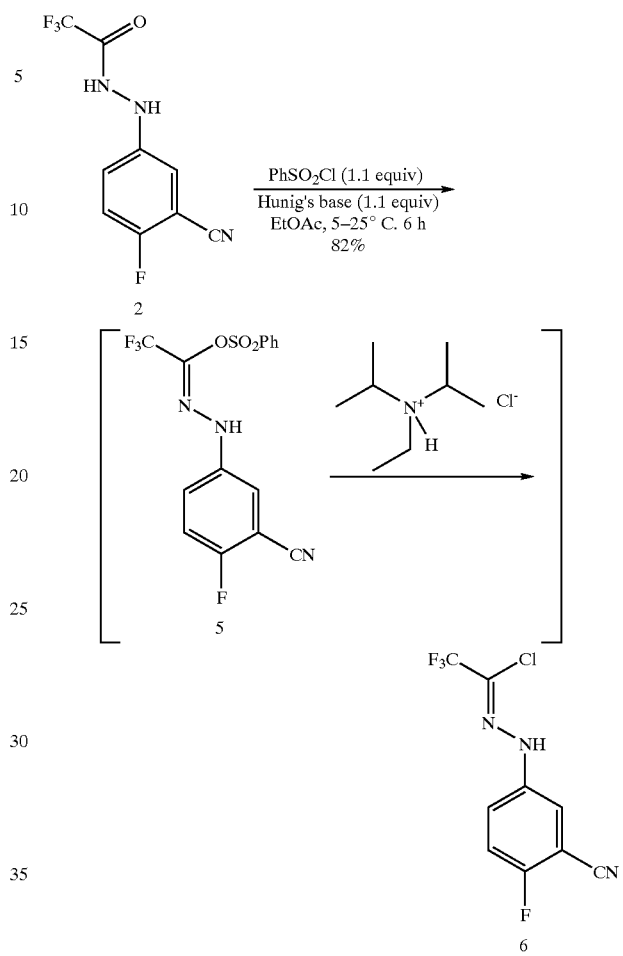

2,2,2-Trifluoro-N-(3-cyano-4-fluoro)phenylethanehydrazonoyl benzenesulfonate (5). A solution of 1-(3-cyano-4-fluoro)phenyl-2-(trifluoroacetyl)hydrazine (2, 12.4 g, 50 mmol) in ethyl acetate (100 mL) was treated with benzenesulfonyl chloride (13.2 g, 9.6 mL, 75 mmol, 1.5 equiv) at 0–5° C. under N$_2$, and the resulting mixture was treated dropwise with N,N-diisopropylethylamine (Hunig's base, 7.1 g, 9.6 mL, 55 mmol, 1.1 equiv) at 0–5° C. under N$_2$. The reaction mixture was then stirred at 5–10° C. for an additional 1 h before being warmed up to room temperature for 4 h. When HPLC and TLC showed the reaction was deemed complete, the reaction mixture was treated with water (100 mL) and EtOAc (100 mL). The two layers were separated, and the aqueous layer was extracted with EtOAc (50 mL). The combined organic extracts were washed with water (2×50 mL) and saturated NaCl aqueous solution (50 mL), dried over MgSO$_4$, and concentrated in vacuo. The residue was the purified by flash column chromatography (SiO$_2$, 10–30% EtOAc/hexane gradient elution) to afford the crude, desired 2,2,2-trifluoro-N-(3-cyano-4-fluoro) phenylethanehydrazonyl benzenesulfonate (5, 12.0 g, 19.4 g theoretical, 62%) as off-white solids, which was found to be essentially pure to do the following cycloaddition reaction without further purification. For 5, CIMS m/z 386 (M$^+$–H, C$_{15}$H$_9$F$_4$N$_3$O$_3$S).

2,2,2-Trifluoro-N-(3-cyano-4-fluoro)phenylethanehydrazonoyl chloride (6). A solution of 1-(3-cyano-4-fluoro)phenyl-2-(trifluoroacetyl)hydrazine (2, 12.4 g, 50 mmol) in ethyl acetate (100 mL) was treated with benzenesulfonyl chloride (9.7 g, 7.0 mL, 55 mmol, 1.1 equiv) at 0–5° C. under N$_2$, and the resulting mixture was treated dropwise with N,N-diisopropylethylamine (Hunig's base, 7.1 g, 9.6 mL, 55 mmol, 1.1 equiv) at 0–5° C. under N$_2$. The reaction mixture was then stirred at 5–10° C. for an additional 1 h before being warmed up to room temperature for an additional 5 h. When HPLC and TLC showed the reaction was deemed complete, the reaction mixture was treated with water (100 mL) and EtOAc (100 mL). The two layers were separated, and the aqueous layer was extracted with EtOAc (50 mL). The combined organic extracts were washed with water (2×50 mL) and saturated NaCl aqueous solution (50 mL), dried over MgSO$_4$, and concentrated in vacuo. The crude desired product was directly recrystallized out by direct titration of the residual ethyl acetate slurry (about 40 mL) with heptane (150 mL). The off-white solids were then collected by filtration to afford the crude, desired 2,2,2-Trifluoro-N-(3-cyano-4-fluoro)phenylethanehydrazonyl chloride (6, 10.88 g, 13.28 g theoretical, 82%), which was found to be essentially pure to do the following cycloaddition reaction without further purification. For 6, CIMS m/z 264/266 (M$^+$–H, C$_9$H$_4$ClF$_4$N$_3$).

Example 6

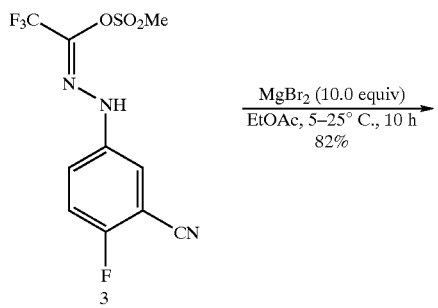

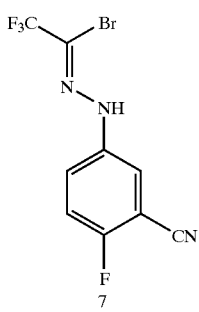

2,2,2-Trifluoro-N-(3-cyano-4-fluoro)phenylethanehydrazonoyl bromide (7). A solution of 2,2,2-trifluoro-N-(3-cyano-4-fluoro)phenylethanehydrazonoyl mesylate (3, 3.25 g, 10.0 mmol) in anhydrous THF (50 mL) was treated with magnesium bromide (MgBr$_2$, 18.4 g, 0.1 mol, 10.0 equiv) at room temperature, and the resulting reaction mixture was stirred at room temperature for an additional 10 h. When HPLC and TLC showed the reaction was deemed complete, the reaction mixture was treated with water (100 mL) and EtOAc (100 mL). The two layers were separated, and the aqueous layer was extracted with EtOAc (50 mL). The combined organic extracts were washed with water (2×50 mL) and saturated NaCl aqueous solution (50 mL), dried over MgSO$_4$, and concentrated in vacuo. The residue was the purified by flash column chromatography (SiO$_2$, 5–20% EtOAc/hexane gradient elution) to afford the desired 2,2,2-trifluoro-N-(3-cyano-4-fluoro)phenylethanehydrazonyl bromide (7, 2.54 g, 3.10 g theoretical, 82%) as off-white solids, which was found to be essentially pure to do the following cycloaddition reaction without further purification. For 7, CIMS m/z 308/310 (M$^+$–H, C$_9$H$_4$F$_4$BrN$_3$).

Example 7

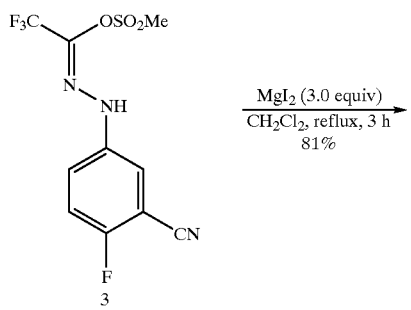

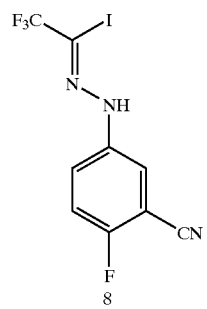

2,2,2-Trifluoro-N-(3-cyano-4-fluoro)phenylethanehydrazonoyl iodide (8). A solution of 2,2,2-trifluoro-N-(3-cyano-4-fluoro)phenylethanehydrazonoyl mesylate (3, 3.25 g, 10.0 mmol) in methylenechloride (CH$_2$Cl$_2$, 50 mL) was treated with magnesium iodide (MgI$_2$, 8.34 g, 30 mmol, 3.0 equiv) at room temperature, and the resulting reaction mixture was warmed to reflux for 3 h. When HPLC and TLC showed the reaction was deemed complete, the reaction mixture was treated with saturated sodium metabisulfite aqueous solution (100 mL) and CH$_2$Cl$_2$ (100 mL). The two layers were separated, and the aqueous layer was extracted with CH$_2$Cl$_2$ (50 mL). The combined organic extracts were washed with water (2×50 mL) and saturated NaCl aqueous solution (50 mL), dried over MgSO$_4$, and concentrated in vacuo. The residue was the purified by flash column chromatography (SiO$_2$, 5–20% EtOAc/hexane gradient elution) to afford the desired 2,2,2-trifluoro-N-(3-cyano-4-fluoro) phenylethanehydrazonyl iodide (8, 2.89 g, 3.57 g theoretical, 81%), which was found to be essentially pure to do the following cycloaddition reaction without further purification. For 8, CIMS m/z 356 (M$^+$–H, C$_9$H$_4$F$_4$IN$_3$).

Example 8

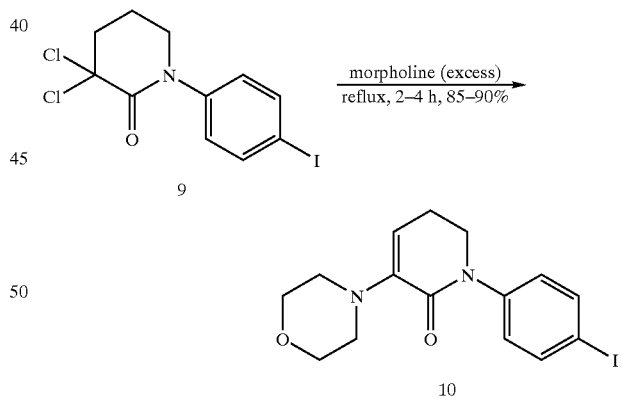

N-(4-Iodo)phenyl-3-morpholino-5,6-dihydro-2H-pyridin-2-one (10). A suspension of the crude α,α-dichlorolactam (9, 33.5 g, 90.5 mmol) in morpholine (100 mL) was warmed to reflux (130° C.) for 2 h. When HPLC showed the enamine lactam formation reaction was complete, the reaction mixture was cooled down to 80° C. The solid morpholine hydrogen chloride salt was precipitated out from the reaction mixture at 80° C. Water (20 mL) was introduced to the reaction mixture at 80° C., and the resulting solution was further cooled down to 5–10° C. (ice bath). Water (200 mL) was then added dropwise to the cooled reaction mixture at 5–10° C. with good stirring. The bright yellow to off-white solids were precipitated out immediately from the reaction mixture after addition of water. The initial addition rate should be well controlled to avoid large solid mass generation. The mixture was kept stirring for an additional 30 min at 5–10° C. before the solids were collected by filtration. The solids were washed with water (2×50 mL) and heptane (50 mL) and dried in vacuo at 50–60° C. for 24 h to constant weight. The crude, desired product (10, 29.9 g, 34.8 g theoretical, 86%) was obtained as light-yellow crystals, which were found to be essentially pure by HPLC and was directly employed in the following reaction without further purification. For 10, CIMS m/z 385 ($M^++H$, $C_{15}H_{17}IN_2O_2$).

Example 9

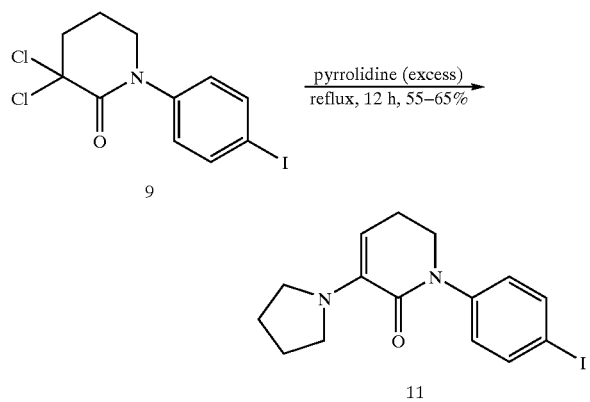

N-(4-Iodo)phenyl-3-pyrrolidino-5,6-dihydro-2H-pyridin-2-one (11). A suspension of the crude α,α-dichlorolactam (9, 10.0 g, 27 mmol) in pyrrolidine (100 mL) was warmed to reflux (87–88° C.) for 12 h. When HPLC showed the enamine lactam formation reaction was complete, the reaction mixture was cooled down to 5–10° C. Water (100 mL) and ethyl acetate (100 mL) were then added to the reaction mixture at 5–10° C. with good stirring. The two layers were separated, and the aqueous layer was extracted with EtOAc (50 mL). The combined organic extracts were washed with 2% of citric acid aqueous solution (4×50 mL), water (2×50 mL), and saturated NaCl aqueous solution (50 mL), dried over MgSO$_4$, and concentrated in vacuo. The residue was the purified by flash column chromatography (SiO$_2$, 20–60% EtOAc/hexane gradient elution) to afford desired product (11, 5.56 g, 9.94 g theoretical, 56%) was obtained as off-white solids, which was found to be essentially pure by HPLC and was directly employed in the following reaction without further purification. For 11, CIMS m/z 369 ($M^++H$, $C_{15}H_{17}IN_2O$).

Example 10

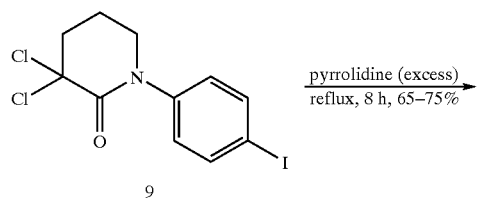

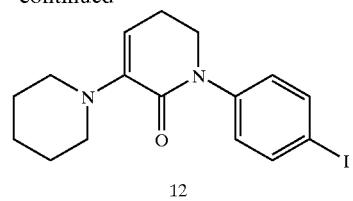

N-(4-Iodo)phenyl-3-piperidino-5,6-dihydro-2H-pyridin-2-one (12). A suspension of the crude α,α-dichlorolactam (9, 3.70 g, 10 mmol) in piperidine (30 mL) was warmed to reflux (106° C.) for 8 h. When HPLC showed the enamine lactam formation reaction was complete, the reaction mixture was cooled down to 5–10° C. Water (50 mL) and ethyl acetate (50 mL) were then added to the reaction mixture at 5–10° C. with good stirring. The two layers were separated, and the aqueous layer was extracted with EtOAc (50 mL). The combined organic extracts were washed with 5% of citric acid aqueous solution (2×30 mL), water (2×30 mL), and saturated NaCl aqueous solution (50 mL), dried over MgSO$_4$, and concentrated in vacuo. The residue was the purified by flash column chromatography (SiO$_2$, 20–50% EtOAc/hexane gradient elution) to afford desired product (12, 2.71 g, 3.82 g theoretical, 71%) as bright-yellow oil, which solidified upon standing at room temperature under vacuum. For 12, CIMS m/z 383 ($M^++H$, $C_{16}H_{19}IN_2O$).

Example 11

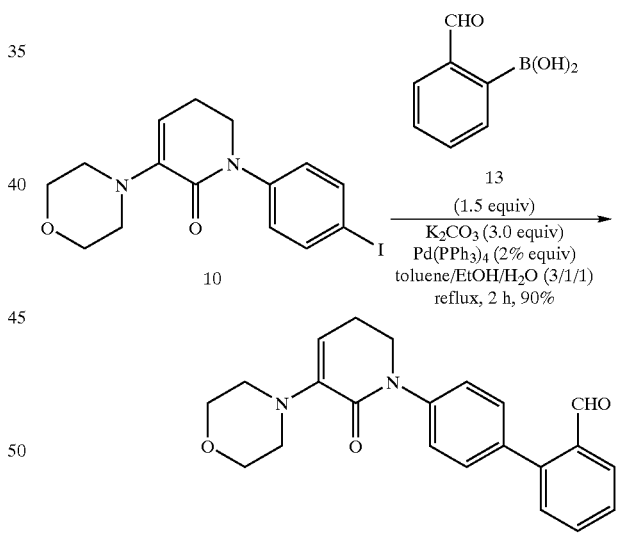

N-[4-(2-Formyl)phenyl]phenyl-3-morpholino-5,6-dihydro-2H-pyridin-2-one (14). A suspension of N-(4-iodo)phenyl-3-morpholino-5,6-dihydro-2H-pyridin-2-one (10, 7.68 g, 20 mmol), 2-formylphenylboronic acid (13, 4.5 g, 30 mmol, 1.5 equiv), and K$_2$CO$_3$ (8.4 g, 60 mmol, 3.0 equiv) in toluene (60 mL) was treated with ethanol (20 mL) and water (20 mL) at room temperature. The resulting mixture was then degassed three times under a steady nitrogen stream before being added Pd(PPh$_3$)$_4$ (460 mg, 0.4 mmol, 2% equiv). The reaction mixture was subsequently degassed three times again before being warmed to reflux for 2 h. When HPLC showed the Suzuki coupling reaction was complete, the reaction mixture was cooled down to 5–10° C. before being treated with water (100 mL) at 5–10° C. with good stirring. The mixture was stirred for an additional 1 h at 5–10° C. before the solids were collected by filtration. The wet cake was then washed with water (2×50 mL) and 10% of tert-butyl methyl ether (TBME)/heptane (2×50 mL) and dried in vacuo to afford desired product (14, 6.52 g, 7.24 g theoretical, 90%) as bright-yellow solids, which was found to be essentially pure by HPLC and was directly employed in the following reaction without further purification. For 14, CIMS m/z 363 (M$^+$+H, $C_{22}H_{22}N_2O_3$).

Example 12

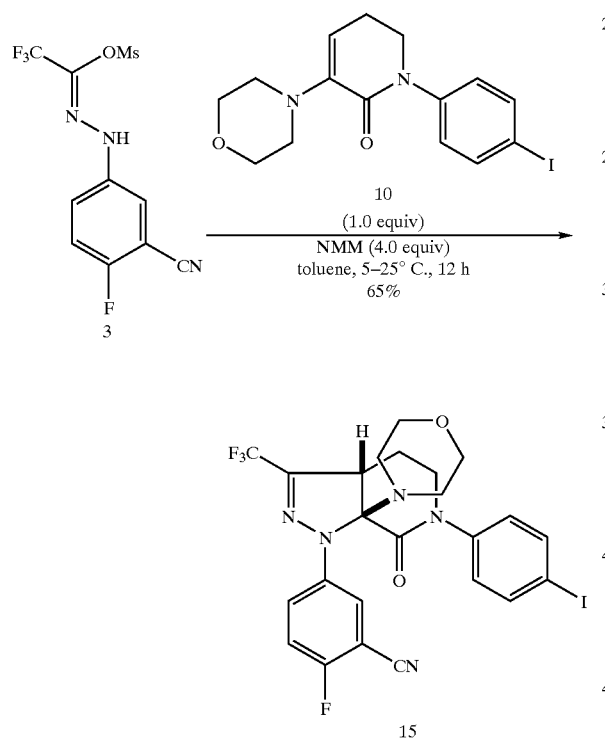

1-(3-Cyano-4-fluoro)phenyl-3-trifluoromethyl-6-(4-iodo)phenyl-8-morpholino-1,4,5,6,8,9-hexahydro-7H-pyrazolo[3,4-c]pyridin-7-one (15). A solution of 2,2,2-trifluoro-N-(3-cyano-4-fluoro)phenylethanehydrazonoyl mesylate (3, 1.30 g, 4.0 mmol) in toluene (18 mL) was treated with N-(4-iodo)phenyl-3-morpholino-5,6-dihydro-2H-pyridin-2-one (10, 1.45 g, 4.0 mmol, 1.0 equiv) at 0–5° C. under $N_2$, and the resulting reaction mixture was treated with N-methylmorpholine (NMM, 1.62 g, 1.76 mL, 16.0 mmol, 4.0 equiv) at 0–5° C. under $N_2$. The reaction mixture was then warmed up to room temperature for 12 h. When HPLC and TLC showed that the reaction was complete, the reaction mixture was treated with water (20 mL) and EtOAc (20 mL). The two layers were separated, and the aqueous layer was extracted with EtOAc (20 mL). The combined organic extracts were washed with water (10 mL) and saturated NaCl aqueous solution (10 mL), dried over $MgSO_4$, and concentrated in vacuo. The residue was directly purified by flash column chromatography ($SiO_2$, 5–20% EtOAc/hexane gradient elution) to afford the desired cycloadduct (15, 1.538 g, 2.366 g theoretical, 65%) as pale-yellow oil, which solidified upon standing at room temperature under vacuum. For 15, CIMS m/z 614 (M$^+$+H, $C_{24}H_{20}F_4IN_5O_2$).

Example 13

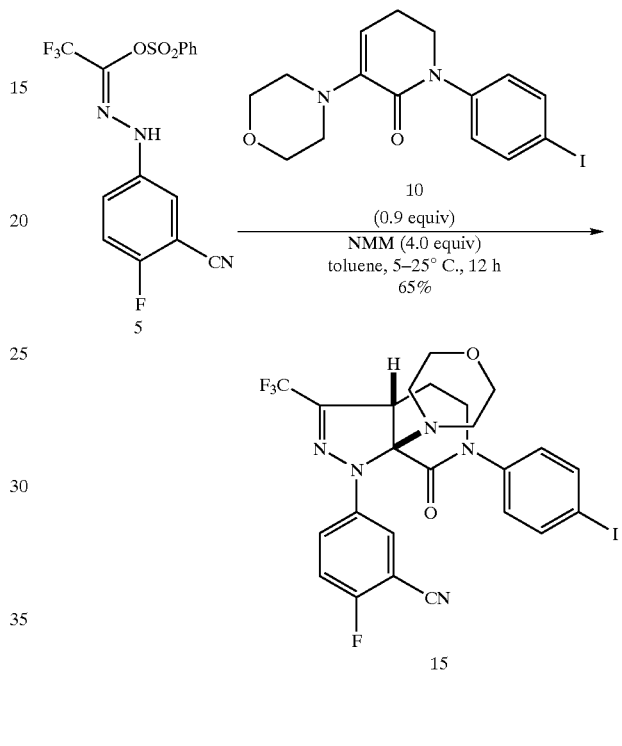

1-(3-Cyano-4-fluoro)phenyl-3-trifluoromethyl-6-(4-iodo)phenyl-8-morpholino-1,4,5,6,8,9-hexahydro-7H-pyrazolo[3,4-c]pyridin-7-one (15). A solution of 2,2,2-trifluoro-N-(3-cyano-4-fluoro)phenylethanehydrazonoyl benzenesulfonate (5, 77.4 mg, 0.2 mmol) in toluene (3 mL) was treated with N-(4-iodo)phenyl-3-morpholino-5,6-dihydro-2H-pyridin-2-one (10, 69.2 mg, 0.18 mmol, 0.9 equiv) at 0–5° C. under $N_2$, and the resulting reaction mixture was treated with N-methylmorpholine (NMM, 81 mg, 88 µL, 0.8 mmol, 4.0 equiv) at 0–5° C. under $N_2$. The reaction mixture was then warmed up to room temperature for 12 h. When HPLC and TLC showed that the reaction was complete, the reaction mixture was treated with water (5 mL) and EtOAc (10 mL). The two layers were separated, and the aqueous layer was extracted with EtOAc (5 mL). The combined organic extracts were washed with water (5 mL) and saturated NaCl aqueous solution (5 mL), dried over $MgSO_4$, and concentrated in vacuo. The residue was directly purified by flash column chromatography ($SiO_2$, 5–20% EtOAc/hexane gradient elution) to afford the desired cycloadduct (15, 72 mg, 110 mg theoretical, 65%), which was identical as the material obtained from Method A in every comparable aspect.

Example 14

Example 15

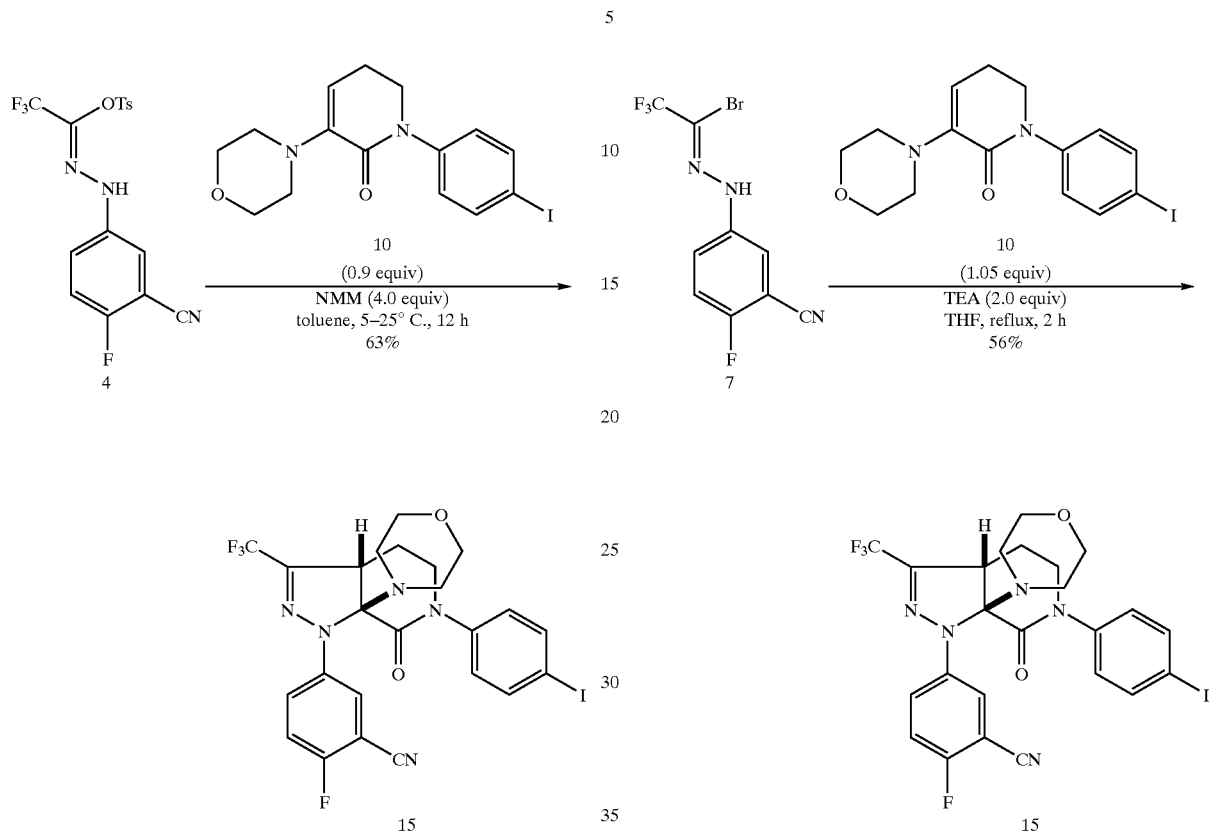

1-(3-Cyano-4-fluoro)phenyl-3-trifluoromethyl-6-(4-iodo) phenyl-8-morpholino-1,4,5,6,8,9-hexahydro-7H-pyrazolo [3,4-c]pyridin-7-one (15). A solution of 2,2,2-trifluoro-N-(3-cyano-4-fluoro)phenylethanehydrazonoyl tosylate (4, 120.3 mg, 0.3 mmol) in toluene (3 mL) was treated with N-(4-iodo)phenyl-3-morpholino-5,6-dihydro-2H-pyridin-2-one (10, 103.7 mg, 0.27 mmol, 0.9 equiv) at 0–5° C. under $N_2$, and the resulting reaction mixture was treated with N-methylmorpholine (NMM, 121 mg, 132 μL, 1.2 mmol, 4.0 equiv) at 0–5° C. under $N_2$. The reaction mixture was then warmed up to room temperature for 12 h. When HPLC and TLC showed that the reaction was complete, the reaction mixture was treated with water (5 mL) and EtOAc (10 mL). The two layers were separated, and the aqueous layer was extracted with EtOAc (5 mL). The combined organic extracts were washed with water (5 mL) and saturated NaCl aqueous solution (5 mL), dried over $MgSO_4$, and concentrated in vacuo. The residue was directly purified by flash column chromatography ($SiO_2$, 5–20% EtOAc/hexane gradient elution) to afford the desired cycloadduct (15, 104 mg, 166 mg theoretical, 63%), which was identical as the material obtained from Method A in every comparable aspect.

1-(3-Cyano-4-fluoro)phenyl-3-trifluoromethyl-6-(4-iodo) phenyl-8-morpholino-1,4,5,6,8,9-hexahydro-7H-pyrazolo [3,4-c]pyridin-7-one (15). A solution of 2,2,2-trifluoro-N-(3-cyano-4-fluoro)phenylethanehydrazonoyl bromide (7, 310 mg, 1.0 mmol) in anhydrous THF (5 mL) was treated with N-(4-iodo)phenyl-3-morpholino-5,6-dihydro-2H-pyridin-2-one (10, 403 mg, 1.05 mmol, 1.05 equiv) at 0–5° C. under $N_2$, and the resulting reaction mixture was treated with triethylamine (TEA, 202 mg, 278 μL, 2.0 mmol, 2.0 equiv) at 0–5° C. under $N_2$. The reaction mixture was then warmed up to reflux for 2 h. When HPLC and TLC showed that the reaction was complete, the reaction mixture was treated with water (10 mL) and EtOAc (20 mL). The two layers were separated, and the aqueous layer was extracted with EtOAc (10 mL). The combined organic extracts were washed with water (10 mL) and saturated NaCl aqueous solution (10 mL), dried over $MgSO_4$, and concentrated in vacuo. The residue was directly purified by flash column chromatography ($SiO_2$, 5–20% EtOAc/hexane gradient elution) to afford the desired cycloadduct (15, 343 mg, 613 mg theoretical, 56%), which was identical as the material obtained from Method A in every comparable aspect.

Example 16

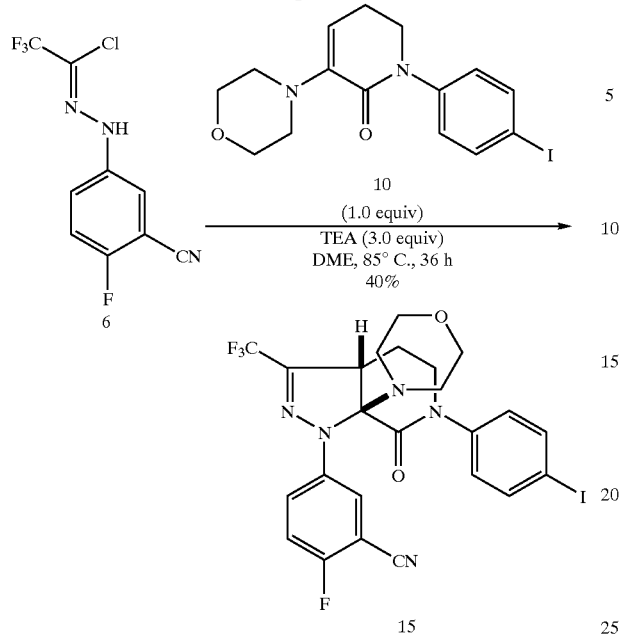

1-(3-Cyano-4-fluoro)phenyl-3-trifluoromethyl-6-(4-iodo)phenyl-8-morpholino-1,4,5,6,8,9-hexahydro-7H-pyrazolo[3,4-c]pyridin-7-one (15). A solution of 2,2,2-trifluoro-N-(3-cyano-4-fluoro)phenylethanehydrazonoyl chloride (6, 266 mg, 1.0 mmol) in anhydrous ethylene glycol dimethyl ether (DME, 5 mL) was treated with N-(4-iodo)phenyl-3-morpholino-5,6-dihydro-2H-pyridin-2-one (10, 384 mg, 1.0 mmol, 1.0 equiv) at 0–5° C. under $N_2$, and the resulting reaction mixture was treated with triethylamine (TEA, 303 mg, 417 µL, 3.0 mmol, 3.0 equiv) at 0–5° C. under $N_2$. The reaction mixture was then warmed up to reflux (85° C.) for 36 h. When HPLC and TLC showed that the reaction was complete, the reaction mixture was treated with water (10 mL) and EtOAc (20 mL). The two layers were separated, and the aqueous layer was extracted with EtOAc (10 mL). The combined organic extracts were washed with water (10 mL) and saturated NaCl aqueous solution (10 mL), dried over $MgSO_4$, and concentrated in vacuo. The residue was directly purified by flash column chromatography ($SiO_2$, 5–20% EtOAc/hexane gradient elution) to afford the desired cycloadduct (15, 245 mg, 613 mg theoretical, 40%), which was identical as the material obtained from Method A in every comparable aspect.

Example 17

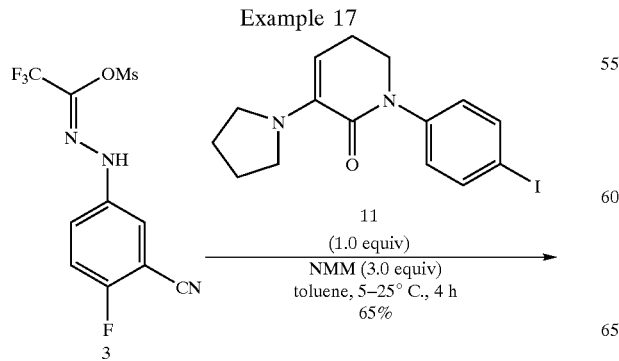

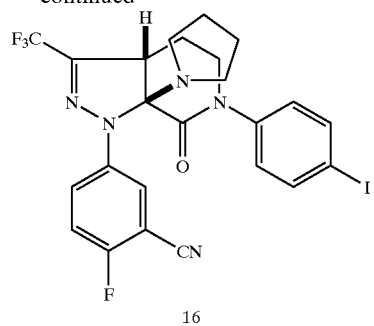

1-(3-Cyano-4-fluoro)phenyl-3-trifluoromethyl-6-(4-iodo)phenyl-8-pyrrolidino-1,4,5,6,8,9-hexahydro-7H-pyrazolo[3,4-c]pyridin-7-one (16). A solution of 2,2,2-trifluoro-N-(3-cyano-4-fluoro)phenylethanehydrazonoyl mesylate (3, 65 mg, 0.2 mmol) in toluene (2 mL) was treated with N-(4-iodo)phenyl-3-pyrrolidino-5,6-dihydro-2H-pyridin-2-one (11, 74 mg, 0.2 mmol, 1.0 equiv) at 0–5° C. under $N_2$, and the resulting reaction mixture was treated with N-methylmorpholine (NMM, 61 mg, 66 µL, 0.6 mmol, 3.0 equiv) at 0–5° C. under $N_2$. The reaction mixture was then warmed up to room temperature for 4 h. When HPLC and TLC showed that the reaction was complete, the reaction mixture was treated with water (5 mL) and EtOAc (10 mL). The two layers were separated, and the aqueous layer was extracted with EtOAc (5 mL). The combined organic extracts were washed with water (5 mL) and saturated NaCl aqueous solution (5 mL), dried over $MgSO_4$, and concentrated in vacuo. The residue was directly purified by flash column chromatography ($SiO_2$, 5–20% EtOAc/hexane gradient elution) to afford the desired cycloadduct (16, 78 mg, 119 mg theoretical, 65%) as a pale-yellow oil, which solidified upon standing at room temperature under vacuum. For 16, CIMS m/z 598 ($M^+$+H, $C_{24}H_{20}F_4IN_5O$).

Example 18

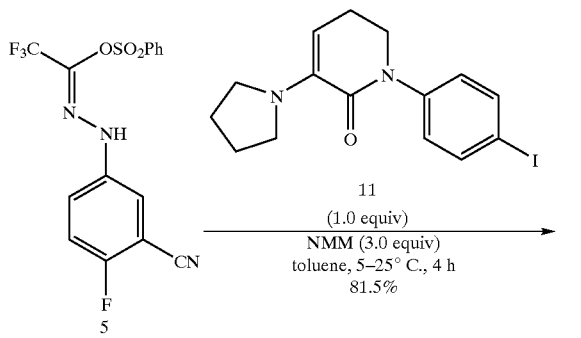

1-(3-Cyano-4-fluoro)phenyl-3-trifluoromethyl-6-(4-iodo)phenyl-8-pyrrolidino-1,4,5,6,8,9-hexahydro-7H-pyrazolo[3,4-c]pyridin-7-one (16). A solution of 2,2,2-trifluoro-N-(3-cyano-4-fluoro)phenylethanehydrazonoyl benzenesulfonate (5, 77.4 mg, 0.2 mmol) in toluene (3 mL) was treated with N-(4-iodo)phenyl-3-pyrrolidino-5,6-dihydro-2H-pyridin-2-one (11, 74 mg, 0.2 mmol, 1.0 equiv) at 0–5° C. under N₂, and the resulting reaction mixture was treated with N-methylmorpholine (NMM, 61 mg, 66 μL, 0.6 mmol, 3.0 equiv) at 0–5° C. under N₂. The reaction mixture was then warmed up to room temperature for 4 h. When HPLC and TLC showed that the reaction was complete, the reaction mixture was treated with water (5 mL) and EtOAc (10 mL). The two layers were separated, and the aqueous layer was extracted with EtOAc (5 mL). The combined organic extracts were washed with water (5 mL) and saturated NaCl aqueous solution (5 mL), dried over MgSO₄, and concentrated in vacuo. The residue was directly purified by flash column chromatography (SiO₂, 5–20% EtOAc/hexane gradient elution) to afford the desired cycloadduct (16, 97 mg, 119 mg theoretical, 81.5%), which was identical as the material obtained from Method A in every comparable aspect.

extracts were washed with water (5 mL) and saturated NaCl aqueous solution (5 mL), dried over MgSO₄, and concentrated in vacuo. The residue was directly purified by flash column chromatography (SiO₂, 5–20% EtOAc/hexane gradient elution) to afford the desired cycloadduct (16, 98 mg, 119 mg theoretical, 82%), which was identical as the material obtained from Method A in every comparable aspect.

Example 19

Example 20

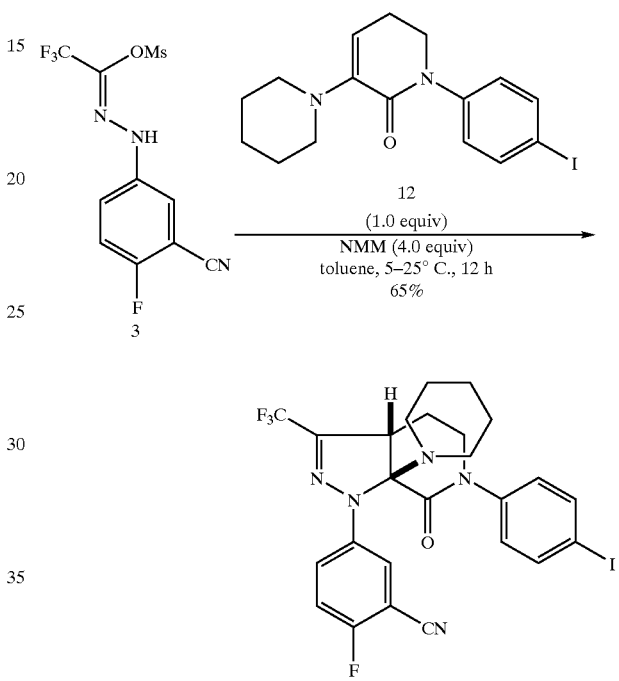

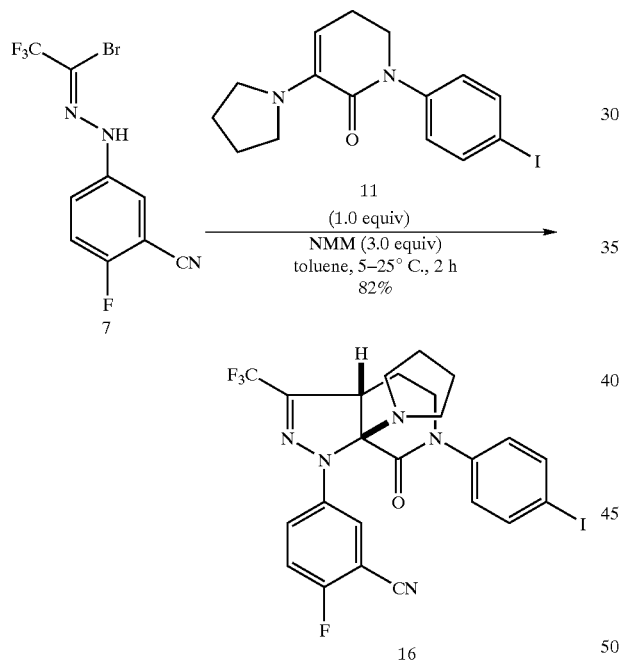

1-(3-Cyano-4-fluoro)phenyl-3-trifluoromethyl-6-(4-iodo)phenyl-8-pyrrolidino-1,4,5,6,8,9-hexahydro-7H-pyrazolo[3,4-c]pyridin-7-one (16). A solution of 2,2,2-trifluoro-N-(3-cyano-4-fluoro)phenylethanehydrazonoyl bromide (7, 62 mg, 0.2 mmol) in toluene (3 mL) was treated with N-(4-iodo)phenyl-3-pyrrolidino-5,6-dihydro-2H-pyridin-2-one (11, 74 mg, 0.2 mmol, 1.0 equiv) at 0–5° C. under N₂, and the resulting reaction mixture was treated with N-methylmorpholine (NMM, 61 mg, 66 μL, 0.6 mmol, 3.0 equiv) at 0–5° C. under N₂. The reaction mixture was then warmed up to room temperature for 2 h. When HPLC and TLC showed that the reaction was complete, the reaction mixture was treated with water (5 mL) and EtOAc (10 mL). The two layers were separated, and the aqueous layer was extracted with EtOAc (5 mL). The combined organic 1-(3-Cyano-4-fluoro)phenyl-3-trifluoromethyl-6-(4-iodo)phenyl-8-piperidino-1,4,5,6,8,9-hexahydro-7H-pyrazolo[3,4-c]pyridin-7-one (17). A solution of 2,2,2-trifluoro-N-(3-cyano-4-fluoro)phenylethanehydrazonoyl mesylate (3, 174 mg, 0.54 mmol) in toluene (5 mL) was treated with N-(4-iodo)phenyl-3-piperidino-5,6-dihydro-2H-pyridin-2-one (12, 206 mg, 0.54 mmol, 1.0 equiv) at 0–5° C. under N₂, and the resulting reaction mixture was treated with N-methylmorpholine (NMM, 222 mg, 242 μL, 2.2 mmol, 4.0 equiv) at 0–5° C. under N₂. The reaction mixture was then warmed up to room temperature for 12 h. When HPLC and TLC showed that the reaction was complete, the reaction mixture was treated with water (10 mL) and EtOAc (20 mL). The two layers were separated, and the aqueous layer was extracted with EtOAc (10 mL). The combined organic extracts were washed with water (10 mL) and saturated NaCl aqueous solution (10 mL), dried over MgSO₄, and concentrated in vacuo. The residue was directly purified by flash column chromatography (SiO₂, 5–20% EtOAc/hexane gradient elution) to afford the desired cycloadduct (17, 215 mg, 330 mg theoretical, 65%) as a pale-yellow oil, which solidified upon standing at room temperature under vacuum. For 17, CIMS m/z 612 (M++H, $C_{25}H_{22}F_4IN_5O$).

Example 21

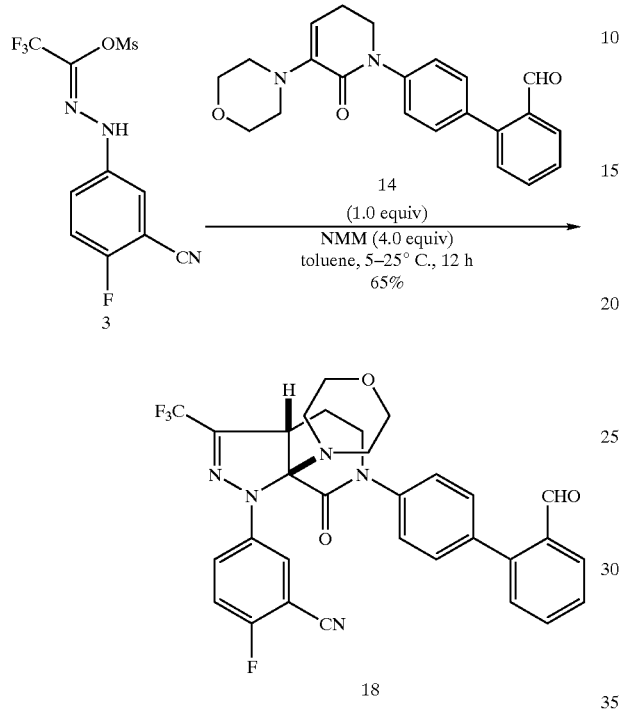

1-(3-Cyano-4-fluoro)phenyl-3-trifluoromethyl-6-[4-(2-formyl)phenyl]phenyl-8-morpholino-1,4,5,6,8,9-hexahydro-7H-pyrazolo[3,4-c]pyridin-7-one (18). A solution of 2,2,2-trifluoro-N-(3-cyano-4-fluoro) phenylethanehydrazonoyl mesylate (3, 1.30 g, 4.0 mmol) in toluene (15 mL) was treated with N-[4-(2-formyl)phenyl] phenyl-3-morpholino-5,6-dihydro-2H-pyridin-2-one (14, 1.45 g, 4.0 mmol, 1.0 equiv) at 0–5° C. under $N_2$, and the resulting reaction mixture was treated with N-methylmorpholine (NMM, 1.62 g, 1.76 mL, 16.0 mmol, 4.0 equiv) at 0–5° C. under $N_2$. The reaction mixture was then warmed up to room temperature for 12 h. When HPLC and TLC showed that the reaction was complete, the reaction mixture was treated with water (20 mL) and EtOAc (40 mL). The two layers were separated, and the aqueous layer was extracted with EtOAc (20 mL). The combined organic extracts were washed with water (20 mL) and saturated NaCl aqueous solution (20 mL), dried over $MgSO_4$, and concentrated in vacuo. The residue was directly purified by flash column chromatography ($SiO_2$, 5–20% EtOAc/hexane gradient elution) to afford the desired cycloadduct (18, 1.54 g, 2.364 g theoretical, 65%) as a pale-yellow oil, which solidified upon standing at room temperature under vacuum. For 18, CIMS m/z 592 (M++H, $C_{31}H_{25}F_4N_5O_3$).

Example 22

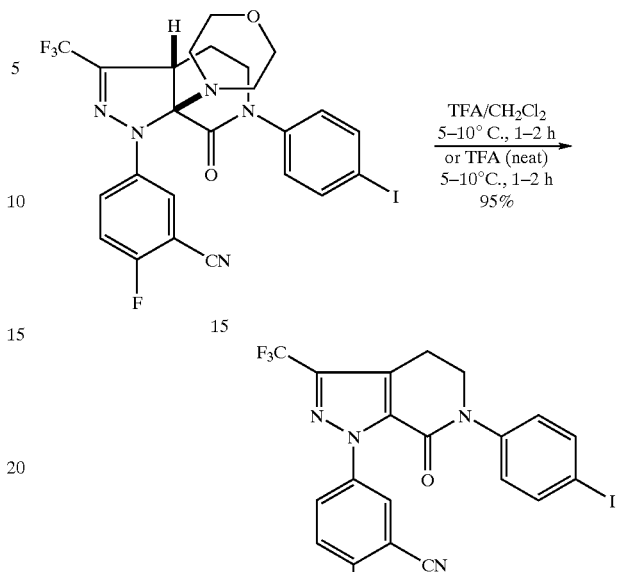

1-(3-Cyano-4-fluoro)phenyl-3-trifluoromethyl-6-(4-iodo) phenyl-1,4,5,6-tetrahydro-7H-pyrazolo[3,4-c]pyridin-7-one (19). A solution of 1-(3-cyano-4-fluoro)phenyl-3-trifluoromethyl-6-(4-iodo)phenyl-8-morpholino-1,4,5,6,8,9-hexahydro-7H-pyrazolo[3,4-c]pyridin-7-one (15, 613 mg, 1.0 mmol) in methylenechloride ($CH_2Cl_2$, 2 mL) was treated with trifluoroacetic acid (TFA, 2.0 mL) at 5–10° C., and the resulting reaction mixture was stirred at 5–10° C. for an additional 1–2 h. When HPLC and TLC showed the reaction was complete, the solvents were removed in vacuo, and the residue was directly purified by flash column chromatography ($SiO_2$, 5–20% EtOAc/hexane gradient elution) to afford the desired elimination product (19, 500 mg, 526 mg theoretical, 95%) as a pale-yellow oil, which solidified upon standing at room temperature under vacuum. For 19, CIMS m/z 527 (M++H, $C_{20}H_{11}F_4IN_4O$).

Example 23

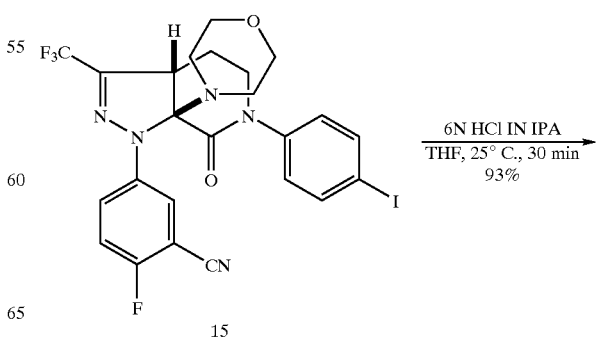

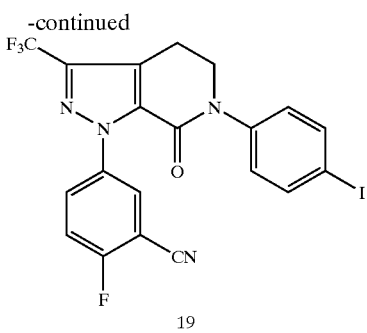

19

1-(3-Cyano-4-fluoro)phenyl-3-trifluoromethyl-6-(4-iodo) phenyl-1,4,5,6-tetrahydro-7H-pyrazolo[3,4-c]pyridin-7-one (19). A solution of 1-(3-cyano-4-fluoro)phenyl-3-trifluoromethyl-6-(4-iodo)phenyl-8-morpholino-1,4,5,6,8,9-hexahydro-7H-pyrazolo[3,4-c]pyridin-7-one (15, 613 mg, 1.0 mmol) in THF (4 mL) was treated with a solution of 5–6 N hydrogen chloride in isopropyl alcohol (IPA, 4 mL) at 5–10° C., and the resulting reaction mixture was stirred at 5–10° C. for 30 min. When HPLC and TLC showed the reaction was complete, the solvent was removed in vacuo, and the residue was directly purified by flash column chromatography (SiO$_2$, 5–20% EtOAc/hexane gradient elution) to afford the desired elimination product (19, 490 mg, 526 mg theoretical, 9.3%), which was identical as the material obtained from Method A in every comparable aspect.

Example 24

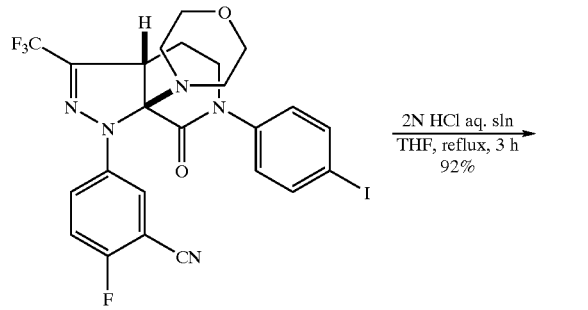

1-(3-Cyano-4-fluoro)phenyl-3-trifluoromethyl-6-(4-iodo) phenyl-1,4,5,6-tetrahydro-7H-pyrazolo[3,4-c]pyridin-7-one (19). A solution of 1-(3-cyano-4-fluoro)phenyl-3-trifluoromethyl-6-(4-iodo)phenyl-8-morpholino-1,4,5,6,8,9-hexahydro-7H-pyrazolo[3,4-c]pyridin-7-one (15, 613 mg, 1.0 mmol) in THF (4 mL) was treated with a 2 N HCl aqueous solution (4 mL) at 25° C. The resulting reaction mixture was subsequently warmed to reflux for 3 h. When HPLC and TLC showed the reaction was complete, the reaction mixture was treated with water (10 mL) and EtOAc (20 mL). The two layers were separated, and the aqueous layer was extracted with EtOAc (10 mL). The combined organic extracts were washed with water (10 mL) and saturated NaCl aqueous solution (10 mL), dried over MgSO$_4$, and concentrated in vacuo. The residue was directly purified by flash column chromatography (SiO$_2$, 5–20% EtOAc/hexane gradient elution) to afford the desired elimination product (19, 484 mg, 526 mg theoretical, 92%), which was identical as the material obtained from Method A in every comparable aspect.

Example 25

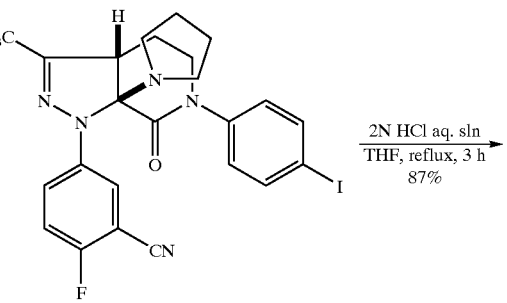

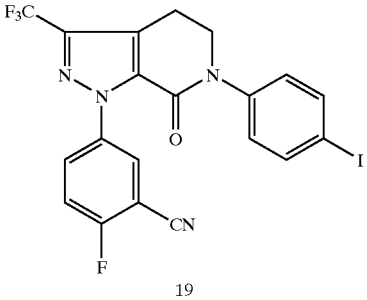

19

1-(3-Cyano-4-fluoro)phenyl-3-trifluoromethyl-6-(4-iodo) phenyl-1,4,5,6-tetrahydro-7H-pyrazolo[3,4-c]pyridin-7-one (19). A solution of 1-(3-cyano-4-fluoro)phenyl-3-trifluoromethyl-6-(4-iodo)phenyl-8-pyrrolidino-1,4,5,6,8,9-hexahydro-7H-pyrazolo[3,4-c]pyridin-7-one (16, 60 mg, 0.1 mmol) in THF (1 mL) was treated with a 2 N HCl aqueous solution (1 mL) at 25° C. The resulting reaction mixture was subsequently warmed to reflux for 3 h. When HPLC and TLC showed the reaction was complete, the reaction mixture was treated with water (2 mL) and EtOAc (5 mL). The two layers were separated, and the aqueous layer was extracted with EtOAc (5 mL). The combined organic extracts were washed with water (3 mL) and saturated NaCl aqueous solution (3 mL), dried over MgSO$_4$, and concentrated in vacuo. The residue was directly purified by flash column chromatography (SiO$_2$, 5–20% EtOAc/hexane gradient elution) to afford the desired elimination product (19, 46 mg, 53 mg theoretical, 87%), which was identical as the material obtained from Method A in every comparable aspect.

Example 26

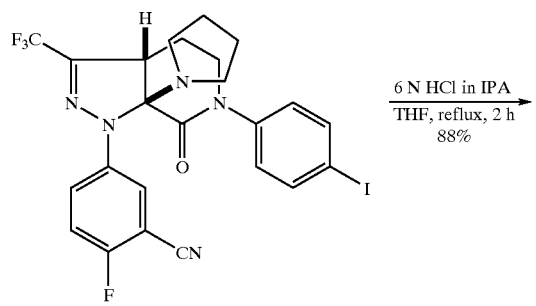

1-(3-Cyano-4-fluoro)phenyl-3-trifluoromethyl-6-(4-iodo)phenyl-1,4,5,6-tetrahydro-7H-pyrazolo[3,4-c]pyridin-7-one (19). A solution of 1-(3-cyano-4-fluoro)phenyl-3-trifluoromethyl-6-(4-iodo)phenyl-8-pyrrolidino-1,4,5,6,8,9-hexahydro-7H-pyrazolo[3,4-c]pyridin-7-one (16, 60 mg, 0.1 mmol) in THF (1 mL) was treated with a solution of 5–6 N hydrogen chloride in isopropyl alcohol (IPA, 1 mL) at 5–10° C., and the resulting reaction mixture was warmed to reflux for 2 h. When HPLC and TLC showed the reaction was complete, the solvent was removed in vacuo, and the residue was directly purified by flash column chromatography (SiO$_2$, 5–20% EtOAc/hexane gradient elution) to afford the desired elimination product (19, 47 mg, 53 mg theoretical, 88%), which was identical as the material obtained from Method A in every comparable aspect.

Example 27

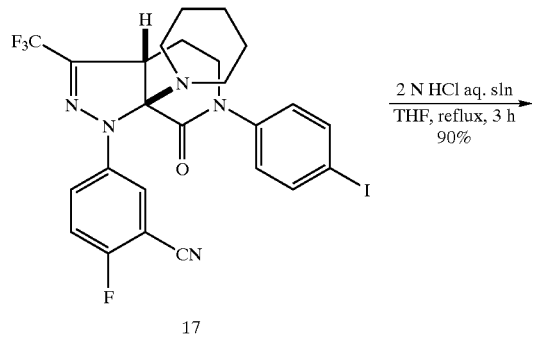

1-(3-Cyano-4-fluoro)phenyl-3-trifluoromethyl-6-(4-iodo)phenyl-1,4,5,6-tetrahydro-7H-pyrazolo[3,4-c]pyridin-7-one (19). A solution of 1-(3-cyano-4-fluoro)phenyl-3-trifluoromethyl-6-(4-iodo)phenyl-8-piperidino-1,4,5,6,8,9-hexahydro-7H-pyrazolo[3,4-c]pyridin-7-one (17, 611 mg, 1.0 mmol) in THF (4 mL) was treated with a 2 N HCl aqueous solution (4 mL) at 25° C. The resulting reaction mixture was subsequently warmed to reflux for 3 h. When HPLC and TLC showed the reaction was complete, the reaction mixture was treated with water (10 mL) and EtOAc (20 mL). The two layers were separated, and the aqueous layer was extracted with EtOAc (10 mL). The combined organic extracts were washed with water (10 mL) and saturated NaCl aqueous solution (10 mL), dried over MgSO$_4$, and concentrated in vacuo. The residue was directly purified by flash column chromatography (SiO$_2$, 5–20% EtOAc/hexane gradient elution) to afford the desired elimination product (19, 473 mg, 526 mg theoretical, 90%), which was identical as the material obtained from Method A in every comparable aspect.

Example 28

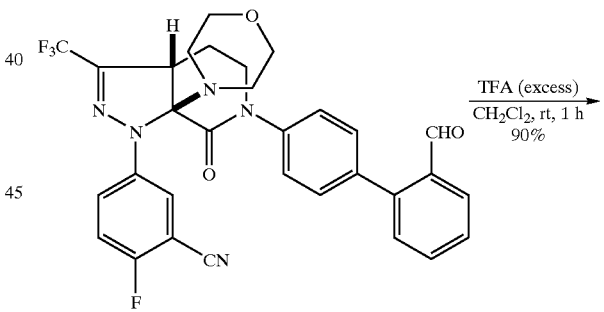

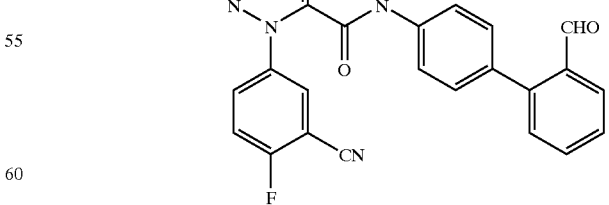

1-(3-Cyano-4-fluoro)phenyl-3-trifluoromethyl-6-[4-(2-formyl)phenyl]phenyl-1,4,5,6-tetrahydro-7H-pyrazolo[3,4-c]pyridin-7-one (20). A solution of 1-(3-Cyano-4-fluoro)

phenyl-3-trifluoromethyl-6-[4-(2-formyl)phenyl]phenyl-8-morpholino-1,4,5,6,8,9-hexahydro-7H-pyrazolo[3,4-c]pyridin-7-one (18, 592 mg, 1.0 mmol) in methylenechloride (CH$_2$Cl$_2$, 3 mL) was treated with trifluoroacetic acid (TFA, 3.0 mL) at 5–10° C., and the resulting reaction mixture was stirred at 5–10° C. for an additional 2 h. When HPLC and TLC showed the reaction was complete, the solvents were removed in vacuo, and the residue was directly purified by flash column chromatography (SiO$_2$, 5–20% EtOAc/hexane gradient elution) to afford the desired elimination product (20, 454 mg, 504 mg theoretical, 90%) as a pale-yellow oil, which solidified upon standing at room temperature under vacuum. For 20, CIMS m/z 505 (M$^+$+H, C$_{27}$H$_{16}$F$_4$N$_4$O$_2$).

Example 29

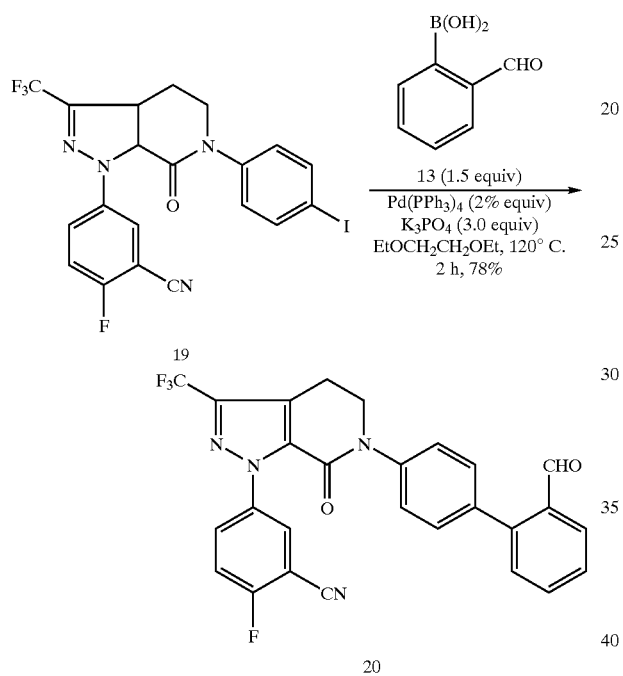

1-(3-Cyano-4-fluoro)phenyl-3-trifluoromethyl-6-[4-(2-formyl)phenyl]phenyl-1,4,5,6-tetrahydro-7H-pyrazolo[3,4-c]pyridin-7-one (20). A suspension 1-(3-cyano-4-fluoro)phenyl-3-trifluoromethyl-6-(4-iodo)phenyl-1,4,5,6-tetrahydro-7H-pyrazolo[3,4-c]pyridin-7-one (19, 10.54 g, 20 mmol), 2-formylphenylboronic acid (13, 4.5 g, 30 mmol, 1.5 equiv), and K$_3$PO$_4$ (12.74 g, 60 mmol, 3.0 equiv) in ethylene glycol diethyl ether (DME, 100 mL) was degassed three times under a steady nitrogen stream before being treated with Pd(PPh$_3$)$_4$ (460 mg, 0.4 mmol, 2% equiv). The reaction mixture was subsequently degassed three times again before being warmed to reflux (120° C.) for 2 h. When HPLC showed the Suzuki coupling reaction was complete, the reaction mixture was cooled down to 5–10° C. before being treated with water (100 mL) and ethyl acetate (200 mL) at 5–10° C. with good stirring. The mixture was stirred for an additional 1 h at 5–10° C. before the two layers were separated. The aqueous layer was extracted with ethyl acetate (2×50 mL), and the combined organic extracts were washed with water (2×50 mL), saturated NaCl aqueous solution (2×50 mL), dried over MgSO$_4$, and concentrated in vacuo. The residue was purified by flash column chromatography (SiO$_2$, 10–30% ethyl acetate/hexane gradient elution) to afford desired product (20, 7.86 g, 10.08 g theoretical, 78%), which was identical as the material obtained from Method A in every comparable aspect.

Example 30

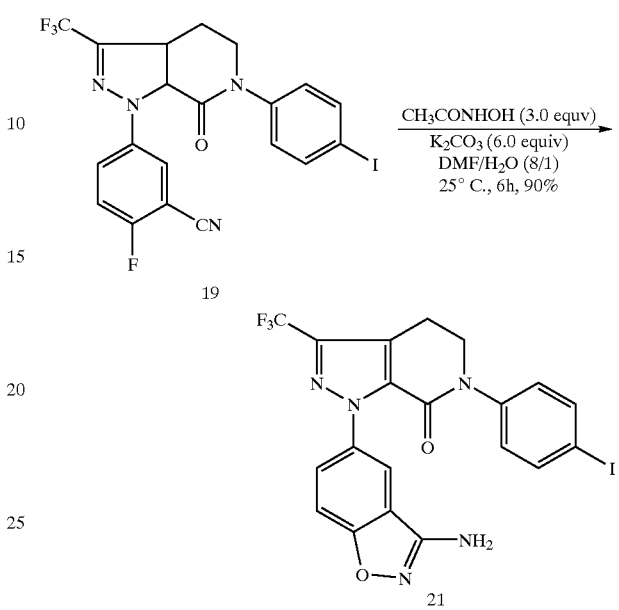

1-(3-Amino-1,2-benz[d]isoxazol-5-yl]-3-trifluoromethyl-6-(4-iodo)phenyl-1,4,5,6-tetrahydro-7H-pyrazolo[3,4-c]pyridin-7-one (21). A suspension of 1-(3-cyano-4-fluoro)phenyl-3-trifluoromethyl-6-(4-iodo)phenyl-1,4,5,6-tetrahydro-7H-pyrazolo[3,4-c]pyridin-7-one (19, 4.22 g, 8.0 mmol) in N,N-dimethylformamide (DMF, 35 mL) was treated with K$_2$CO$_3$ (6.63 g, 48 mmol, 6.0 equiv) and water (5 mL) at room temperature, and the resulting mixture was treated with acetohydroxamic acid (1.8 g, 24 mmol, 3.0 equiv) at room temperature. The reaction mixture was subsequently stirred at room temperature for 4 h. When TLC and HPLC showed the reaction was complete, the reaction mixture was treated with water (100 mL) with good stirring at room temperature. The solids were collected by filtration, washed with water (2×50 mL), 10% tert-butyl methyl ether/heptane (2×25 mL), and dried in vacuo to afford the desired product (21, 3.88 g, 4.31 g theoretical, 90%), which was found to be pure enough by HPLC to do the following reaction without further purification. For 21, CIMS m/z 540 (M$^+$+H, C$_{20}$H$_{13}$F$_3$IN$_5$O$_2$).

Example 31

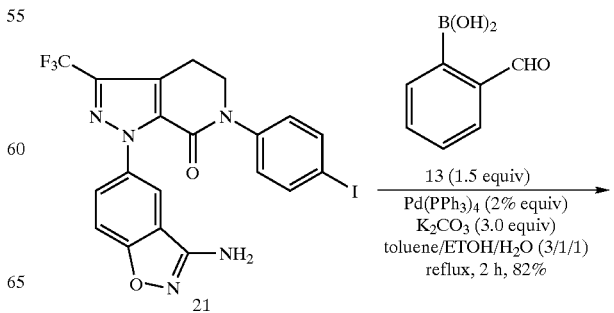

-continued

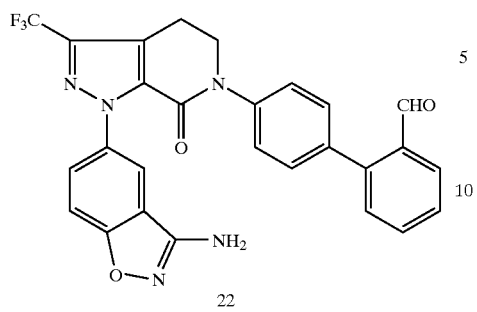

22

-continued

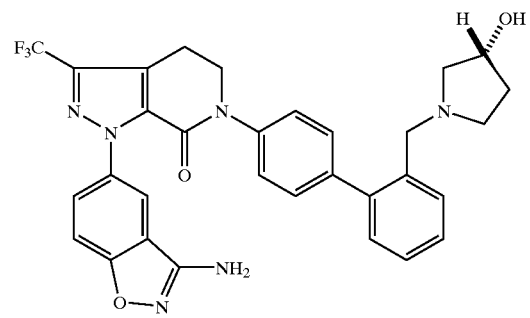

24

1-(3-Amino-1,2-benz[d]isoxazol-5-yl]-3-trifluoromethyl-6-[4-(2-formyl)phenyl]phenyl-1,4,5,6-tetrahydro-7H-pyrazolo[3,4-c]pyridin-7-one (22). A suspension of 1-(3-amino-1,2-benz[d]isoxazol-5-yl]-3-trifluoromethyl-6-(4-iodo)phenyl-1,4,5,6-tetrahydro-7H-pyrazolo[3,4-c]pyridin-7-one (21, 4.31 g, 8.0 mmol), 2-formylphenylboronic acid (13, 1.8 g, 12 mmol, 1.5 equiv), and $K_2CO_3$ (3.31 g, 24 mmol, 3.0 equiv) in toluene (30 mL) was treated with ethanol (10 mL) and water (10 mL) at room temperature. The resulting mixture was then degassed three times under a steady nitrogen stream before being added $Pd(PPh_3)_4$ (185 mg, 0.16 mmol, 2% equiv). The reaction mixture was subsequently degassed three times again before being warmed to reflux for 2 h. When HPLC showed the Suzuki coupling reaction was complete, the reaction mixture was cooled down to 5–10° C. before being treated with water (100 mL) at 5–10° C. with good stirring. The mixture was stirred for an additional 1 h at 5–10° C. before the solids were collected by filtration. The wet cake was then washed with water (2×50 mL) and 10% of tert-butyl methyl ether (TBME)/heptane (2×50 mL) and dried in vacuo to afford desired product (22, 3.39 g, 4.14 g theoretical, 82%) as bright-yellow solids, which was found to be essentially pure by HPLC and was directly employed in the following reaction without further purification. For 22, CIMS m/z 518 ($M^++H$, $C_{27}H_{18}F_3N_5O_3$).

1-(3-Amino-1,2-benz[d]isoxazol-5-yl]-3-trifluoromethyl-6-[4-[2-[(3R)-3-hydroxy-1-pyrrolidinyl]methyl]phenyl]phenyl-1,4,5,6-tetrahydro-7H-pyrazolo[3,4-c]pyridin-7-one (24). A suspension of 1-(3-amino-1,2-benz[d]isoxazol-5-yl]-3-trifluoromethyl-6-[4-(2-formyl)phenyl]phenyl-1,4,5,6-tetrahydro-7H-pyrazolo[3,4-c]pyridin-7-one (22, 11.3 g, 21.9 mmol) in DMSO (80 mL) was treated with (3R)-3-hydroxypyrrolidine hydrochloride salt (23, 3.2 g, 26.3 mmol, 1.2 equiv) at 25° C., and the resulting reaction mixture was subsequently stirred at room temperature for 1–2 h. A solution of $NaB(OAc)_3H$ (5.6 g, 26.3 mmol, 1.2 equiv) in DMSO (40 mL) was then added dropwise into the reaction mixture at room temperature. The resulting reaction mixture was then stirred at room temperature for 3 h. When HPLC and TLC showed the reduction reaction was complete, the reaction mixture was quenched with a 10% of $K_2CO_3$ aqueous solution (150 mL) at room temperature, and the resulting mixture was stirred for an additional 1 h. The resulting precipitates were collected by filtration, washed with water (2×40 mL), and dried in vacuo to afford the crude, desired reductive amination product (24, 11.35 g, 12.9 g theoretical, 88% yield) as off-white powders. This crude product was subsequently recrystallized in acetonitrile/water (4:1) to afford the pure desired product (24, 8.65 g, 12.9 g theoretical, 67%) as white powders. For 24, CIMS m/z 589 ($M^++H$, $C_{31}H_{27}F_3N_6O_3$).

Example 32

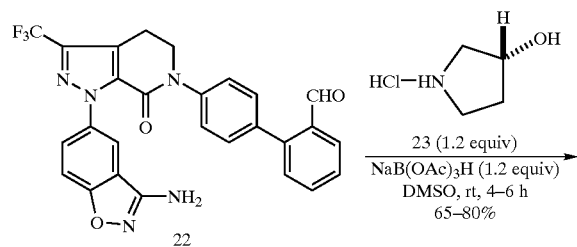

Example 33

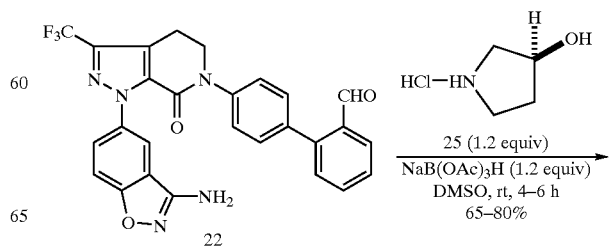

-continued

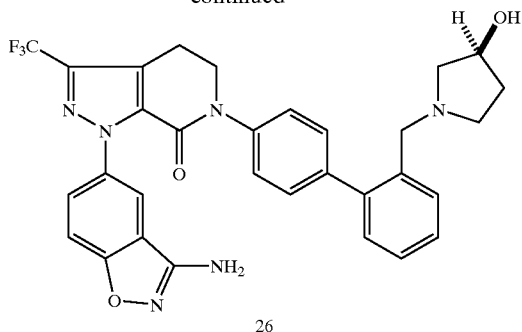

26

1-(3-Amino-1,2-benz[d]isoxazol-5-yl]-3-trifluoromethyl-6-[4-[2-[(3S)-3-hydroxy-1-pyrrolidinyl]methyl]phenyl] phenyl-1,4,5,6-tetrahydro-7H-pyrazolo[3,4-c]pyridin-7-one (26). A suspension of 1-(3-amino-1,2-benz[d]isoxazol-5-yl]-3-trifluoromethyl-6-[4-(2-formyl)phenyl]phenyl-1,4,5,6-tetrahydro-7H-pyrazolo[3,4-c]pyridin-7-one (22, 2.07 g, 4.0 mmol) in DMSO (20 mL) was treated with (3S)-3-hydroxypyrrolidine hydrochloride salt (25, 594 mg, 4.8 mmol, 1.2 equiv) at 25° C., and the resulting reaction mixture was subsequently stirred at room temperature for 1–2 h. A solution of NaB(OAc)$_3$H (1.02 g, 4.8 mmol, 1.2 equiv) in DMSO (8 mL) was then added dropwise into the reaction mixture at room temperature. The resulting reaction mixture was then stirred at room temperature for 3 h. When HPLC and TLC showed the reduction reaction was complete, the reaction mixture was quenched with a 10% of K$_2$CO$_3$ aqueous solution (30 mL) at room temperature, and the resulting mixture was stirred for an additional 1 h. The resulting precipitates were collected by filtration, washed with water (2×10 mL), and dried in vacuo to afford the crude, desired reductive amination product (26, 1.98 g, 2.35 g theoretical, 84% yield) as off-white powders. This crude product was subsequently recrystallized in acetonitrile/water (4:1) to afford the pure desired product (26, 1.55 g, 2.35 g theoretical, 66%) as white powders. For 26, CIMS m/z 589 (M$^+$+H, C$_{31}$H$_{27}$F$_3$N$_6$O$_3$).

Example 34

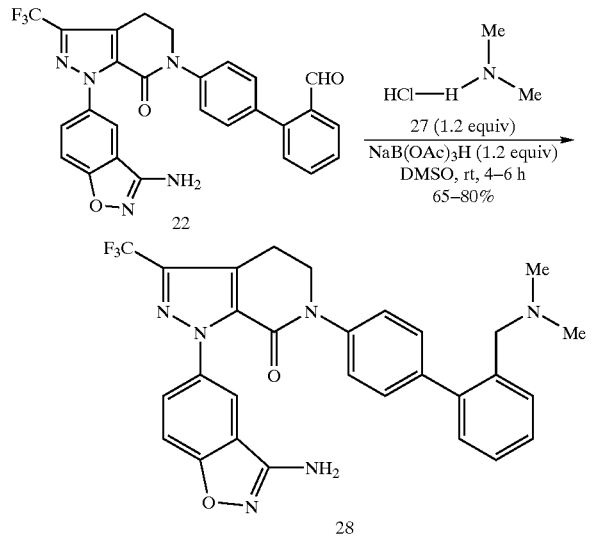

1-(3-Amino-1,2-benz[d]isoxazol-5-yl]-3-trifluoromethyl-6-[4-[2-(N,N-dimethylamino)methyl]phenyl]phenyl-1,4,5,6-tetrahydro-7H-pyrazolo[3,4-c]pyridin-7-one (28). A suspension of 1-(3-amino-1,2-benz[d]isoxazol-5-yl]-3-trifluoromethyl-6-[4-(2-formyl)phenyl]phenyl-1,4,5,6-tetrahydro-7H-pyrazolo[3,4-c]pyridin-7-one (22, 2.07 g, 4.0 mmol) in DMSO (20 mL) was treated dimethylamine hydrochloride salt (27, 392 mg, 4.8 mmol, 1.2 equiv) at 25° C., and the resulting reaction mixture was subsequently stirred at room temperature for 1–2 h. A solution of NaB(OAc)$_3$H (1.02 g, 4.8 mmol, 1.2 equiv) in DMSO (8 mL) was then added dropwise into the reaction mixture at room temperature. The resulting reaction mixture was then stirred at room temperature for 3 h. When HPLC and TLC showed the reduction reaction was complete, the reaction mixture was quenched with a 10% of K$_2$CO$_3$ aqueous solution (30 mL) at room temperature, and the resulting mixture was stirred for an additional 1 h. The resulting precipitates were collected by filtration, washed with water (2×10 mL), and dried in vacuo to afford the crude, desired reductive amination product (28, 1.90 g, 2.184 g theoretical, 87% yield) as off-white powders. This crude product was subsequently recrystallized in acetonitrile/water (4:1) to afford the pure desired product (28, 1.485 g, 2.184 g theoretical, 68%) as white powders. For 28, CIMS m/z 547 (M$^+$+H, C$_{29}$H$_{25}$F$_3$N$_6$O$_2$).

Example 35

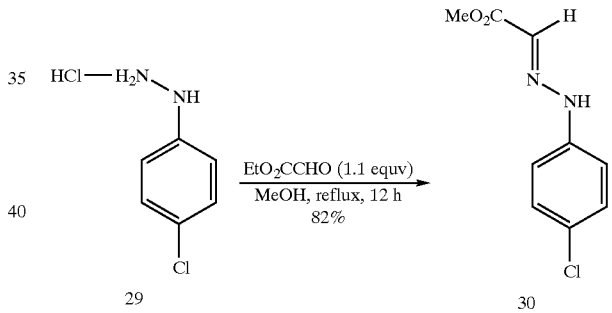

[(4-Chlorophenyl)hydrazono]acetic acid methyl ester (30). A suspension of 4-chloro-phenylhydrazine hydrochloride (29, 16.0 g, 89.4 mmol) in anhydrous MeOH(100 mL) was treated dropwise with a solution of ethylglycolate (50% solution in toluene, 20.06 g, 98.3 mmol, 1.1 equiv) in toluene at 25° C. under N$_2$. The resulting reaction mixture was then warmed to reflux for 12 h. When TLC and HPLC showed the reaction was deemed complete, the solvent was removed in vacuo. The residue was then treated with 50% of CH$_2$Cl$_2$ and hexane (v/v, 100 mL) at 25° C. for 30 min with good stirring. The pale-yellow solids were collected by filtration, washed with 50% of CH$_2$Cl$_2$ and hexane (v/v, 2×50 mL), and dried at 40–45° C. in vacuo for 12 h to afford the crude, desired [(4-chlorophenyl)hydrazono]acetic acid methyl ester (30, 15.6 g, 19.0 g theoretical, 82%), which was found to be pure enough to do the following reaction without further purification. For 30: CIMS m/z 211/213 (M$^+$–H, C$_9$H$_9$ClN$_2$O$_2$).

Example 36

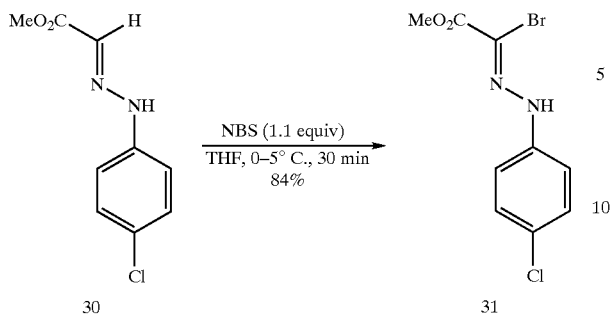

Bromo[(4-chlorophenyl)hydrazono]acetic acid methyl ester (31). A solution of [(4-chlorophenyl)hydrazono]acetic acid methyl ester (30, 13.0 g, 61.2 mmol) in anhydrous THF (100 mL) was treated with N-bromosuccinimide (NBS, 11.97 g, 67.3 mmol, 1.1 equiv) at 0–5° C. under $N_2$, and the resulting reaction mixture was stirred at 0–5° C. for an additional 30 min. When HPLC and TLC showed the reaction was deemed complete, the solvent was removed in vacuo. The residue was directly purified by column chromatography ($SiO_2$, 0–15% EtOAc/hexane gradient elution) to afford the desired bromo[(4-chlorophenyl)hydrazono]acetic acid methyl ester (31, 15.0 g, 17.84 g theoretical, 84%) as pale-yellow solids, which was found to be essentially pure to do the following cycloaddition reaction without further purification. For 31, CIMS m/z 290/292 ($M^+$–H, $C_9H_8BrClN_2O_2$).

Example 37

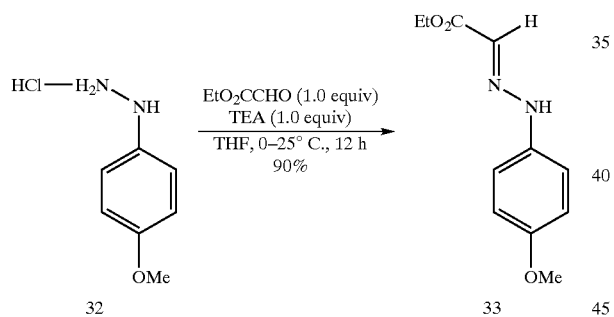

[(4-Methoxyphenyl)hydrazono]acetic acid ethyl ester (33). A suspension of 4-methoxy-phenylhydrazine hydrochloride (32, 14.0 g, 80.2 mmol) in anhydrous THF (100 mL) was treated with triethylamine (TEA, 8.10 g, 11.2 mL, 80.2 mmol, 1.0 equiv) before a solution of ethylglycolate (50% solution in toluene, 16.4 g, 80.2 mmol, 1.0 equiv) in toluene was dropwise added into the reaction mixture at 0–5° C. under $N_2$. The resulting reaction mixture was then stirred at 0–5° C. for 30 min before being gradually warmed to 25° C. for 12 h. When TLC and HPLC showed the reaction was deemed complete, the reaction mixture was filtered to collect triethylamine hydrochloride salt. The filtrates were concentrated in vacuo, and the resulting solids were collected by filtration. The crude solids were washed with water (2×50 mL) and 20% of EtOAc/hexane (2×50 mL), and dried at 40–45° C. in vacuo for 12 h to afford the crude, desired [(4-methoxyphenyl)hydrazono]acetic acid ethyl ester (33, 16.0 g, 17.80 g theoretical, 90%), which was found to be pure enough to do the following reaction without further purification. For 33: CIMS m/z 221 ($M^+$–H, $C_{11}H_{14}N_2O_3$).

Example 38

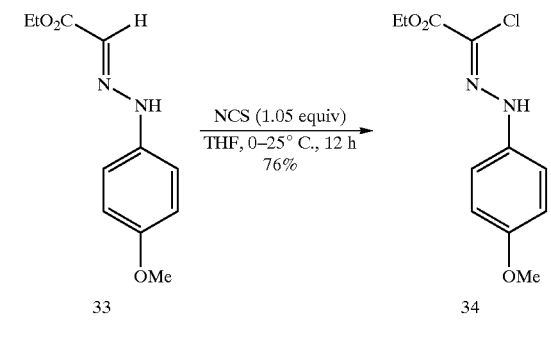

Chloro[(4-methoxyphenyl)hydrazono]acetic acid ethyl ester (34). Method A. A solution of [(4-methoxyphenyl) hydrazono]acetic acid ethyl ester (33, 4.0 g, 18.0 mmol) in anhydrous THF (40 mL) was treated with N-chlorosuccinimide (NCS, 2.52 g, 18.9 mmol, 1.05 equiv) at 0–5° C. under $N_2$, and the resulting reaction mixture was stirred at 0–5° C. for an additional 30 min before being gradually warmed to 25° C. for 12 h. When HPLC and TLC showed the reaction was deemed complete, the solvent was removed in vacuo. The residue was directly purified by column chromatography ($SiO_2$, 0–25% EtOAc/hexane gradient elution) to afford the desired chloro[(4-methoxyphenyl)hydrazono]acetic acid ethyl ester (34, 3.51 g, 4.62 g theoretical, 76%) as pale-yellow solids, which was found to be essentially pure to do the following reaction without further purification. For 34, CIMS m/z 255/257 ($M^+$–H, $C_{11}H_{13}ClN_2O_3$).

Example 39

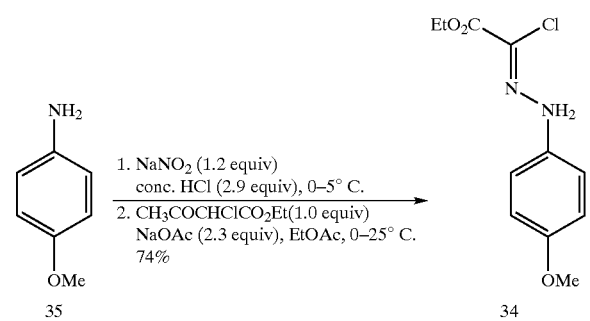

Chloro[(4-methoxyphenyl)hydrazono]acetic acid ethyl ester (34). Method B. A solution of 4-methoxyaniline (35, 31.0 g, 252 mmol) in water (100 mL) was treated with concentrated aqueous HCl solution (37%, 62 mL, 730 mmol, 2.9 equiv) at 0–5° C. under $N_2$, and the resulting reaction mixture was added dropwise an aqueous solution of sodium nitrite ($NaNO_2$, 20.9 g, 302.4 mmol, 1.2 equiv) in water (50 mL) at 0–5° C. The reaction mixture was subsequently stirred at 0–5° C. for an additional 1.5 h before being transferred into a mixture containing sodium acetate (NaOAc, 47.5 g, 579 mmol, 2.3 equiv), ethyl chloroacetoacetate (41.4 g, 34.8 mL, 252 mmol, 1.0 equiv) in ethyl acetate (200 mL) and water (100 mL) at 0–5° C. The resulting reaction mixture was then stirred at 0–5° C. for 30 min before being warmed up to room temperature for 12 h. When HPLC and TLC showed the reaction was deemed complete, the two layers were separated, and the organic phase was washed with sodium bicarbonate aqueous solution (2×50 mL), water (50 mL) and saturated sodium chloride aqueous solution (50 mL), dried over MgSO₄, and concentrated in vacuo. The residue was treated with 50% EtOAc/hexane (100 mL) to directly precipitate the crude product. The solids were collected by filtration to afford the crude desired chloro[(4-methoxyphenyl)hydrazono]acetic acid ethyl ester (34, 47.8 g, 64.62 g theoretical, 74%), which was found to be essentially pure to do the following reaction without further purification. This product was found to be identical with the material obtained from method A in every comparable aspect.

Example 40

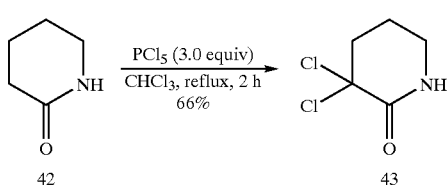

3,3-Dichloro-piperidin-2-one (43). A solution of piperidin-2-one (42, 25.0 g, 252.2 mmol) in CHCl₃ (250 mL) was treated with PCl₅ (158 g, 756.5 mmol, 3.0 equiv) at 0–5° C., and the resulting reaction mixture was stirred at 0–5° C. for 10 min before being warmed up to reflux for 2 h. When HPLC showed the reaction was complete, the reaction mixture was cooled down to 5–10° C. before being transferred into an ice water (500 mL) with caution. The resulting mixture was stirred at 0–5° C. for 1 h before being gradually warmed up to room temperature for 12 h. The two layers were separated, and the aqueous layer was extracted with CH₂Cl₂ (4×50 mL). The combined organic extracts were washed with saturated NaCl aqueous solution (50 mL), dried over MgSO₄, and concentrated in vacuo. The residual solids were treated with 30% EtOAc/hexane (50 mL) before being collected by filtration. The crude pale-yellow solids were dried in vacuo at 30–35° C. for 12 h to afford the desired 3,3-dichloro-piperidin-2-one (43, 27.96 g, 42.36 g theoretical, 66%) as bright-yellow oil, which solidified upon standing at room temperature in vacuo. For 43, CIMS m/z 166/170 (M⁺–H, C₅H₇Cl₂NO).

Example 41

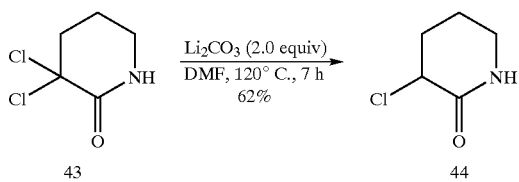

3-Chloro-5,6-dihydro-1H-pyridin-2-one (44). A solution of 3,3-dichloro-piperidin-2-one (43, 2.0 g, 11.9 mmol) in DMF (6 mL) was treated with Li₂CO₃ (1.76 g, 23.8 mmol, 2.0 equiv) at room temperature. The resulting mixture was then warmed up to 120° C. for 7 h. When HPLC showed the reaction was complete, the reaction mixture was cooled down to 25° C. before being treated with water (10 mL) and CH₂Cl₂ (20 mL) The mixture was stirred for 10 min before the two layers were separated. The aqueous layer was extracted with CH₂Cl₂ (3×10 mL), and the combined organic extracts were washed with saturated NaCl aqueous solution (5 mL), dried over MgSO₄, and concentrated in vacuo. The residual solids were treated with 30% EtOAc/ hexane before being collected by filtration. The crude desired 3-chloro-5,6-dihydro-1H-pyridin-2-one (44, 970 mg, 1.56 g theoretical, 62%) was obtained as bright-yellow solids, which was found to be essentially pure by HPLC and was directly employed in the following reaction without further purification. For 44, CIMS m/z 130/132 (M⁺–H, C₅H₆ClNO).

Example 42

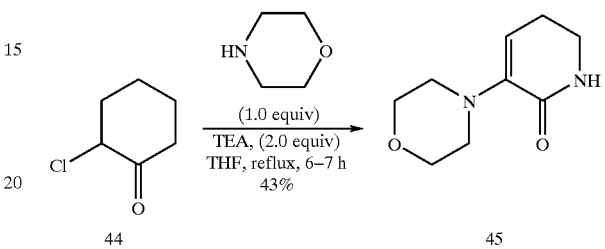

3-Morpholin-4-yl-5,6-dihydro-1H-pyridin-2-one (45). A solution of 3-chloro-5,6-dihydro-1H-pyridin-2-one (44, 1.0 g, 7.6 mmol) in THF (4 mL) was treated with morpholine (663 mg, 0.67 mL, 7.6 mmol, 1.0 equiv) and triethylamine (TEA, 1.54 g, 2.1 mL, 15.2 mmol, 2.0 equiv) at room temperature, and the resulting reaction mixture was warmed up to reflux for 6 h. When HPLC and TLC showed the reaction was deemed complete, the reaction mixture was quenched with water (10 mL) and EtOAc (20 mL), and the resulting mixture was stirred at room temperature for 10 min. The two layers were separated, and the aqueous layer was extracted with EtOAc (3×20 mL). The combined organic extracts were washed with saturated NaCl aqueous solution (5 mL), dried over MgSO₄, and concentrated in vacuo. The residue was then purified by flash column chromatography (SiO₂, 15–40% EtOAc/hexane gradient elution) to afford the desired 3-morpholin-4-yl-5,6-dihydro-1H-pyridin-2-one (45, 595 mg, 1.384 g theoretical, 43%) as pale-yellow oil, which solidified upon standing at room temperature in vacuo and was found to be essentially pure to do the following reaction without further purification. For 45, CIMS m/z 181 (M⁺–H, C₉H₁₄N₂O₂).

Example 43

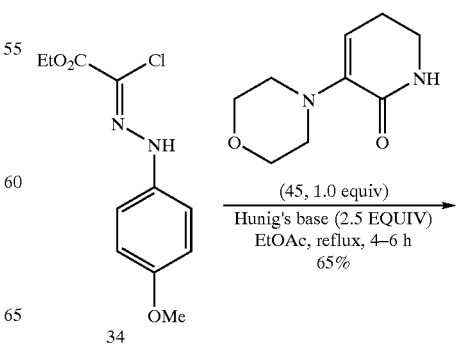

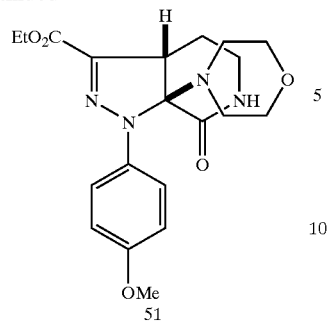

51

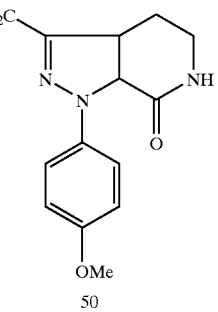

50

1-(4-Methoxy-phenyl)-7-oxo-4,5,6,7-tetrahydro-1H-pyrazolo[3,4-c]pyridine-3-carboxylic acic ethyl ester (50). Method B. A solution of 1-(4-methoxy-phenyl)-7a-morpholin-4-yl-7-oxo-3a,4,5,6,7,7a-hexahydro-1H-pyrazolo[3,4-c]pyridin-3-carboxylic acid ethyl ester (51, 402 mg, 1.0 mmol) in methylene chloride (CH$_2$Cl$_2$, 4 mL) was treated with trifluoroacetic acid (TFA, 1.0 mL) at 25° C., and the resulting reaction mixture was stirred at 25° C. for an additional 30 min. When HPLC and TLC showed the reaction was complete, the solvents were removed in vacuo. The residue was directly purified by flash column chromatography (SiO$_2$, 5–30% EtOAc/hexane gradient elution) to afford the desired elimination product (50, 299 mg, 315 mg theoretical, 95%) as a pale-yellow oil, which solidified upon standing at room temperature in vacuo. This material was found to be identical with the product obtained from method A in every comparable aspect.

1-(4-Methoxy-phenyl)-7a-morpholin-4-yl-7-oxo-3a,4,5,6,7,7a-hexahydro-1H-pyrazolo[3,4-c]pyridin-3-carboxylic acid ethyl ester (51). A solution of chloro[(4-methoxyphenyl)hydrazono]acetic acid ethyl ester (34, 582 mg, 2.0 mmol) in ethyl acetate (EtOAc, 10 mL) was treated with 3-morpholin-4-yl-5,6-dihydro-1H-pyridin-2-one (45, 364 mg, 2.0 mmol, 1.0 equiv) at 0–5° C. under N$_2$, and the resulting reaction mixture was treated with triethylamine (TEA, 505 mg, 0.70 mL, 5.0 mmol, 2.5 equiv) at 0–5° C. under N$_2$. The reaction mixture was then warmed up to room temperature for 30 min before being warmed up to reflux for an additional 6 h. When HPLC and TLC showed that the reaction was complete, the reaction mixture was treated with water (10 mL) and EtOAc (10 mL). The two layers were separated, and the aqueous layer was extracted with EtOAc (3×10 mL). The combined organic extracts were washed with saturated NaCl aqueous solution (5 mL), dried over MgSO$_4$, and concentrated in vacuo. The residue was directly purified by flash column chromatography (SiO$_2$, 15–40% EtOAc/hexane gradient elution) to afford the desired 1-(4-methoxy-phenyl)-7a-morpholin-4-yl-7-oxo-3a,4,5,6,7,7a-hexahydro-1H-pyrazolo[3,4-c]pyridin-3-carboxylic acid ethyl ester (51, 523 mg, 805 mg theoretical, 65%) as pale-yellow oil, which solidified upon standing at room temperature in vacuo. For 51, CIMS m/z 401 (M$^+$–H, C$_{20}$H$_{26}$N$_4$O$_5$).

Example 44

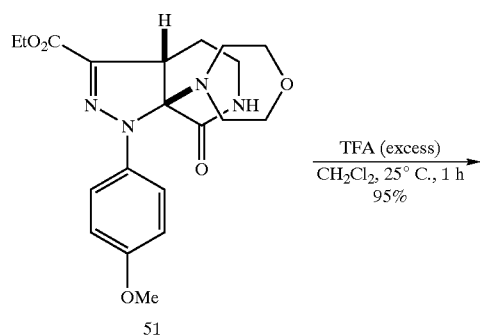

51

TFA (excess)
CH$_2$Cl$_2$, 25° C., 1 h
95%

Example 45

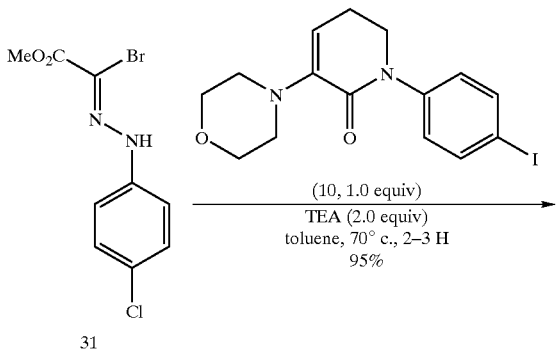

31

(10, 1.0 equiv)
TEA (2.0 equiv)
toluene, 70° c., 2–3 H
95%

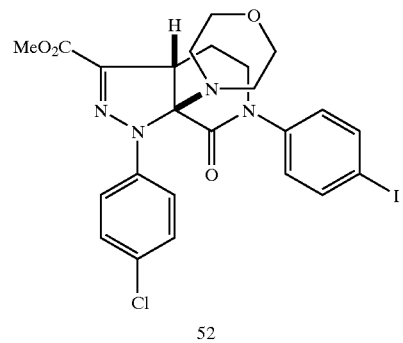

52

1-(4-Chloro-phenyl)-6-(4-iodo-phenyl)-7a-morpholin-4-yl-7-oxo-3a,4,5,6,7,7a-hexahydro-1H-pyrazolo[3,4-c]pyridine-3-carboxylic acid methyl ester (52). A solution of bromo[(4-chlorophenyl)hydrazono]acetic acid methyl ester (31, 582 mg, 2.0 mmol) in toluene (6 mL) was treated with 1-(4-iodo-phenyl)-3-morpholin-4-yl-5,6-dihydro-1H-pyridin-2-one (10, 768 mg, 2.0 mmol, 1.0 equiv) at 0–5° C. under $N_2$, and the resulting reaction mixture was treated with triethylamine (TEA, 404 mg, 0.56 mL, 4.0 mmol, 2.0 equiv) at 0–5° C. under $N_2$. The reaction mixture was then warmed up to room temperature for 30 min before being warmed up to 70° C. for an additional 3 h. When HPLC and TLC showed that the reaction was complete, the reaction mixture was treated with water (10 mL) and EtOAc (10 mL). The two layers were separated, and the aqueous layer was extracted with EtOAc (2×10 mL). The combined organic extracts were washed with saturated NaCl aqueous solution (5 mL), dried over $MgSO_4$, and concentrated in vacuo. The residue was directly purified by flash column chromatography ($SiO_2$, 15–30% EtOAc/hexane gradient elution) to afford the desired 1-(4-chloro-phenyl)-6-(4-iodo-phenyl)-7a-morpholin-4-yl-7-oxo-3a,4,5,6,7,7a-hexahydro-1H-pyrazolo[3,4-c]pyridine-3-carboxylic acid methyl ester (52, 1.13 g, 1.19 g theoretical, 95%) as pale-yellow oil, which solidified upon standing at room temperature in vacuo. For 52, CIMS m/z 595/597 ($M^+$+H, $C_{24}H_{24}ClIN_4O_4$).

Example 46

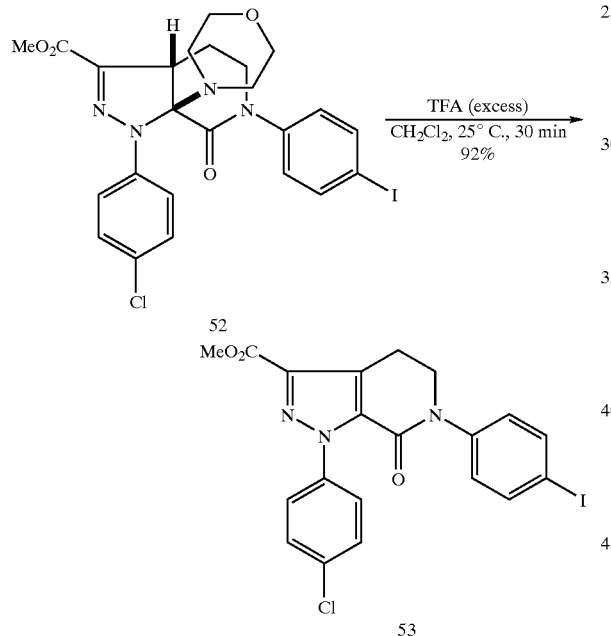

Example 47

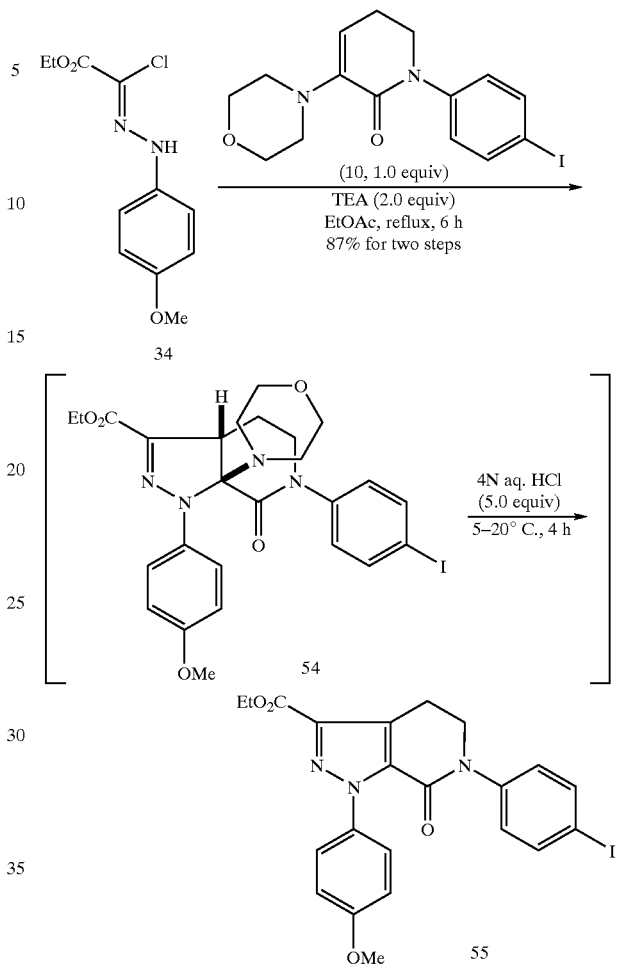

1-(4-Chloro-phenyl)-6-(4-iodo-phenyl)-7-oxo-4,5,6,7-tetrahydro-1H-pyrazolo[3,4-c]pyridine-3-carboxylic acid methyl ester (53). A solution of 1-(4-chloro-phenyl)-6-(4-iodo-phenyl)-7a-morpholin-4-yl-7-oxo-3a,4,5,6,7,7a-hexahydro-1H-pyrazolo[3,4-c]pyridine-3-carboxylic acid methyl ester (52, 595 mg, 1.0 mmol) in methylene chloride ($CH_2Cl_2$, 4 mL) was treated with trifluoroacetic acid (TFA, 1.0 mL) at 25° C., and the resulting reaction mixture was stirred at 25° C. for an additional 30 min. When HPLC and TLC showed the reaction was complete, the solvents were removed in vacuo. The residue was directly purified by flash column chromatography ($SiO_2$, 5–20% EtOAc/hexane gradient elution) to afford the desired elimination product (53, 467 mg, 508 mg theoretical, 92%) as a pale-yellow oil, which solidified upon standing at room temperature in vacuo. For 53, CIMS m/z 508/510 ($M^+$+H, $C_{20}H_{15}ClIN_3O_3$).

1-(4-Methoxy-phenyl)-6-(4-iodo-phenyl)-7-oxo-4,5,6,7-tetrahydro-1H-pyrazolo[3,4-c]pyridine-3-carboxylic acid ethyl ester (55). A solution of chloro[(4-methoxyphenyl)hydrazono]acetic acid ethyl ester (34, 100 g, 0.39 mol) in EtOAc (800 mL) was treated with 1-(4-iodo-phenyl)-3-morpholin-4-yl-5,6-dihydro-1H-pyridin-2-one (10, 150 g, 0.39 mol, 1.0 equiv) at 0–5° C. under $N_2$, and the resulting reaction mixture was treated with triethylamine (TEA, 78.8 g, 109 mL, 0.78 mol, 2.0 equiv) at 0–5° C. under $N_2$. The reaction mixture was then warmed up to room temperature for 30 min before being warmed up to reflux for an additional 6 h. When HPLC and TLC showed that the reaction was complete, the reaction mixture was cooled down to 5–10° C. before being treated dropwise with 4.0 N aqueous HCl solution (488 mL, 1.95 mol, 5.0 equiv) at 0–5° C. The resulting mixture was stirred at 5–20° C. for 4 h. The resulting slurry was then treated with water (400 mL) before being stirred at 5–20° C. for an additional 30 min. The solids were collected by filtration, washed with water (2×200 mL) and 50% of isopropyl acetate/hexane (2×200 mL), dried in vacuo at 40–45° C. for 12 h. The crude desired 1-(4-methoxy-phenyl)-6-(4-iodo-phenyl)-7-oxo-4,5,6,7-tetrahydro-1H-pyrazolo[3,4-c]pyridine-3-carboxylic acid ethyl ester (55, 175.5 g, 201.8 g theoretical, 87% for two steps) was obtained as pale-yellow solids, which was found to be essentially pure to do the following reaction without further purification. For 55, CIMS m/z 518 ($M^+$+H, $C_{22}H_{20}IN_3O_4$).

Example 48

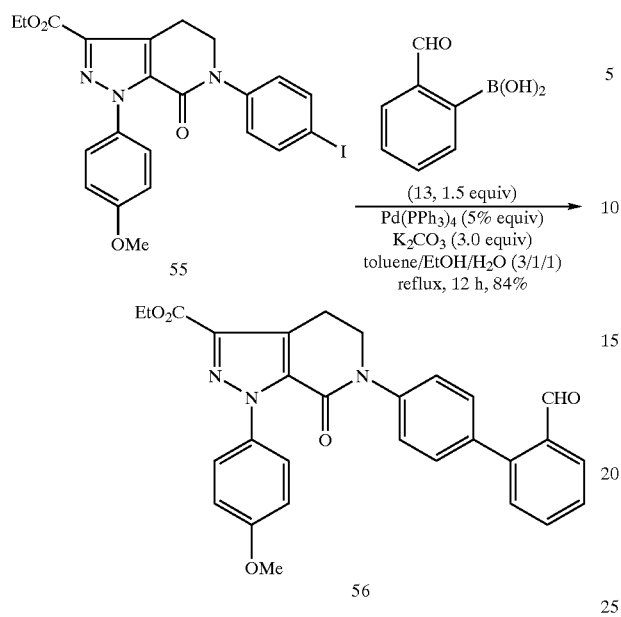

6-(2'-Formyl-biphenyl-4-yl)-1-(4-methoxy-phenyl)-7-oxo-4,5,6,7-tetrahydro-1H-pyrazolo[3,4-c]pyridine-3-carboxylic acid ethyl ester (56). Method A. A suspension 1-(4-methoxy-phenyl)-6-(4-iodo-phenyl)-7-oxo-4,5,6,7-tetrahydro-1H-pyrazolo[3,4-c]pyridine-3-carboxylic acid ethyl ester (55, 2.0 g, 3.87 mmol), 2-formylphenylboronic acid (13, 870 mg, 5.81 mmol, 1.5 equiv), and $K_2CO_3$ (1.60 g, 11.6 mmol, 3.0 equiv) in toluene (18 mL), ethanol (6 mL) and $H_2O$ (6 mL) at room temperature was degassed three times under a steady nitrogen stream before being treated with $Pd(PPh_3)_4$ (22 mg, 0.02 mmol, 5% equiv) at room temperature under $N_2$. The reaction mixture was subsequently degassed three times again before being warmed to reflux for 12 h. When HPLC showed the Suzuki coupling reaction was complete, the reaction mixture was cooled down to 5–10° C. before being treated with water (20 mL) at 5–10° C. with good stirring. The mixture was stirred for an additional 1 h at 5–10° C. before the solids were collected by filtration. The wet cake was then thoroughly washed with water (2×30 mL) and 30% EtOAc/hexane (2×20 mL), dried in vacuo at 40–45° C. for 12 h to afford the crude desired 6-(2'-formyl-biphenyl-4-yl)-1-(4-methoxy-phenyl)-7-oxo-4,5,6,7-tetrahydro-1H-pyrazolo[3,4-c]pyridine-3-carboxylic acid ethyl ester (56, 1.61 g, 1.915 g theoretical, 84%) as off-white solids, which was found to be pure enough to do the following reaction without further purification. For 56, CIMS m/z 496 (M$^+$+H, $C_{29}H_{25}N_3O_5$).

Example 49

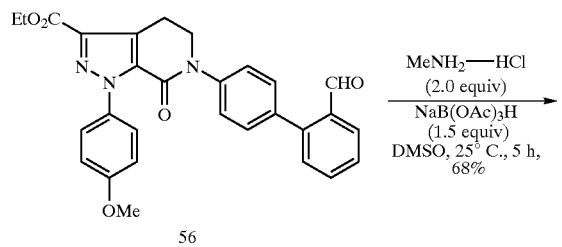

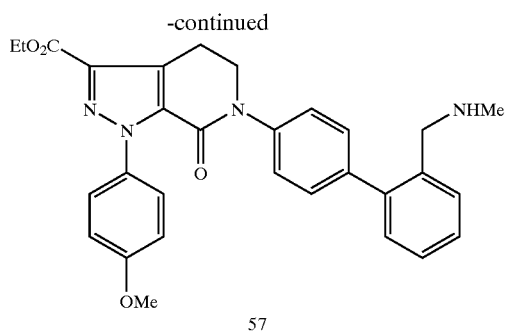

1-(4-Methoxy-phenyl)-6-(2'-methylaminomethyl-biphenyl-4-yl)-7-oxo-4,5,6,7-tetrahydro-1H-pyrazolo[3,4-c]pyridine-3-carboxylic acid ethyl ester (57). A suspension of 6-(2'-formyl-biphenyl-4-yl)-1-(4-methoxy-phenyl)-7-oxo-4,5,6,7-tetrahydro-1H-pyrazolo[3,4-c]pyridine-3-carboxylic acid ethyl ester (56, 26.1 g, 52.7 mmol) in DMSO (160 mL) was treated with methylamine hydrochloride salt (7.1 g, 105.4 mmol, 2.0 equiv) at 25° C., and the resulting reaction mixture was subsequently warmed up to 40° C. for 30 min to form a clear solution. A solution of NaB(OAc)$_3$H (16.8 g, 79.1 mmol, 1.5 equiv) in DMSO (90 mL) was then added dropwise into the reaction mixture at 25° C. The resulting reaction mixture was then stirred at room temperature for 5 h. When HPLC and TLC showed the reduction reaction was complete, the reaction mixture was quenched with a 10% of aqueous citric acid solution (100 mL) at room temperature, and the resulting mixture was stirred for 1 h before ethyl acetate (200 ml) was introduced into the mixture. The two layers were separated, and the aqueous layer was basified by addition of a 10% of aqueous $K_2CO_3$ solution to pH=10 before being extracted with ethyl acetate (3×100 mL), and the combined organic extracts were washed with saturated aqueous NaCl solution (50 mL), dried over MgSO$_4$, and concentrated in vacuo. The thick slurry was further titrated with 40% EtOAc/hexane (100 mL) to precipitate the corresponding reductive amination product. The solids were collected by filtration and washed with 40% EtOAc/hexane (2×50 mL), dried in vacuo at 40–45° C. for 12 to afford the crude desired 1-(4-methoxy-phenyl)-6-(2'-methylaminomethyl-biphenyl-4-yl)-7-oxo-4,5,6,7-tetrahydro-1H-pyrazolo[3,4-c]pyridine-3-carboxylic acid ethyl ester (57, 18.3 g, 26.90 g theoretical, 68% yield) as off-white powders. This crude product was directly used in the following reaction without further purification. For 57, CIMS m/z 511 (M$^+$+H, $C_{30}H_{30}N_4O_4$).

Example 50

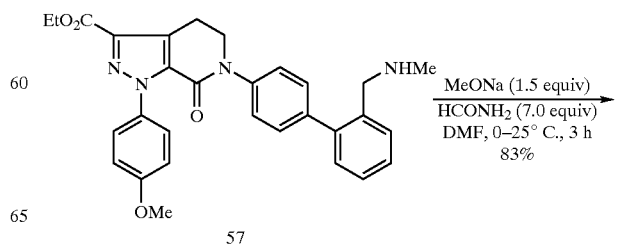

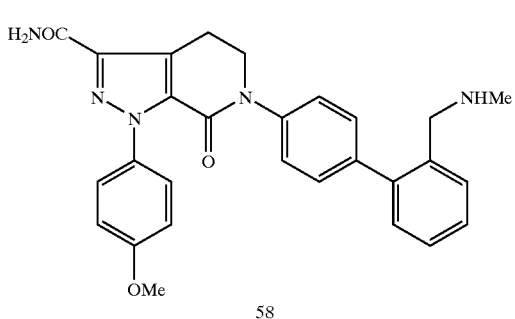

58

1-(4-Methoxy-phenyl)-6-(2'-methylaminomethyl-biphenyl-4-yl)-7-oxo-4,5,6,7-tetrahydro-1H-pyrazolo[3,4-c]pyridine-3-carboxylic acid amide (58). A solution of 1-(4-methoxy-phenyl)-6-(2'-methylaminomethyl-biphenyl-4-yl)-7-oxo-4,5,6,7-tetrahydro-1H-pyrazolo[3,4-c]pyridine-3-carboxylic acid ethyl ester (57, 13.5 g, 26.4 mmol) in DMF (50 mL) was treated with formamide (8.32 g, 6.2 mL, 184.8 mmol, 7.0 equiv) at room temperature, and the resulting reaction mixture was cooled down to 0–5° C. before being treated dropwise with a solution of MeONa (8.6 g, 9.05 mL, 39.6 mmol, 1.5 equiv) in methanol at 0–5° C. The resulting reaction mixture was stirred at 0–5° C. for 30 min before being gradually warmed up to room temperature for an additional 3 h. When HPLC and TLC showed the reaction was complete, the reaction mixture was slowly poured into water (600 mL). The resulting mixture was then stirred at room temperature for 1 h to precipitate the desired product. The solids were collected by filtration, washed with water (2×100 mL) and methyl tert-butyl ether (2×100 mL), dried in vacuo at 40–45° C. for 12 h to afford crude desired 1-(4-methoxy-phenyl)-6-(2'-methylaminomethyl-biphenyl-4-yl)-7-oxo-4,5,6,7-tetrahydro-1H-pyrazolo[3,4-c]pyridine-3-carboxylic acid amide (58, 10.55 g, 12.71 g theoretical, 83%). This crude solids were subsequently recrystallized in a mixture of ethanol and methanol to afford the pure product. For 58, CIMS m/z 482 (M++H, $C_{28}H_{27}N_5O_3$).

Example 51

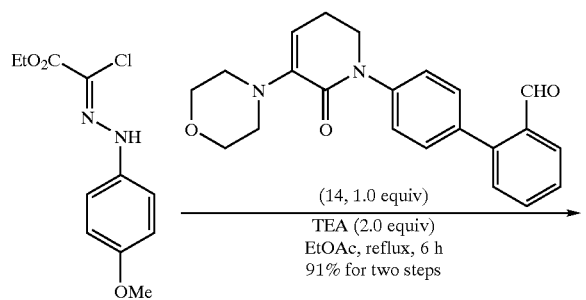

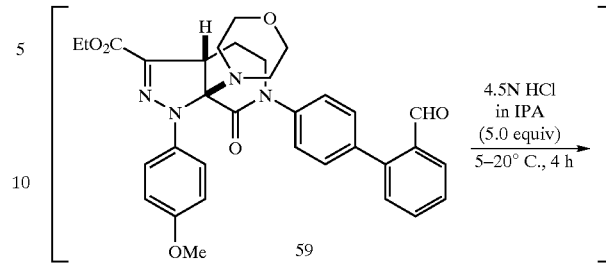

6-(2'-Formyl-biphenyl-4-yl)-1-(4-methoxy-phenyl)-7-oxo-4,5,6,7-tetrahydro-1H-pyrazolo[3,4-c]pyridine-3-carboxylic acid ethyl ester (56). Method B. A solution of chloro[(4-methoxyphenyl)hydrazono]acetic acid ethyl ester (34, 150 g, 0.584 mol) in EtOAc (1500 mL) was treated with N-[4-(2-formyl)phenyl]phenyl-3-morpholino-5,6-dihydro-2H-pyridin-2-one (14, 211.7 g, 0.584 mol, 1.0 equiv) at 0–5° C. under $N_2$, and the resulting reaction mixture was treated with triethylamine (TEA, 118 g, 162.5 mL, 1.168 mol, 2.0 equiv) at 0–5° C. under $N_2$. The reaction mixture was then warmed up to room temperature for 30 min before being warmed up to reflux for an additional 6 h. When HPLC and TLC showed that the reaction was complete, the reaction mixture was cooled down to 5–10° C. before being treated dropwise with a 4.5 N HCl solution in isopropyl alcohol (649 mL, 2.92 mol, 5.0 equiv) at 0–5° C. The resulting mixture was then treated with additional isopropyl alcohol (400 mL) and stirred at 5–20° C. for 4 h. The solids were collected by filtration, washed with water (2×800 mL) and 50% of isopropyl acetate/hexane (2×500 mL), dried in vacuo at 40–45° C. for 12 h. The crude desired 6-(2'-formyl-biphenyl-4-yl)-1-(4-methoxy-phenyl)-7-oxo-4,5,6,7-tetrahydro-1H-pyrazolo[3,4-c]pyridine-3-carboxylic acid ethyl ester (56, 263.3 g, 289.4 g theoretical, 91% for two steps) was obtained as pale-yellow solids, which was found to be essentially pure to do the following reaction without further purification. This material was found to be identical with the product made from method A in every comparable aspect.

Example 52

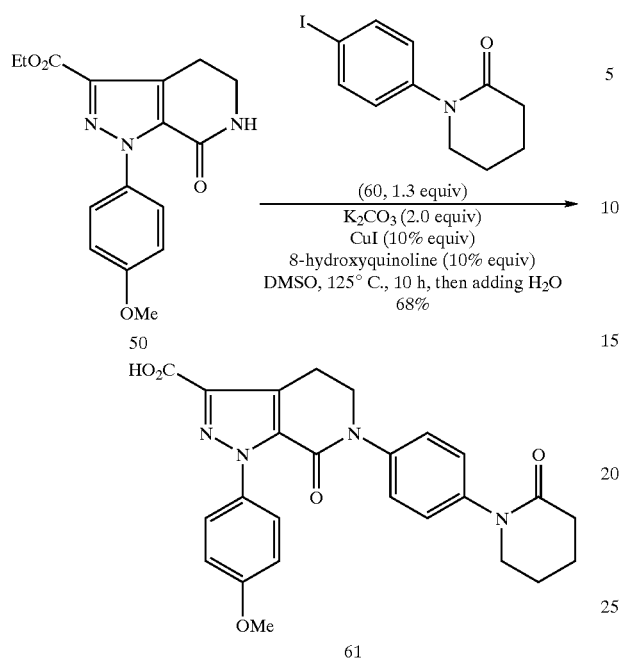

1-(4-Methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid (61). A solution of 1-(4-methoxy-phenyl)-7-oxo-4,5,6,7-tetrahydro-1H-pyrazolo[3,4-c]pyridine-3-carboxylic acid ethyl ester (50, 2.0 g, 6.4 mmol), 1-(4-iodophenyl)-piperidin-2-one (60, 2.5 g, 8.3 mmol, 1.3 equiv), and $K_2CO_3$ (325 mesh powder, 1.80 g, 12.8 mmol, 2.0 equiv) in DMSO (35 mL) was degassed three times under a steady nitrogen stream before being treated with CuI (244 mg, 1.3 mmol, 20% equiv) and 8-hydroxyquinoline (189 mg, 1.3 mmol, 20% equiv) under $N_2$. The resulting reaction mixture was subsequently degassed three times again before being warmed up to 125° C. for 10 h. When HPLC showed the coupling reaction was complete, the reaction mixture was cooled down to 5–10° C. before being treated with 14% $NH_4OH$ aqueous solution (30 mL) and ethyl acetate (30 mL) at 5–10° C. with good stirring. The mixture was stirred for an additional 1 h at 5–10° C. The mixture was filtered through a Celite® bed and the Celite® bed was washed with water (2×10 mL). The two layers of the filtrates were separated, and the aqueous layer was acidified by 1 N aqueous HCl solution to pH=4. The mixture was subsequently stirred at 5–10° C. for an additional 1 h. The solids were collected by filtration, washed with water (2×5 mL), and dried in vacuo at 40–45° C. for 12 h to afford the crude desired 1-(4-methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid (61, 2.0 g, 2.95 g theoretical, 68%), which was found to be pure enough to do the following reaction without further purification. For 61, CIMS m/z 461 ($M^+$+H, $C_{25}H_{24}N_4O_5$).

Example 53

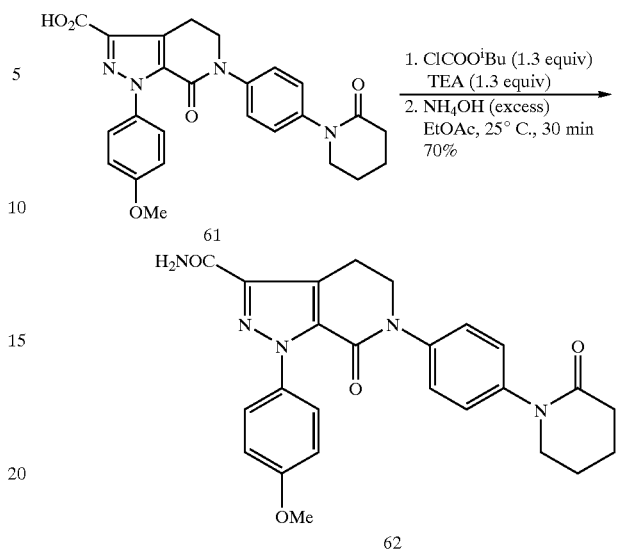

1-(4-Methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid amide (62). Method A. A suspension of 1-(4-methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid (61, 1.5 g, 3.3 mmol) in EtOAc (20 mL) was treated with triethylamine (TEA, 433 mg, 0.60 mL, 4.3 mmol, 1.3 equiv) at room temperature, and the resulting reaction mixture was treated dropwise with iso-butyl chloroformate (587 mg, 0.55 mL, 4.3 mmol, 1.3 equiv) at room temperature. The resulting reaction mixture was subsequently stirred at room temperature for an additional 30 min. When TLC and HPLC showed the mixed anhydride formation reaction was complete, the reaction mixture was poured into a cold (0–5° C.) ammonium hydroxide solution ($NH_4OH$, 28% aqueous solution, 25 mL) with good stirring. The resulting mixture was stirred at room temperature for an additional 4 h. The solids were collected by filtration, washed with a mixture of methanol and water (1:1 v/v, 2×20 mL), and dried in vacuo at 40–45° C. for 12 h to afford the crude desired 1-(4-methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid amide (62, 1.06 g, 1.52 g theoretical, 70%) as off-white crystals. For 62, CIMS m/z 460 ($M^+$+H, $C_{25}H_{25}N_5O_4$).

Example 54

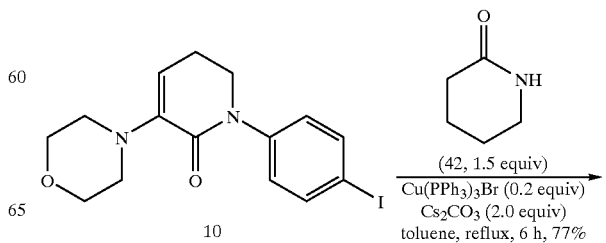

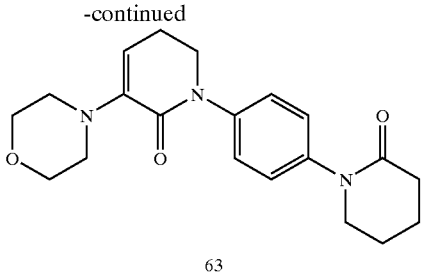

63

3-Morpholin-4-yl-1-[4-(2-oxo-piperidin-1-yl)-phenyl]-5,6-dihydro-1H-pyridin-2-one (63).

Part A. Preparation of soluble copper(I) catalyst, Cu(PPh$_3$)$_3$Br. In an Erlenmeyer flask equipped with a Teflon stir bar, methanol (100 mL) was heated to boiling and triphenylphosphine (6.0 g, 22.4 mmol, 4.25 equiv) was slowly added to the stirring methanol. After the complete dissolution of triphenylphosphine, CuBr$_2$ (1.24 g, 5.27 mmol) was added as a solid, in portions. No special precautions were taken for the exclusion of air. Upon addition of the copper bromide, a white precipitate was formed. After the completion of the addition, the contents were stirred for 10 min and the flask was allowed to cool to ambient temperature. The reaction mixture was then filtered through a Buchner funnel and the white residue was washed repeatedly with ethanol and then diethyl ether. The resultant white solid was dried under dynamic vacuum to afford Cu(PPh$_3$)$_3$Br (5.73 g, 6.74 g theoretical, 85%; mp 164° C.) as the soluble copper(I) catalyst.

Part B. Soluble copper(I)-catalyzed Ullmann coupling reaction. A suspension of 1-(4-iodo-phenyl)-3-morpholin-4-yl-5,6-dihydro-1H-pyridin-2-one (10, 2.2 g, 5.73 mmol), piperidin-2-one (42, 851 mg, 8.59 mmol, 1.5 equiv), and Cs$_2$CO$_3$ (3.73 g, 11.46 mmol, 2.0 equiv) in toluene (15 mL) was treated with Cu(PPh$_3$)$_3$Br (1.065 g, 1.146 mmol, 20% equiv) at room temperature under N$_2$, and the resulting reaction mixture was degassed three times under a steady stream of nitrogen. The reaction mixture was warmed up to reflux for 6 h. When HPLC showed the Ullmann coupling reaction was complete, the reaction mixture was cooled down to 5–10° C. before being quenched with 14% of ammonium hydroxide aqueous solution (20 mL) and EtOAc (30 mL) at 5–10° C. The mixture was stirred for an additional 4 h at 25° C. The two layers were then separated, and the aqueous layer, was extracted with EtOAc (3×20 mL). The combined organic extracts were washed with saturated NaCl aqueous solution (10 mL), dried over MgSO$_4$, and concentrated in vacuo. The residue was directly purified by flash column chromatography (SiO$_2$, 15–40% EtOAc/hexane gradient elution) to afford the desired 3-morpholin-4-yl-1-[4-(2-oxo-piperidin-1-yl)-phenyl]-5,6-dihydro-1H-pyridin-2-one (63, 1.568 g, 2.036 g theoretical, 77%) as a pale-yellow oil, which solidified upon standing at room temperature in vacuo. For 63, CIMS m/z 356 (M$^+$+H, C$_2$OH$_{25}$N$_3$O$_3$).

Example 55

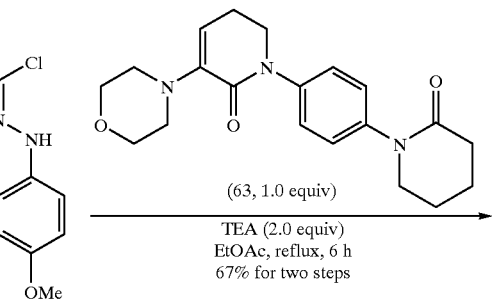

1-(4-Methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid ethyl ester (65). A solution of chloro[(4-methoxyphenyl)hydrazono]acetic acid ethyl ester (34, 470 mg, 1.3 mmol) in EtOAc (4 mL) was treated with 3-morpholin-4-yl-1-[4-(2-oxo-piperidin-1-yl)-phenyl]-5,6-dihydro-1H-pyridin-2-one (63, 334 mg, 1.3 mmol, 1.0 equiv) at 0–5° C. under N$_2$, and the resulting reaction mixture was treated with triethylamine (TEA, 263 mg, 0.33 mL, 2.6 mmol, 2.0 equiv) at 0–5° C. under N$_2$. The reaction mixture was then warmed up to room temperature for 30 min before being warmed up to reflux for an additional 6 h. When HPLC and TLC showed that the reaction was complete, the reaction mixture was cooled down to 5–10° C. before being treated dropwise with a 4.0 N aqueous HCl solution (1.7 mL, 6.5 mmol, 5.0 equiv) at 0–5° C. The resulting mixture was stirred at 5–20° C. for 4 h. The resulting slurry was then treated with water (10 mL) and EtOAc (10 mL) before the two layers were separated. The aqueous layer was extracted with EtOAc (2×10 mL). The combined organic extracts were washed with saturated NaCl aqueous solution (5 mL), dried over MgSO$_4$, and concentrated in vacuo. The residue was directly purified by flash column chromatography (SiO$_2$, 15–40% EtOAc/hexane gradient elution) to afford the desired 1-(4-methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid ethyl ester (65, 423 mg, 635 mg theoretical, 67% for two steps) as pale-yellow solids, which solidified upon standing in vacuo at room temperature. For 65, CIMS m/z 489 (M$^+$+H, $C_{27}H_{28}N_4O_5$).

Example 56

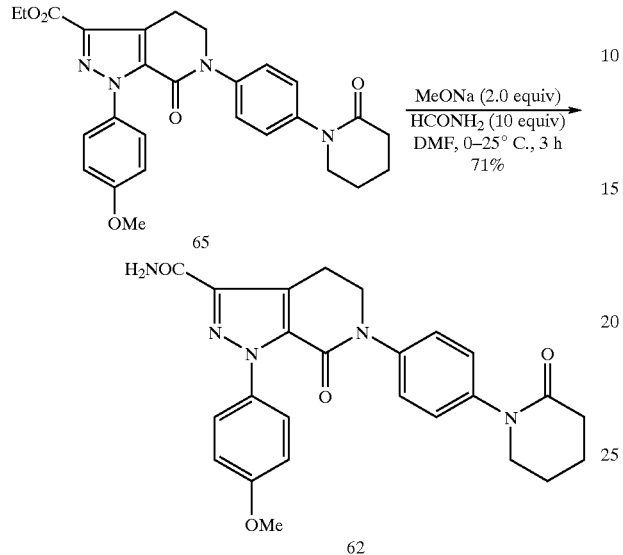

1-(4-Methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid amide (62). Method B. A solution of 1-(4-methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid ethyl ester (65, 977 mg, 2.0 mmol) in DMF (5 mL) was treated with formamide (901 mg, 0.8 mL, 20 mmol, 10.0 equiv) at room temperature, and the resulting reaction mixture was cooled down to 0–5° C. before being treated dropwise with a solution of MeONa (864 mg, 0.92 mL, 4.0 mmol, 2.0 equiv) in methanol at 0–5° C. The resulting reaction mixture was stirred at 0–5° C. for 30 min before being gradually warmed up to room temperature for an additional 3 h. When HPLC and TLC showed the reaction was complete, the reaction mixture was slowly poured into water (20 mL). The resulting mixture was then stirred at room temperature for 1 h to precipitate the desired product. The solids were collected by filtration, washed with water (2×10 mL) and methyl tert-butyl ether (2×10 mL), dried in vacuo at 40–45° C. for 12 h to afford the crude desired 1-(4-methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid amide (62, 653 mg, 919 mg theoretical, 71%) as off-whit crystals. This product was found to be identical with the material prepared from method A.

Numerous modifications and variations of the present invention are possible in light of the above teachings. It is therefore to be understood that within the scope of the appended claims, the invention may be practiced otherwise than as specifically described herein.

What is claimed is:

1. A process for preparing a compound of formula IV:

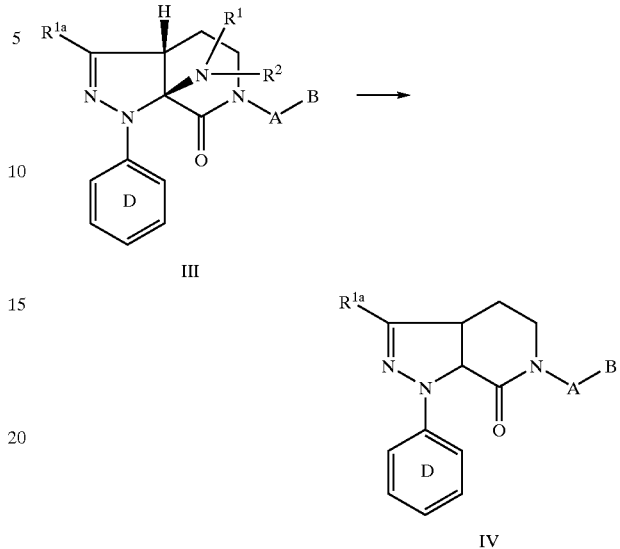

the process comprising:
(b) contacting a compound of formula III with an acid to form a compound of formula IV;

wherein:
ring D is selected from 4-chlorophenyl, 4-methoxyphenyl, 2-cyanophenyl, 2-(aminomethyl)phenyl, 2-(PgNHCH$_2$)phenyl, 3-cyanophenyl, 3-(aminomethyl)phenyl, 3-(PgNHCH$_2$)phenyl, 3-cyano-4-fluorophenyl, (3-amino)benz[d]isoxazol-6-yl, and (3-PgNH)benz[d]isoxazol-6-yl;

Pg is an amine protecting group;

$R^1$ and $R^2$ are selected from $C_{1-6}$ alkyl, cyclopropyl, cyclobutyl, cyclopentyl, cyclohexyl, phenyl, and benzyl;

alternatively, NR$^1$R$^2$ is a 3–8 membered ring consisting of: carbon atoms, N, and 0–1 O atoms;

$R^{1a}$ is selected from H, CH$_3$, CH$_2$CH$_3$, CH$_2$CH$_2$CH$_3$, CH$_2$F, CH$_2$Cl, Br, CH$_2$Br, —CN, CH$_2$CN, CF$_3$, CH$_2$CF$_3$, CH$_2$OCH$_3$, CO$_2$CH$_3$, CH$_2$CO$_2$CH$_3$, CO$_2$CH$_2$CH$_3$, CH$_2$CO$_2$CH$_2$CH$_3$, CH$_2$SCH$_3$, S(O)CH$_3$, CH$_2$S(O)CH$_3$, S(O)$_2$CH$_3$, CH$_2$S(O)$_2$CH$_3$, C(O)NH$_2$, CH$_2$C(O)NH$_2$, SO$_2$NH$_2$, CH$_2$SO$_2$NH$_2$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, CH$_2$-imidazol-1-yl, 1,2,3,4-tetrazol-1-yl, 1,2,3,4-tetrazol-5-yl, CH$_2$-1,2,3,4-tetrazol-1-yl, and CH$_2$-1,2,3,4-tetrazol-5-yl, provided that $R^{1a}$ forms other than an N-halo, N—N, N—S, N—O, or N—CN bond;

A is selected from phenyl substituted with 0–1 $R^4$, pyridyl substituted with 0–1 $R^4$, and pyrimidyl substituted with 0–1 $R^4$;

B is selected from B$^1$, Cl, Br, I, mesylate, tosylate, OSO$_2$Ph, CH$_2$Br, CH$_2$OH, and CHO;

alternatively, A-B is hydrogen;

B$^1$ is Y or X—Y;

X is selected from $C_{1-4}$ alkylene, —CR$^2$(CHR$^2$R$^{2b}$)(CH$_2$)$_t$—, —C(O)—, —CR$^2$(OR$^2$)—, —CR$^2$(SR$^2$)—, —C(O)CR$^2$R$^{2a}$—, —CR$^2$R$^{2a}$C(O), —S(O)$_p$—, —S(O)$_p$CR$^2$R$^{2a}$—, —CR$^2$R$^{2a}$S(O)$_p$—, —S(O)$_2$NR$^2$—, —NR$^2$S(O)$_2$—, —NR$^2$S(O)$_2$CR$^2$R$^{2a}$—, —CR$^2$R$^{2a}$S(O)$_2$NR$^2$—, —NR²S(O)₂NR²—, —C(O)NR²—, —NR²C(O)—, —C(O)NR²CR²R²ᵃ—, —NR²C(O)CR²R²ᵃ—, —CR²R²ᵃC(O)NR²—, —CR²R²ᵃNR²C(O)—, —NR²C(O)O—, —OC(O)NR²—, —NR²C(O)NR²—, —NR²—, —NR²CR²R²ᵃ—, —CR²R²ᵃNR²—, O, —CR²R²ᵃO—, and —OCR²R²ᵃ—;

Y is selected from:
C₃₋₁₀ carbocycle substituted with 0–2 R⁴ᵃ, and
5–10 membered heterocycle containing from 1–4 heteroatoms selected from the group consisting of N, O, and S, substituted with 0–2 R⁴ᵃ;

R⁴, at each occurrence, is selected from H, (CH₂)ᵣOR², F, Cl, Br, I, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, —CN, NO₂, (CH₂)ᵣNR²R²ᵃ, (CH₂)ᵣC(O)R²ᶜ, NR²C(O)R²ᵇ, C(O)NR²R²ᵃ, NR²C(O)NR²R²ᵃ, C(=NR²)NR²R²ᵃ, C(=NS(O)₂R⁵)NR²R²ᵃ, NHC(=NR²)NR²R²ᵃ, C(O)NHC(=NR²)NR²R²ᵃ, SO₂NR²R²ᵃ, NR²SO₂NR²R²ᵃ, NR²SO₂—C₁₋₄ alkyl, NR²SO₂R⁵, S(O)ₚR⁵, and (CF₂)ᵣCF₃;

R⁴ᵃ, at each occurrence, is selected from H, =O, CHO, (CH₂)ᵣOR², (CH₂)ᵣ—F, (CH₂)ᵣ—Br, (CH₂)ᵣ—Cl, Cl, Br, F, I, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, —CN, NO₂, (CH₂)ᵣNR²R²ᵃ, (CH₂)ᵣC(O)R²ᶜ, NR²C(O)R²ᵇ, C(O)NR²R²ᵃ, (CH₂)ᵣN=CHOR³, C(O)NH(CH₂)₂NR²R²ᵃ, NR²C(O)NR²R²ᵃ, C(=NR²)NR²R²ᵃ, NHC(=NR²)NR²R²ᵃ, SO₂NR²R²ᵃ, NR²SO₂NR²R²ᵃ, NR²SO₂—C₁₋₄ alkyl, C(O)NHSO₂—C₁₋₄ alkyl, NR²SO₂R⁵, S(O)ₚR⁵, and (CF₂)ᵣCF₃;

R², at each occurrence, is selected from H, CF₃, C₁₋₆ alkyl, benzyl, C₃₋₆ carbocycle substituted with 0–2 R⁴ᵇ, a C₃₋₆ carbocycle-CH₂— substituted with 0–2 R⁴ᵇ, and 5–6 membered heterocycle containing from 1–4 heteroatoms selected from the group consisting of N, O, and S, substituted with 0–2 R⁴ᵇ;

alternatively, when R² is attached to an amino nitrogen, then R² is an amine protecting group;

R²ᵃ, at each occurrence, is selected from H, CF₃, C₁₋₆ alkyl, benzyl, C₃₋₆ carbocycle substituted with 0–2 R⁴ᵇ, and 5–6 membered heterocycle containing from 1–4 heteroatoms selected from the group consisting of N, O, and S, substituted with 0–2 R⁴ᵇ;

R²ᵇ, at each occurrence, is selected from CF₃, C₁₋₄ alkoxy, C₁₋₆ alkyl, benzyl, C₃₋₆ carbocycle substituted with 0–2 R⁴ᵇ, and 5–6 membered heterocycle containing from 1–4 heteroatoms selected from the group consisting of N, O, and S, substituted with 0–2 R⁴ᵇ;

R²ᶜ, at each occurrence, is selected from CF₃, OH, C₁₋₄ alkoxy, C₁₋₆ alkyl, benzyl, C₃₋₆ carbocycle substituted with 0–2 R⁴ᵇ, and 5–6 membered heterocycle containing from 1–4 heteroatoms selected from the group consisting of N, O, and S, substituted with 0–2 R⁴ᵇ;

alternatively, R² and R²ᵃ, together with the atom to which they are attached, combine to form a 5 or 6 membered saturated, partially saturated or unsaturated ring substituted with 0–2 R⁴ᵇ and containing from 0–1 additional heteroatoms selected from the group consisting of N, O, and S;

R³, at each occurrence, is selected from H, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, and phenyl;

R³ᵃ, at each occurrence, is selected from H, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, and phenyl;

R³ᵇ, at each occurrence, is selected from H, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, and phenyl;

R³ᶜ, at each occurrence, is selected from CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, and phenyl;

R⁴ᵇ, at each occurrence, is selected from H, =O, (CH₂)ᵣOR³, F, Cl, Br, I, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, —CN, NO₂, (CH₂)ᵣNR³R³ᵃ, (CH₂)ᵣC(O)R³, (CH₂)ᵣC(O)OR³ᶜ, NR³C(O)R³ᵃ, C(O)NR³R³ᵃ, NR³C(O)NR³R³ᵃ, C(=NR³)NR³R³ᵃ, NR³C(=NR³)NR³R³ᵃ, SO₂NR³R³ᵃ, NR³SO₂NR³R³ᵃ, NR³SO₂—C₁₋₄ alkyl, NR³SO₂CF₃, NR³SO₂-phenyl, S(O)ₚCF₃, S(O)ₚ—C₁₋₄ alkyl, S(O)ₚ-phenyl, and (CF₂)ᵣCF₃;

R⁵, at each occurrence, is selected from CF₃, C₁₋₆ alkyl, phenyl substituted with 0–2 R⁶, and benzyl substituted with 0–2 R⁶;

R⁶, at each occurrence, is selected from H, OH, (CH₂)ᵣOR², halo, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, CN, NO₂, (CH₂)ᵣNR²R²ᵃ, (CH₂)ᵣC(O)R²ᵇ, NR²C(O)R²ᵇ, NR²C(O)NR²R²ᵃ, C(=NH)NH₂, NHC(=NH)NH₂, SO₂NR²R²ᵃ, NR²SO₂NR²R²ᵃ, and NR²SO₂C₁₋₄ alkyl;

p, at each occurrence, is selected from 0, 1, and 2;
r, at each occurrence, is selected from 0, 1, 2, and 3; and
t, at each occurrence, is selected from 0, 1, 2, and 3.

2. A process according to claim 1, wherein:
R¹ᵃ is selected from CF₃, CO₂CH₃, CH₂CO₂CH₃, CO₂CH₂CH₃, S(O)₂CH₃, CH₂S(O)₂CH₃, C(O)NH₂, CH₂C(O)NH₂, SO₂NH₂, CH₂SO₂NH₂, pyridin-2-yl, pyridin-3-yl, pyridin-4-yl, pyridin-2-yl-N-oxide, pyridin-3-yl-N-oxide, pyridin-4-yl-N-oxide, imidazol-1-yl, CH₂-imidazol-1-yl, 1,2,3,4-tetrazol-1-yl, 1,2,3,4-tetrazol-5-yl, CH₂-1,2,3,4-tetrazol-1-yl, and CH₂-1,2,3,4-tetrazol-5-yl, provided that R¹ᵃ forms other than an N-halo, N—N, N—S, N—O, or N—CN bond;

X is selected from C₁₋₄ alkylene, —C(O)—, —C(O)CR²R²ᵃ—, —CR²R²ᵃC(O), —C(O)NR²—, —NR²C(O)—, —NR²—, —NR²CR²R²ᵃ—, —CR²R²ᵃNR²—, O, —CR²R²ᵃO—, and —OCR²R²ᵃ—;

Y is selected from one of the following carbocyclic and heterocycles that are substituted with 0–2 R⁴ᵃ;
cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

R⁴, at each occurrence, is selected from H, OR², CH₂OR², F, Cl, Br, I, CH₃, CH₂CH₃, CH₂CH₂CH₃, CH(CH₃)₂, CH₂CH₂CH₂CH₃, CH₂CH(CH₃)₂, CH(CH₃)CH₂CH₃, CH(CH₃)₃, —CN, NO₂, NR²R²ᵃ, CH₂NR²R²ᵃ, C(O)R²ᶜ, CH₂C(O)R²ᶜ, NR²C(O)R²ᵇ, C(O)NR²R²ᵃ, SO₂NR²R²ᵃ, S(O)ₚR⁵, and CF₃;

$R^{4a}$, at each occurrence, is selected from H, =O, CHO, $OR^2$, $CH_2OR^2$, Cl, Br, F, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, $NO_2$, $NR^2R^{2a}$, $CH_2NR^2R^{2a}$, $C(O)R^{2c}$, $CH_2C(O)R^{2c}$, $NR^2C(O)R^{2b}$, $C(O)NR^2R^{2a}$, $SO_2NR^2R^{2a}$, $S(O)_pR^5$, and $CF_3$;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, benzyl, $C_{3-6}$ carbocycle substituted with 0–2 $R^{4b}$, a $C_{3-6}$ carbocycle-$CH_2$— substituted with 0–2 $R^{4b}$, and 5–6 membered heterocycle containing from 1–4 heteroatoms selected from the group consisting of N, O, and S, substituted with 0–2 $R^{4b}$;

alternatively, when $R^2$ is attached to an amino nitrogen, then $R^2$ is an amine protecting group;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, benzyl, $C_{3-6}$ carbocycle substituted with 0–2 $R^{4b}$, and 5–6 membered heterocycle containing from 1–4 heteroatoms selected from the group consisting of N, O, and S, substituted with 0–2 $R^{4b}$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, benzyl, $C_{3-6}$ carbocycle substituted with 0–2 $R^{4b}$, and 5–6 membered heterocycle containing from 1–4 heteroatoms selected from the group consisting of N, O, and S, substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, benzyl, $C_{3-6}$ carbocycle substituted with 0–2 $R^{4b}$, and 5–6 membered heterocycle containing from 1–4 heteroatoms selected from the group consisting of N, O, and S, substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^{4b}$, at each occurrence, is selected from H, =O, $OR^3$, $CH_2OR^3$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $S(O)_p$—$C_{1-4}$ alkyl, $S(O)_p$-phenyl, and $CF_3$;

$R^5$, at each occurrence, is selected from $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, phenyl substituted with 0–2 $R^6$, and benzyl substituted with 0–2 $R^6$;

$R^6$, at each occurrence, is selected from H, OH, $OR^2$, $CH_2OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $SO_2NR^2R^{2a}$, $NR^2SO_2NR^2R^{2a}$, and $NR^2SO_2C_{1-4}$ alkyl; and, p, at each occurrence, is selected from 0, 1, and 2.

3. A process according to claim 2, wherein:

$NR^1R^2$ is selected from morpholino, pyrrolidino, and piperidino;

$R^{1a}$ is selected from $CF_3$, $S(O)_2CH_3$, and $C(O)NH_2$;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

$B^1$ is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N-methylaminomethyl)phenyl, 2-(N-ethyl-N-methylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(methylaminomethyl)-1-imidazolyl, 2-(N-(cyclopropylmethyl)aminomethyl)phenyl, 2-(N-(cyclobutyl)aminomethyl)phenyl, 2-(N-(cyclopentyl)aminomethyl)phenyl, 2-(N-(4-hydroxypiperidinyl)methyl)phenyl, and 2-(N-(3-hydroxypyrrolidinyl)methyl)phenyl; and, alternatively, $B^1$ is selected from the group: 2-(N-Pg-N-methylaminomethyl)phenyl, 2-(N-Pg-N-methylaminomethyl)-1-imidazolyl, 2-(N-Pg-N-(cyclopropylmethyl)aminomethyl)phenyl, 2-(N-Pg-N-(cyclobutyl)aminomethyl)phenyl, and 2-(N-Pg-N-(cyclopentyl)aminomethyl)phenyl.

4. A process according to claim 1, wherein the acid in reaction (b) is selected from: trifluoroacetic acid, sulfuric acid nitric acid, and hydrochloric acid.

5. A process according to claim 1, comprising subjecting a compound of formula IV to the following reactions that are performed, when applicable, in any order:

(c1) when ring D is a 3-cyano-4-fluorophenyl group, cyclizing ring D to 3-PgNH-benz[d]isoxazol-6-yl or 3-amino-benz[d]isoxazol-6-yl;

(c2) when ring D is substituted by a 2-cyano or 3-cyano group, reducing the cyano group to PgNH or $NH_2$;

(c3) when B is selected from Cl, Br, I, mesylate, tosylate, and $OSO_2Ph$, displacing it to form $B^1$;

(c4) when Pg is present, removing the Pg group;

(c5) when A-B is hydrogen, attaching a non-hydrogen A-B group to the 4,5-dihydro-pyrazolo[3,4-c]pyrid-2-one ring;

(c6) when $R^{4a}$ is CHO, aminating it to an aminomethyl group; and, (c7) when $R^{1a}$ is $CO_2H$ or $CO_2$-alkyl, amidating it to $C(O)NH_2$.

6. A process according to claim 1, comprising subjecting a compound of formula IV to the following reactions that are performed, when applicable, in any order:

(c3) when B is selected from Cl, Br, I, mesylate, tosylate, and $OSO_2Ph$, displacing it to form $B^1$;

(c4) when Pg is present, removing the Pg group;

(c6) when $R^{4a}$ is CHO, aminating it to an aminomethyl group.

7. A process according to claim 1, comprising subjecting a compound of formula IV to the following reactions that are performed, when applicable, in any order:

(c3) when B is selected from Cl, Br, I, mesylate, tosylate, and $OSO_2Ph$, displacing it to form $B^1$;

(c4) when Pg is present, removing the Pg group; and, (c7) when $R^{1a}$ is $CO_2H$ or $CO_2$-alkyl, amidating it to $C(O)NH_2$.

8. A process according to claim 1, comprising subjecting a compound of formula IV to the following reactions that are performed, when applicable, in any order:

(c6) when $R^{4a}$ is CHO, amidating it to an aminomethyl group.

9. A process according to claim 1, comprising subjecting a compound of formula IV to the following reactions that are performed, when applicable, in any order:

(c7) when $R^{1a}$ is $CO_2H$ or $CO_2$-alkyl, amidating it to $C(O)NH_2$.

* * * * *